(12) United States Patent
Obrecht et al.

(10) Patent No.: US 8,865,656 B2
(45) Date of Patent: Oct. 21, 2014

(54) BETA-HAIRPIN PEPTIDOMIMETICS HAVING CXCR4 ANTAGONIZING ACTIVITY

(75) Inventors: Daniel Obrecht, Bättwil (CH); Frank Gombert, Basel (CH); Alexander Lederer, Basel (CH); Barbara Romagnoli, Allschwil (CH); Christian Bisang, Basel (CH)

(73) Assignee: Polyphor AG, Allschwil (CH)

( * ) Notice: Subject to any disclaimer, the term of this patent is extended or adjusted under 35 U.S.C. 154(b) by 238 days.

(21) Appl. No.: 13/319,052

(22) PCT Filed: May 7, 2009

(86) PCT No.: PCT/EP2009/055563
§ 371 (c)(1),
(2), (4) Date: Jan. 18, 2012

(87) PCT Pub. No.: WO2010/127704
PCT Pub. Date: Nov. 11, 2010

(65) Prior Publication Data
US 2012/0135942 A1 May 31, 2012

(51) Int. Cl.
*A61K 38/00* (2006.01)
*C07K 7/54* (2006.01)
*A61P 35/00* (2006.01)
*C07K 7/08* (2006.01)
*C07K 7/02* (2006.01)

(52) U.S. Cl.
CPC .... *C07K 7/02* (2013.01); *C07K 7/08* (2013.01)
USPC .......................................... 514/21.1; 530/317

(58) Field of Classification Search
None
See application file for complete search history.

(56) References Cited

FOREIGN PATENT DOCUMENTS

| WO | WO 2004/096840 A1 | 11/2004 |
| WO | WO 2008/104090 A1 | 9/2008 |

OTHER PUBLICATIONS

International Search Report dated Oct. 11, 2010, issued in PCT/EP2009/055563.
Written Opinion of the International Searching Authority, date Oct. 11, 2010, issued in PCT/EP2009/055563.

*Primary Examiner* — Thomas Heard
(74) *Attorney, Agent, or Firm* — Birch, Stewart, Kolasch & Birch, LLP

(57) ABSTRACT

β-Hairpin peptidomimetics of the general formula Cyclo(-$Xaa^1$-$Xaa^2$-$Xaa^3$-$Cys^4$-$Xaa^5$-$Xaa^6$-$Xaa^7$-$Xaa^8$-$Arg^9$-$Tyr^{10}$-$Cys^{11}$-$Xaa^{12}$-$Xaa^{13}$-$Xaa^{14}$-$Xaa^{15}$-$Xaa^{16}$-), disulfide bond between $Cys^4$ and Cys11, and pharmaceutically acceptable salts thereof, with $Xaa^1$, $Xaa^2$, $Xaa^3$, $Xaa^5$, $Xaa^6$, $Xaa^7$, $Xaa^8$, $Xaa^{12}$, $Xaa^{13}$, $Xaa^{14}$, $Xaa^{15}$ and $Xaa^{16}$ being amino acid residues of certain types which are defined in the description and the claims, have CXCR4 antagonizing properties and can be used for preventing HIV infections in healthy individuals or for slowing and halting viral progression in infected patients; or where cancer is mediated or resulting from CXCR4 receptor activity; or where immunological diseases are mediated or resulting from CXCR4 receptor activity; or for treating immunosuppression; or during apheresis collections of peripheral blood stem cells and/or as agents to induce mobilization of stem cells to regulate tissue repair. These peptides can be manufactured by a process which is based on a mixed solid- and solution phase synthetic strategy.

11 Claims, No Drawings

SEQUENCE LISTING

```
<160> NUMBER OF SEQ ID NOS: 20

<210> SEQ ID NO 1
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
<222> LOCATION: (7)..(7)
<223> OTHER INFORMATION: X = D-Pro
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = D-Cha

<400> SEQUENCE: 1

Tyr His Ala Cys Ser Ala Xaa Xaa Arg Tyr Cys Tyr Gln Lys Xaa Pro
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
<222> LOCATION: (7)..(7)
<223> OTHER INFORMATION: X = D-Pro
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = NMe-D-Ile
```

```
<400> SEQUENCE: 2

Tyr His Ala Cys Ser Ala Xaa Xaa Arg Tyr Cys Tyr Gln Lys Xaa Pro
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
<222> LOCATION: (7)..(7)
<223> OTHER INFORMATION: X = D-Pro
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = D-Tyr

<400> SEQUENCE: 3

Tyr His Ala Cys Ser Ala Xaa Xaa Arg Tyr Cys Tyr Gln Lys Xaa Pro
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
<222> LOCATION: (7)..(7)
<223> OTHER INFORMATION: X = D-Pro
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = D-His

<400> SEQUENCE: 4

Tyr His Ala Cys Ser Ala Xaa Xaa Arg Tyr Cys Tyr Gln Lys Xaa Pro
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
<222> LOCATION: (7)..(7)
<223> OTHER INFORMATION: X = D-Pro
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = D-His(Bzl)

<400> SEQUENCE: 5

Tyr His Ala Cys Ser Ala Xaa Xaa Arg Tyr Cys Tyr Gln Lys Xaa Pro
1               5                   10                  15
```

```
<210> SEQ ID NO 6
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
<222> LOCATION: (7)..(7)
<223> OTHER INFORMATION: X = D-Pro
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = D-4Pal

<400> SEQUENCE: 6

Tyr His Ala Cys Ser Ala Xaa Xaa Arg Tyr Cys Tyr Gln Lys Xaa Pro
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
<222> LOCATION: (7)..(7)
<223> OTHER INFORMATION: X = D-Pro
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = NMe-D-Tyr

<400> SEQUENCE: 7

Tyr His Ala Cys Ser Ala Xaa Xaa Arg Tyr Cys Tyr Gln Lys Xaa Pro
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
<222> LOCATION: (7)..(7)
<223> OTHER INFORMATION: X = D-Pro
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = NMe-D-Lys

<400> SEQUENCE: 8

Tyr His Ala Cys Ser Ala Xaa Xaa Arg Tyr Cys Tyr Gln Lys Xaa Pro
1               5                   10                  15

<210> SEQ ID NO 9
<211> LENGTH: 16
<212> TYPE: PRT
<213> ORGANISM: Artificial Sequence
```

-continued

```
<220> FEATURE:
<223> OTHER INFORMATION: cyclic beta-hairpin peptidomimetic
<220> FEATURE:
<221> NAME/KEY: MISC_FEATURE
<222> LOCATION: (7)..(7)
<223> OTHER INFORMATION: X = D-Pro
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = (ABu)G

<400> SEQUENCE: 9

Tyr His Ala Cys Ser Ala Xaa Xaa Arg Tyr Cys Tyr Gln Lys Xaa Pro
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
<222> LOCATION: (7)..(7)
<223> OTHER INFORMATION: X = D-Tyr
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = D-Ile

<400> SEQUENCE: 10

Tyr His Ala Cys Ser Ala Xaa Xaa Arg Tyr Cys Tyr Gln Lys Xaa Pro
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
<222> LOCATION: (7)..(7)
<223> OTHER INFORMATION: X = D-Trp
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = D-Ile

<400> SEQUENCE: 11

Tyr His Ala Cys Ser Ala Xaa Xaa Arg Tyr Cys Tyr Gln Lys Xaa Pro
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
```

-continued

```
<222> LOCATION: (7)..(7)
<223> OTHER INFORMATION: X = D-Tyr
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = NMe-D-Ala

<400> SEQUENCE: 12

Tyr His Ala Cys Ser Ala Xaa Xaa Arg Tyr Cys Tyr Gln Lys Xaa Pro
 1               5                  10                  15

<210> SEQ ID NO 13
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
<222> LOCATION: (7)..(7)
<223> OTHER INFORMATION: X = D-Tyr
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = D-Tyr

<400> SEQUENCE: 13

Tyr His Ala Cys Ser Ala Xaa Xaa Arg Tyr Cys Tyr Gln Lys Xaa Pro
 1               5                  10                  15

<210> SEQ ID NO 14
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
<222> LOCATION: (7)..(7)
<223> OTHER INFORMATION: X = D-Tyr
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = D-Lys

<400> SEQUENCE: 14

Tyr His Ala Cys Ser Ala Xaa Xaa Arg Tyr Cys Tyr Gln Lys Xaa Pro
 1               5                  10                  15

<210> SEQ ID NO 15
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
<222> LOCATION: (7)..(7)
<223> OTHER INFORMATION: X = D-Tyr
<220> FEATURE:
<221> NAME/KEY: MISC_FEATURE
```

<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = D-Dab

<400> SEQUENCE: 15

Tyr His Ala Cys Ser Ala Xaa Xaa Arg Tyr Cys Tyr Gln Lys Xaa Pro
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
<222> LOCATION: (7)..(7)
<223> OTHER INFORMATION: X = D-Pro
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = D-Pro
<220> FEATURE:
<221> NAME/KEY: MISC_FEATURE
<222> LOCATION: (16)..(16)
<223> OTHER INFORMATION: X = Oic

<400> SEQUENCE: 16

Tyr His Ala Cys Ser Ala Xaa Xaa Arg Tyr Cys Tyr Gln Lys Xaa Xaa
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
<222> LOCATION: (5)..(5)
<223> OTHER INFORMATION: X = D-alloT
<220> FEATURE:
<221> NAME/KEY: MISC_FEATURE
<222> LOCATION: (7)..(7)
<223> OTHER INFORMATION: X = D-Pro
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = D-Pro

<400> SEQUENCE: 17

Tyr His Ala Cys Xaa Ala Xaa Xaa Arg Tyr Cys Tyr Gln Lys Xaa Pro
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE

```
<222> LOCATION: (1)..(1)
<223> OTHER INFORMATION: X = H-gamma4-DiHTyr-OH
<220> FEATURE:
<221> NAME/KEY: MISC_FEATURE
<222> LOCATION: (7)..(7)
<223> OTHER INFORMATION: X = D-Pro
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = D-Pro

<400> SEQUENCE: 18

Xaa His Ala Cys Ser Ala Xaa Xaa Arg Tyr Cys Tyr Gln Lys Xaa Pro
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
<222> LOCATION: (5)..(5)
<223> OTHER INFORMATION: X = Ahb
<220> FEATURE:
<221> NAME/KEY: MISC_FEATURE
<222> LOCATION: (7)..(7)
<223> OTHER INFORMATION: X = D-Pro
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = D-Pro

<400> SEQUENCE: 19

Tyr His Ala Cys Xaa Ala Xaa Xaa Arg Tyr Cys Tyr Gln Lys Xaa Pro
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: cyclic beta-hairpin peptidomimetic
<220> FEATURE:
<221> NAME/KEY: MISC_FEATURE
<222> LOCATION: (5)..(5)
<223> OTHER INFORMATION: X = H-beta3-HSer-OH
<220> FEATURE:
<221> NAME/KEY: MISC_FEATURE
<222> LOCATION: (7)..(7)
<223> OTHER INFORMATION: X = D-Pro
<220> FEATURE:
<221> NAME/KEY: MISC_FEATURE
<222> LOCATION: (8)..(8)
<223> OTHER INFORMATION: X = Dab
<220> FEATURE:
<221> NAME/KEY: MISC_FEATURE
<222> LOCATION: (15)..(15)
<223> OTHER INFORMATION: X = D-Pro

<400> SEQUENCE: 20

Tyr His Ala Cys Xaa Ala Xaa Xaa Arg Tyr Cys Tyr Gln Lys Xaa Pro
1               5                   10                  15
```

BETA-HAIRPIN PEPTIDOMIMETICS HAVING CXCR4 ANTAGONIZING ACTIVITY

The present invention provides β-hairpin peptidomimetics which are having CXCR4 antagonizing activity.

The β-hairpin peptidomimetics of the invention are Cyclo(-Xaa$^1$-Xaa$^2$-Xaa$^3$-Cys$^4$-Xaa$^5$-Xaa$^6$-Xaa$^7$-Xaa$^8$-Arg$^9$-Tyr$^{10}$-Cys$^{11}$-Xaa$^{12}$-Xaa$^{13}$-Xaa$^{14}$-Xaa$^{15}$-Xaa$^{16}$-), disulfide bond between Cys$^4$ and Cys$^{11}$, and pharmaceutically acceptable salts thereof, with Xaa$^1$ being Tyr or a γ-amino acid residue of type M as described herein below, Xaa$^2$ being His, Tyr, Arg or Lys, Xaa$^3$ being Ala or Tyr, Xaa$^5$ being Ser or the D-isomer of an amino acid residue of type F as described herein below or a γ-amino acid residue of type M or a β-amino acid of type N as described herein below, Xaa$^6$ being Ala or a β-amino acid residue of type N as described herein below, Xaa$^7$ being -A-CO— as described herein below or the D-isomer of an amino acid residue of type D as described herein below, Xaa$^8$ being Dab, Arg, Tyr or Thr, Xaa$^{12}$ being Tyr or a γ-amino acid residue of type M as described herein below, Xaa$^{13}$ being Gln or a γ-amino acid residue of type M as described herein below, Xaa$^{14}$ being Lys, Orn, Ala, Gln or Glu, Xaa$^{15}$ being -A-CO— as described herein below or the D-isomer of an amino acid residue of type C, or of type D, or of type E, or of type F, as described herein below or a N-substituted glycine of type I as described herein below, and Xaa$^{16}$ being —B—CO— as described herein below; with the proviso that Xaa$^1$ is a γ-amino acid residue of type M as defined herein below; and/or Xaa$^5$ is the D-isomer of an amino acid residue of type F as defined herein below, or a γ-amino acid residue of type M as defined herein below, or a β-amino acid residue of type N as defined herein below; and/or Xaa$^6$ is a β-amino acid residue of type N as defined herein below; and/or Xaa$^{12}$ is a γ-amino acid residue of type M as defined herein below; and/or Xaa$^{13}$ is a γ-amino acid residue of type M as defined herein below; and/or Xaa$^{15}$ is the D-isomer of an amino acid residue of type C, or of type D, or of type E, or of type F as defined herein below, or an N-substituted glycine residue of type I as defined herein below; and/or Xaa$^{16}$ is —B—CO— with B being the enantiomer of group A105 as defined herein below.

In addition, the present invention provides an efficient synthetic process by which these compounds can, if desired, be made in parallel library-format. These β-hairpin peptidomimetics show improved efficacy, bioavailability, and most importantly a significantly enhanced ratio between CXCR4 antagonizing activity on the one hand, and reduced hemolysis of red blood cells and reduced or no cytotoxicity on the other.

Many medically significant biological processes are mediated by signal transduction that involves chemokines and their receptors in general and stromal derived factor 1 (SDF-1/CXCL12) and its receptor CXCR4 in particular.

CXCR4 and its ligand SDF-1 are involved in trafficking of B cells, hematopoietic stem cells (HSC) and hematopoietic progenitor cells (HPC). For instance, CXCR4 is expressed on CD34+ cells, and has been implicated in the process of CD34+ cell migration and homing (S. M. Watt, S. P. Forde, *Vox sanguinis* 2008, 94, 18-32). It has also been shown that the CXCR4 receptor plays an important role in the release of stem and progenitor cells from the bone marrow to the peripheral blood (L. M. Pelus, S. Fukuda, *Leukemia* 2008, 22, 466-473). This activity of CXCR4 could be very important for efficient apheresis collections of peripheral blood stem cells. Autologous peripheral blood cells provide a rapid and sustained hematopoietic recovery following auto-transplantation after the administration of high-dose chemotherapy or radiotherapy in patients with haematological malignancies and solid tumors. (W. C. Liles et al., *Blood* 2003, 102, 2728-2730).

Recently, it has been demonstrated that SDF-1 is locally up-regulated in animal models of injury including focal ischemic stroke, global cerebral ischemia, myocardial infarction and hind limb ischemia as well as being involved in recovery after peripheral ischemia or following injury to the liver, kidney or lung (A. E. Ting, R. W. Mays, M. R. Frey, W. Van't Hof, S. Medicetty, R. Deans, *Critical Reviews in Oncology/Hematology* 2008, 65, 81-93 and literature cited herein; F. Lin, K. Cordes, L. Li, L. Hood, W. G. Couser, S. J. Shankland et al., *J. Am. Soc. Nephrol.* 2003, 14, 1188-1199; C. C. Dos Santos, *Intensive Care Med.* 2008, 34, 619-630). These results suggest that SDF-1 may be a chemoattractant for CXCR4-positive stem cells for tissue and organ repair/regeneration (M. Z. Ratajczak, M. Kucia, R. Reca, M. Majka, A. Janowska-Wieczorek, J. Ratajczak, *Leukemia* 2004, 18, 29-40). Therefore, modulating the SDF-1/CXCR4 axis by CXCR4 inhibitors should result in a significant therapeutic benefit by using released stem cells to regulate tissue repair.

More recently, it has been shown that disrupting the CXCR4/SDF-1 retention axis by CXCR4 inhibitors plays a crucial role in differential mobilization of progenitor cells like HPCs, endothelial (EPCs) and stromal progenitor cells (SPCs) from the bone marrow (S. C. Pitchford, R. C. Furze, C. P. Jones, A. M. Wegner, S. M. Rankin, *Cell Stem Cell* 2009, 4, 62). In addition, bone marrow-derived CXCR4+ Very Small Embryonic-Like Stem Cells (VSELs) were mobilized in patients with acute myocardial infarction indicating a hypothetical reparatory mechanism (W. Wojakowski, M. Tendra, M. Kucia, E. Zuba-Surma, E. Paczkowska, J. Ciosek, M. Halasa, M. Król, M. Kazmierski, P. Buszman, A. Ochala, J. Ratajczak, B. Machalinski, M. Z. Ratajczak *J. Am. Coll. Cardiol.* 2009, 53, 1). These findings may be exploited to provide efficacious stem cell therapy for tissue regeneration.

There is increasing evidence suggesting that chemokines in general and the SDF-1/CXCR4 interaction in particular play a pivotal role in angiogenesis. Chemokines induce angiogenesis directly by binding their cognate receptors on endothelial cells or indirectly by promoting inflammatory cell infiltrates, which deliver other angiogenic stimuli. A number of proinflammatory chemokines including interleukin 8 (IL-8), growth-regulated oncogene, stromal cell-derived factor 1 (SDF-1), monocyte chemotactic protein 1 (MCP-1), eotaxin 1, and I-309 have been shown to act as direct inducers of angiogenesis. (X. Chen, J. A. Beutler, T. G. McCloud, A. Loehfelm, L. Yang, H. F. Dong, O. Y. Chertov, R. Salcedo, J. J. Oppenheim, O. M. Howard. *Clin. Cancer Res.* 2003, 9(8), 3115-3123; R. Salcedo, J. J. Oppenheim, *Microcirculation* 2003, (3-4), 359-370).

Recently obtained results show that the CXCR4 receptor is involved in the chemotactic activity of cancer cells, such as breast cancer metastasis or in metastasis of ovarian cancer (A. Muller, B. Homey, H. Soto, N. Ge, D. Catron, M. E. Buchanan, T. Mc Clanahan, E. Murphey, W. Yuan, S. N. Wagner, J. L. Barrera, A. Mohar, E. Verastegui, A. Zlotnik, *Nature* 2001, 50, 410; J. M. Hall, K. S. Korach, *Molecular Endocrinology* 2003, 17, 792-803.), Non-Hodgin's Lymphoma (F. Bertolini, C. Dell'Agnola, P. Manusco, C. Rabascio, A. Burlini, S. Monestiroli, A. Gobbi, G. Pruneri, G. Martinelli, *Cancer Research* 2002, 62, 3106-3112), or lung cancer (T. Kijima, G. Maulik, P. C. Ma, E. V. Tibaldi, R. E. Turner, B. Rollins, M. Sattler, B. E. Johnson, R. Salgia, *Cancer Research* 2002, 62, 6304-6311), melanoma, prostate cancer, kidney cancer, neuroblastomia, pancreatic cancer, multiple myeloma, chronic lymphocytic leukemia, hepatocellular carcinoma, colorectal carcinoma, endometrial cancer, germ cell tumor (H. Tamamura et al., *FEBS Letters* 2003, 550, 79-83, cited ref.; Z. Wang, Q. Ma, Q. Liu, H. Yu, L. Zhao, S. Shen, J. Yao, British Journal of Cancer 2008, 99, 1695; B. Sung, S. Jhurani, K. S. Ahn, Y. Mastuo, T. Yi, S. Guha, M. Liu, B. Aggarwal, *Cancer Res.* 2008, 68, 8938; H. Liu, Z. Pan, A. Li, S. Fu, Y. Lei, H. Sun, M. Wu, W. Zhou, *Cellular and Molecular Immunology*, 2008, 5, 373; C. Rubie, O. Kollmari, V. O. Frick, M. Wagner, B. Brittner, S. Gräber, M. K. Schilling, *Scandinavian Journal of Immunology* 2008, 68, 635; S. Gelmini, M. Mangoni, F. Castiglioe, C. Beltrami, A. Pieralli, K. L. Andersson, M. Fambrini, G. l. Taddie, M. Serio, C. Orlando, *Clin. Exp. Metastasis* 2009, 26, 261; D. C. Gilbert, I. Chandler, A. McIntyre, N. C. Goddrd, R. Gabe, R. A. Huddart, J. Shipley, *J. Pathol.* 2009, 217, 94). Blocking the chemotactic activity with a CXCR4 inhibitor should stop the migration of cancer cells and thus metastasis.

CXCR4 has also been implicated in the growth and proliferation of solid tumors and leukemia/lymphoma. It was shown that activation of the CXCR4 receptor was critical for the growth of both malignant neuronal and glial tumors. Moreover, systemic administration of the CXCR4 antagonist AMD3100 inhibits growth of intracranial glioblastoma and medulloblastoma xenografts by increasing apoptosis and decreasing the proliferation of tumor cells (J. B. Rubin, A. L Kung, R. S Klein, J. A. Chan, Y. Sun, K. Schmidt, M. W. Kieran, A. D. Luster, R. A. Segal, *Proc Natl Acad Sci U S A.* 2003, 100(23), 13513-13518; S. Barbero, R. Bonavia, A. Bajetto, C. Porcile, P. Pirani, J. L. Ravetti, G. L. Zona, R. Spaziante, T. Florio, G. Schettini, *Cancer Res.* 2003, 63(8), 1969-1974; T. Kijima, G. Maulik, P. C. Ma, E. V. Tibaldi, R. E. Turner, B. Rollins, M. Sattler, B. E. Johnson, R. Salgia. *Cancer Res.* 2002, 62(21), 6304-6311). CXCR4 inhibitors also showed promising in vitro and in vivo efficacies in breast cancer, small cell lung cancer, pancreatic cancer, gastric cancer, colorectal cancer, malignant melanoma, ovarian cancer, rhabdomyo-sarcoma, prostate cancer as well as chronic lymphocytic leukemia, acute myelogenous leukemia, acute lymphoblastic leukemia, multiple myeloma and Non-Hodgkin's lymphoma (J. A. Burger, A. Peled, *Leukemia* 2009, 23, 43-52 and literature cited herein).

It is well established that chemokines are involved in a number of inflammatory pathologies and some of them show a pivotal role in the modulation of osteoclast development. Immunostaining for SDF-1 (CXCL12) on synovial and bone tissue biopsies from both rheumatoid arthritis (RA) and osteoarthritis (OA) samples have revealed strong increases in the expression levels of chemokines under inflammatory conditions (F. Grassi, S. Cristino, S. Toneguzzi, A. Piacentini, A. Facchini, G. Lisignoli, *J. Cell Physiol.* 2004; 199(2), 244-251). It seems likely that the CXCR4 receptor plays an important role in inflammatory diseases such as rheumatoid arthritis, asthma, or multiple sclerosis (K. R. Shadidi et al., *Scandinavian Journal of Immunology* 2003, 57, 192-198; J. A. Gonzalo, *J. Immunol.* 2000, 165, 499-508; S. Hatse et al., *FEBS Letters* 2002, 527, 255-262 and cited references). The mediation of recruitment of immune cells to sites of inflammation should be stopped by a CXCR4 inhibitor.

To date the available therapies for the treatment of HIV infections have been leading to a remarkable improvement in symptoms and recovery from disease in infected people. Although the highly active anti retroviral therapy (HAART) which involves a combination of reverse transcriptase/protease-inhibitor has dramatically improved the clinical treatment of individuals with AIDS or HIV infection, there have still remained several serious problems including multi drug resistance, significant adverse effects and high costs.

Particularly desired are anti HIV agents that block the HIV infection at an early stage of the infection, such as the viral entry. It has recently been recognized that for efficient entry into target cells, human immunodeficiency viruses require the chemokine receptors CCR5 and CXCR4 as well as the primary receptor CD4 (N. Levy, *Engl. J. Med.* 1996, 335, 1528-1530). Accordingly, an agent which could block the CXCR4 chemokine receptors should prevent infections in healthy individuals and slow or halt viral progression in infected patients (J. Cohen, *Science* 1997, 275, 1261-1264).

Among the different types of CXCR4 inhibitors (M. Schwarz, T. N. C. Wells, A. E. I. Proudfoot, *Receptors and Channels* 2001, 7, 417-428; Y. Lavrovsky, Y. A. Ivanenkov, K. V. Balakin, D. A. Medvedewa, P. V. Ivachtchenko, *Mini Rev. Med. Chem.* 2008, 11, 1075-1087), one emerging class is based on naturally occurring cationic peptide analogues derived from Polyphemusin II which have an antiparallel β-sheet structure, and a β-hairpin that is maintained by two disulfide bridges (H. Nakashima, M. Masuda, T. Murakami, Y. Koyanagi, A. Matsumoto, N. Fujii, N. Yamamoto, *Antimicrobial Agents and Chemoth.* 1992, 36, 1249-1255; H. Tamamura, M. Kuroda, M. Masuda, A. Otaka, S. Funakoshi, H. Nakashima, N. Yamamoto, M. Waki, A. Matsumotu, J. M. Lancelin, D. Kohda, S. Tate, F. Inagaki, N. Fujii, *Biochim. Biophys. Acta* 1993, 209, 1163; WO 95/10534 A1).

Synthesis of structural analogs and structural studies by nuclear magnetic resonance (NMR) spectroscopy have shown that the cationic peptides adopt well defined β-hairpin conformations, due to the constraining effect of the one or two disulfide bridges (H. Tamamura, M. Sugioka, Y. Odagaki, A. Omagari, Y. Kahn, S. Oishi, H. Nakashima, N. Yamamoto, S. C. Peiper, N. Hamanaka, A. Otaka, N. Fujii, *Bioorg. Med. Chem. Lett.* 2001, 359-362). These results show that the β-hairpin structure plays an important role in CXCR4 antagonizing activity.

Additional structural studies have also indicated that the antagonizing activity can also be influenced by modulating amphiphilic structure and the pharmacophore (H. Tamamura, A. Omagari, K. Hiramatsu, K. Gotoh, T. Kanamoto, Y. Xu, E. Kodama, M. Matsuoka, T. Hattori, N. Yamamoto, H. Nakashima, A. Otaka, N. Fujii, *Bioorg. Med. Chem. Lett.* 2001, 11, 1897-1902; H. Tamamura, A. Omagari, K. Hiramatsu, S. Oishi, H. Habashita, T. Kanamoto, K. Gotoh, N. Yamamoto, H. Nakashima, A. Otaka N. Fujii, *Bioorg. Med. Chem.* 2002, 10, 1417-1426; H. Tamamura, K. Hiramatsu, K. Miyamoto, A. Omagari, S. Oishi, H. Nakashima, N. Yamamoto, Y. Kuroda, T. Nakagawa, A. Otaki, N. Fujii, *Bioorg. Med. Chem. Letters* 2002, 12, 923-928).

The compounds Cyclo (-Xaa$^1$-Xaa$^2$-Xaa$^3$-Cys$^4$-Xaa$^5$-Xaa$^6$-Xaa$^7$-Xaa$^8$-Arg$^9$-Tyr$^{10}$-Cys$^{11}$-Xaa$^{12}$-Xaa$^{13}$-Xaa$^{14}$-Xaa$^{15}$-Xaa$^{16}$-), disulfide bond between Cys$^4$ and Cys$^{11}$, are cyclic β-hairpin peptidomimetics exhibiting high CXCR4 antagonizing activity, being useful for efficient apheresis collections of mobilized peripheral blood stem cells and/or using these mobilized cells to regulate tissue repair, and having anticancer activity, anti inflammatory activity and anti HIV activity.

The cyclic β-hairpin conformation is induced by the D-amino acid residue Xaa$^7$ and the D-amino acid or N-substituted glycine residue Xaa$^{15}$ and fostered by the conserved amino acids at positions 4, 9, 10 and 11 within the sequence. Further stabilization of the hairpin conformation is achieved by the disulfide bridge between Cys$^4$ and Cys$^{11}$. In addition, incorporation of structural elements derived from β- and γ-amino acids into cyclic β-hairpin peptidomimetics has been realized, a new approach which has not previously been evaluated for development of β-hairpin peptidomimetics of that ring size with CXCR4 antagonizing activity.

Backbone modifications, such as incorporation of β- and/or γ-amino acids into cyclic β-hairpin peptidomimetics may enhance peptide recognition by altering both the electronic conditions of the amide bonds and the degrees of conformational freedom following insertion of one or two additional methylene groups according to β- or γ-amino acids (J. Nurbo, S. D. Peterson, G. Dahl, U. H. Danielson, A. Karlén, A. Sandström, *Bioorg. Med. Chem.* 2008, 16, 5590; G. Guichard, A. Zerbib, F.-A. Le Gal, J. Hoebeke, F. Connan, J. Choppin, J.-P. Briand, J.-G. Guillet, *J. Med. Chem.* 2000, 42, 3803). Moreover, as human peptidases generally do not recognize peptides containing β- or γ-amino acids these peptides should be more resistant to proteolytic degradation (M.-I. Aguilar, A. W. Purcell, R. Devi, R. Lew, J. Rossjohn, A. I. Smith, P. Perlmutter, *Org. Biomol. Chem.* 2007, 5, 2884; D. F. Hook, P. Bindschaedler, Y. R. Mahayan, R. Sebesta, P. Kast, D. Seebach, *Chem. Biodivers.* 2005, 2, 591; P. Zubrzak, H. Williams, G. M. Coast, R. E. Isaac, G. Reyes-Rangel, E. Juaristi, J. Zabrocki, R. J. Nachman, Biopolymers 2007, 88, 76; S. Sagan, Th. Milcent, R. Ponsinet, O. Convert, O. Tasseau, G. Chassaing, S. Lavielle, O. Lequin, *Eur. J. Biochem.* 2003, 270, 939).

β-hairpin mimetic peptides have been described in the literature (D. Obrecht, M. Altorfer, J. A. Robinson, *Adv. Med. Chem.* 1999, 4, 1-68; J. A. Robinson, *Syn. Lett.* 2000, 4, 429-441), and the ability to generate β-hairpin peptidomimetics using combinatorial and parallel synthesis methods has now been established (L. Jiang, K. Moehle, B. Dhanapal, D. Obrecht, J. A. Robinson, *Helv. Chim. Acta.* 2000, 83, 3097-3112). However, the additional incorporation of structural elements derived from β- and γ-amino acids into β-hairpin mimetics by applying and altering these methods has not previously been evaluated for development of CXCR4 antagonizing peptides of that ring size. The methods described here allow the synthesis and screening of large hairpin mimetic libraries, which in turn considerably facilitates structure-activity studies, and hence the discovery of new molecules with highly potent CXCR4 antagonizing activity or anti cancer activity or anti inflammatory activity or anti HIV activity and low hemolytic activity to human red blood cells.

β-Hairpin peptidomimetics obtained by the approach described here can be used in apheresis collections of peripheral blood stem cells and/or as agents to induce mobilization of stem cells to regulate tissue repair or are useful as anticancer agents, as inhibitors of tumor growth or as apoptosis inducing agents, as anti-metastasis agents, as anti inflammatory agents and as anti-HIV agents.

The β-hairpin peptidomimetics of the present invention are compounds of the general formula Cyclo(-$Xaa^1$-$Xaa^2$-$Xaa^3$-$Cys^4$-$Xaa^5$-$Xaa^6$-$Xaa^2$-$Xaa^8$-$Arg^9$-$Tyr^{10}$-$Cys^{11}$-$Xaa^{12}$-$Xaa^{13}$-$Xaa^{14}$-$Xaa^{15}$-$Xaa^{16}$-), disulfide bond between $Cys^4$ and $Cys^{11}$,
wherein
$Xaa^1$ is Tyr or a γ-amino acid residue of type M as defined herein below,
$Xaa^2$ is His, Tyr, Arg or Lys,
$Xaa^3$ is Ala or Tyr,
$Xaa^5$ is Ser or the D-isomer of an amino acid residue of type F as defined herein below or a γ-amino acid residue of type M as defined herein below or an β-amino acid of type N as defined herein below,
$Xaa^6$ is Ala or a β-amino acid residue of type N as described herein below,
$Xaa^7$ is -A-CO— as described hereafter or the D-isomer of an amino acid residue of type D as described herein below,
$Xaa^8$ is Dab, Arg, Tyr or Thr,
$Xaa^{12}$ is Tyr or a γ-amino acid residue of type M as described herein below,
$Xaa^{13}$ is Gln or an γ-amino acid residue of type M as described herein below,
$Xaa^{14}$ is Lys, Orn, Ala, Gln or Glu,
$Xaa^{15}$ is -A-CO— as described herein below or the D-isomer of an amino acid residue of type C, or of type D, or of type E, or of type F, as described herein below or a N-substituted glycine residue of type I as described herein below, and
$Xaa^{16}$ is —B—CO— as described herein below;
with the proviso that
$Xaa^1$ is a γ-amino acid residue of type M as defined herein below;
and/or
$Xaa^5$ is the D-isomer of an amino acid residue of type F as defined herein below, or a γ-amino acid residue of type M as defined herein below, or a β-amino acid residue of type N as defined herein below;
and/or
$Xaa^6$ is a β-amino acid residue of type N as defined herein below;
and/or
$Xaa^{12}$ is a γ-amino acid residue of type M as defined herein below;
and/or
$Xaa^{13}$ is a γ-amino acid residue of type M as defined herein below;
and/or
$Xaa^{15}$ is the D-isomer of an amino acid residue of type C, or of type D, or of type E, or of type F as defined herein below, or an N-substituted glycine residue of type I as defined herein below;
and/or
$Xaa^{16}$ is —B—CO— with B being the enantiomer of group A105 as defined herein below;
—B—CO— is Gly, or the residue of an L-α-amino acid with B being a residue of formula —$NR^{20}CH(R^{71})$—, or —$NR^{20}CH(R^{72})$—, or —$NR^{20}CH(R^{73})$— or —$NR^{20}CH(R^{74})$— or —$NR^{20}CH(R^{84})$— or the enantiomer of one of the groups A1 to A69 and A105 as defined hereinafter;
A of -A-CO— is a group of one of the formulae

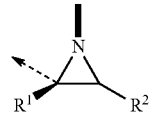

A1

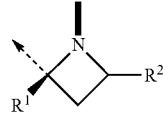

A2

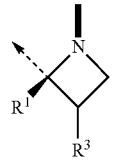

A3

-continued
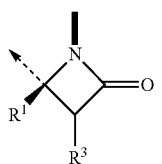
A4
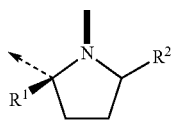
A5
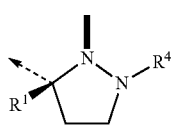
A6
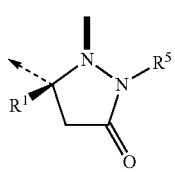
A7
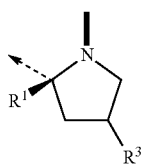
A8
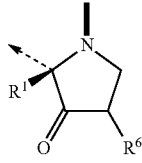
A9
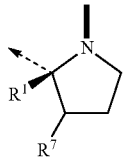
A10
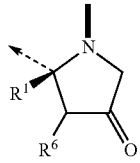
A11
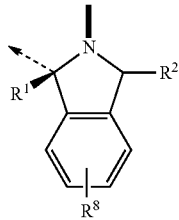
A12
-continued
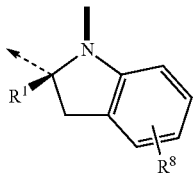
A13
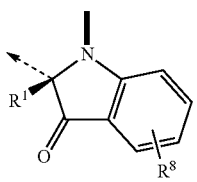
A14
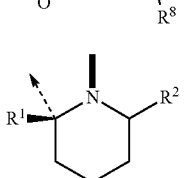
A15
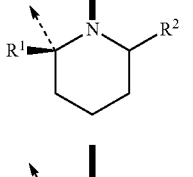
A16
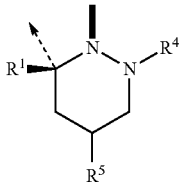
A17
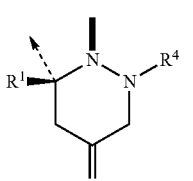
A18
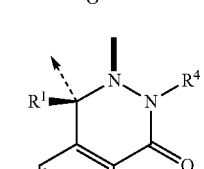
A19
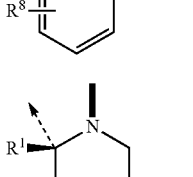
A20
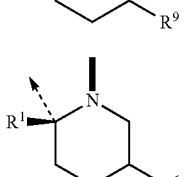
A21
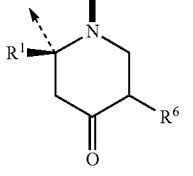

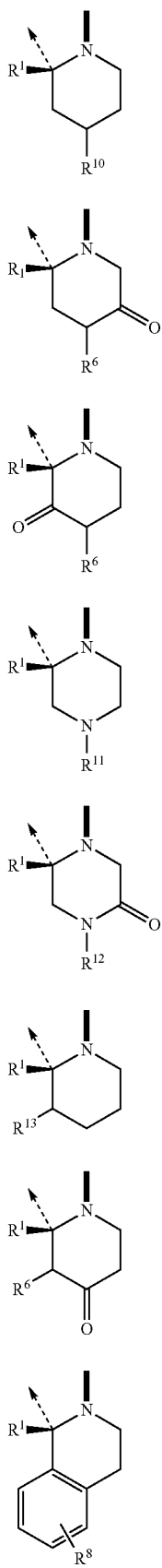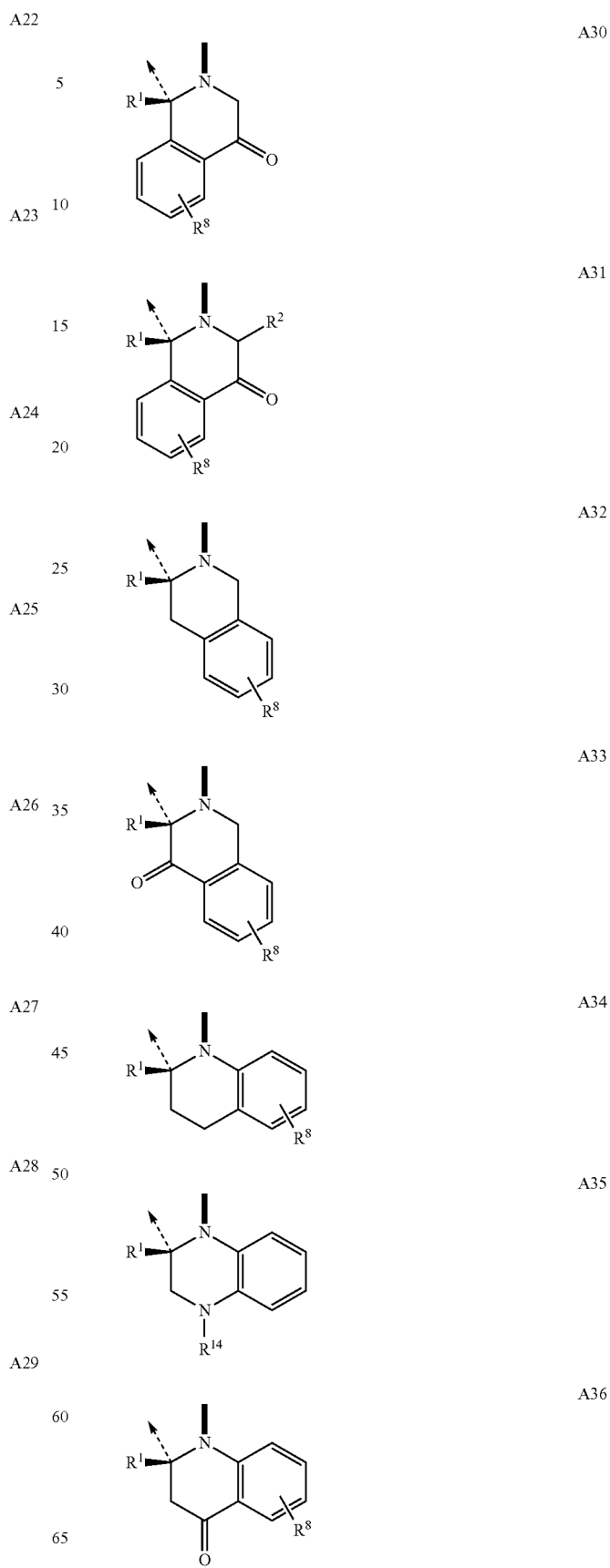

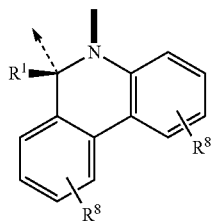
A37
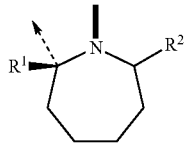
A38
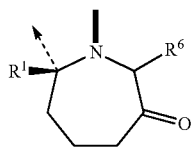
A39
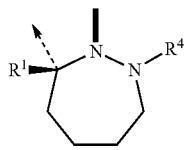
A40
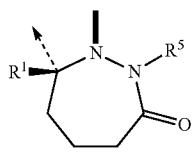
A41
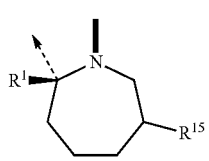
A42
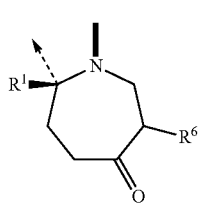
A43
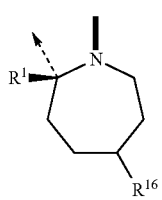
A44
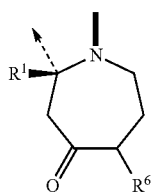
A45
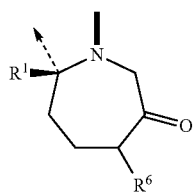
A46
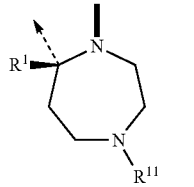
A47
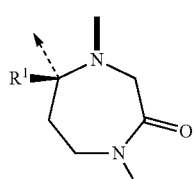
A48
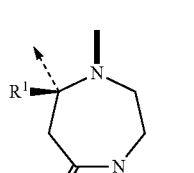
A49
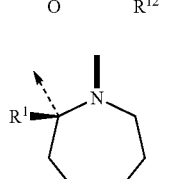
A50
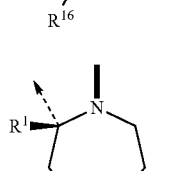
A51
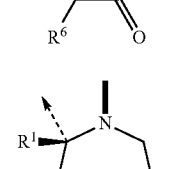
A52
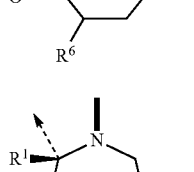
A53
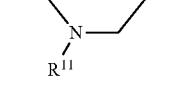

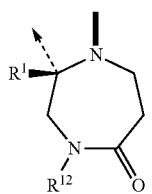 A54
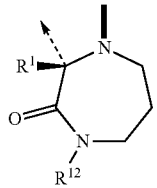 A55
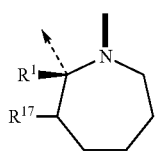 A56
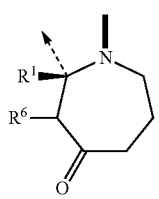 A57
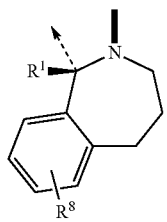 A58
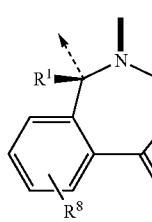 A59
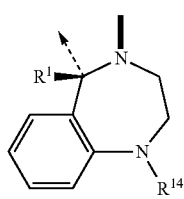 A60
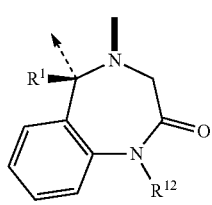 A61
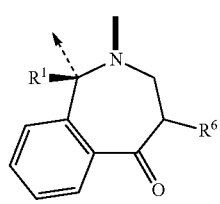 A62
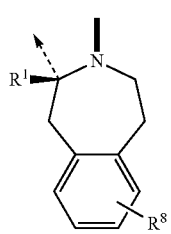 A63
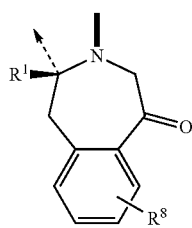 A64
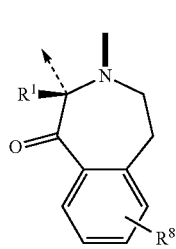 A65
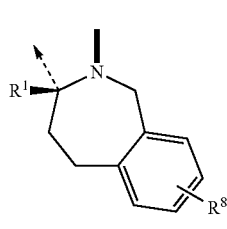 A66
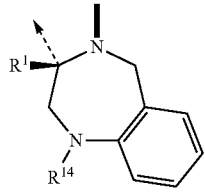 A67
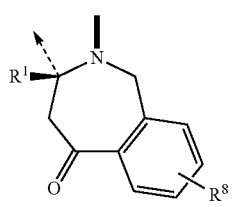 A68

-continued
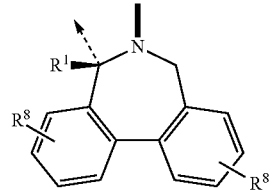
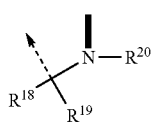
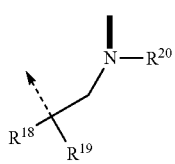
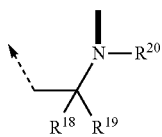
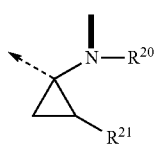
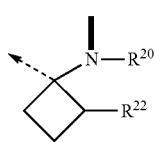
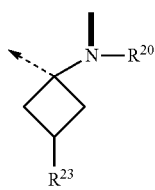
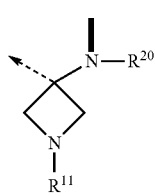
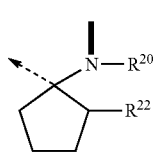
-continued
A69
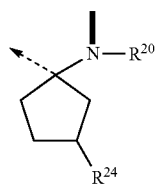
A70
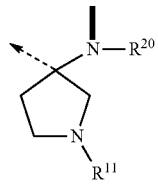
A71
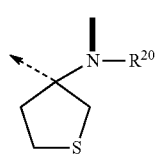
A72
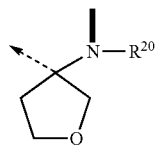
A73
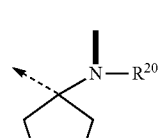
A74
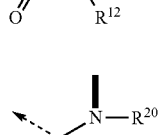
A75
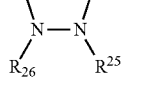
A76
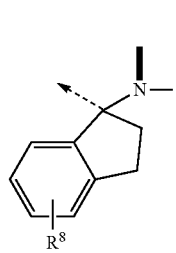
A77
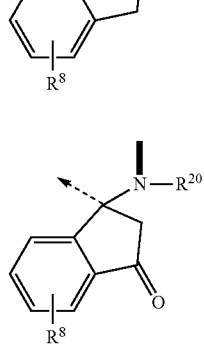
A78
A79
A80
A81
A82
A83
A84
A85

-continued
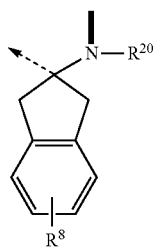
A86
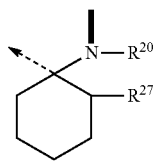
A87
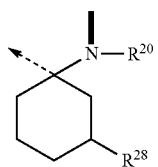
A88
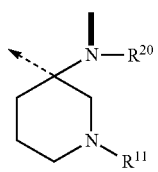
A89
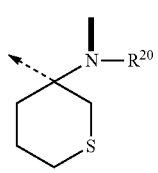
A90
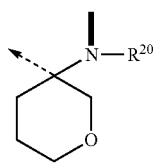
A91
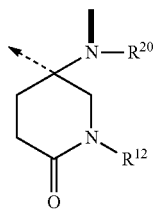
A92
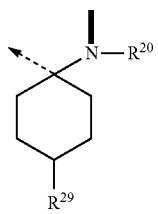
A93
-continued
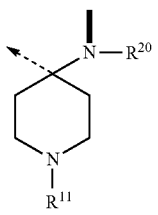
A94
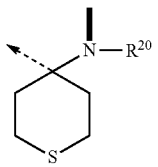
A95
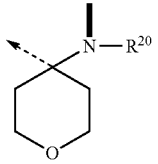
A96
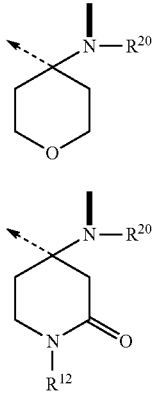
A97
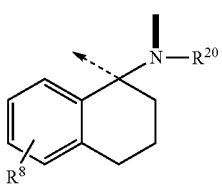
A98
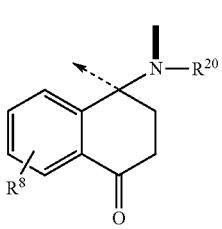
A99
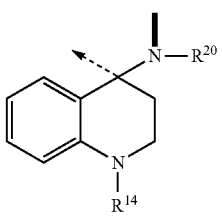
A100
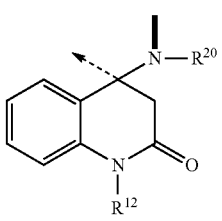
A101

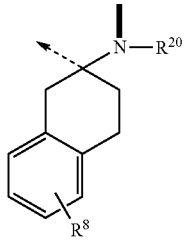

A102

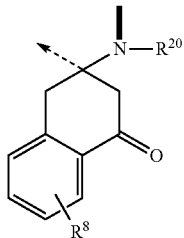

A103

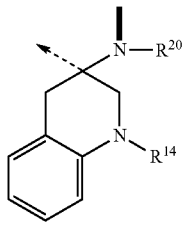

A104

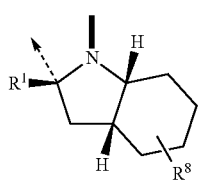

A105

$R^1$ is H; lower alkyl; or aryl-lower alkyl;
$R^2$ is H; alkyl; alkenyl; $-(CH_2)_p(CHR^{61})_sOR^{55}$; $-(CH_2)_p(CHR^{61})_sSR^{56}$; $-(CH_2)_p(CHR^{61})_sNR^{33}R^{34}$; $-(CH_2)_p(CHR^{61})_sOCONR^{33}R^{75}$; $-(CH_2)_p(CHR^{61})_s NR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sR^{77}$;

$R^3$ is alkyl; alkenyl; $-(CH_2)_o(CHR^{61})_sOR^{55}$; $-(CH_2)_o(CHR^{61})_sSR^{56}$; $-(CH_2)_o(CHR^{61})_sNR^{33}R^{34}$; $-(CH_2)_o(CHR^{61})_sOCONR^{33}R^{75}$; $-(CH_2)_o(CHR^{61})_s NR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;

$R^4$ is H; alkyl; alkenyl; $-(CH_2)_m(CHR^{61})_sOR^{55}$; $-(CH_2)_m(CHR^{61})_sSR^{56}$; $-(CH_2)_m(CHR^{61})_sNR^{33}R^{34}$; $-(CH_2)_m(CHR^{61})_sOCONR^{33}R^{75}$; $-(CH_2)_m(CHR^{61})_sNR^{20}CONR^{33}R^{82}$; $-(CH_2)_p(CHR^{61})_sCOOR^{57}$; $-(CH_2)_p(CHR^{61})_sCONR^{58}R^{59}$; $-(CH_2)_p(CHR^{61})_sPO(OR^{60})_2$; $-(CH_2)_p(CHR^{61})_sSO_2R^{62}$; or $-(CH_2)_o(CHR^{61})_sC_6H_4R^8$;

$R^5$ is H; alkyl; alkenyl; $-(CH_2)_m(CHR^{61})_sOR^{55}$; $-(CH_2)_m(CHR^{61})_sSR^{56}$; $-(CH_2)_m(CHR^{61})_sNR^{33}R^{34}$; $-(CH_2)_m(CHR^{61})_sOCONR^{33}R^{75}$; $-(CH_2)_m(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;

$R^6$ is H; alkyl; alkenyl; $-(CH_2)_o(CHR^{61})_sOR^{55}$; $-(CH_2)_o(CHR^{61})_sSR^{56}$; $-(CH_2)_o(CHR^{61})_sNR^{33}R^{34}$; $-(CH_2)_o(CHR^{61})_sOCONR^{33}R^{75}$; $-(CH_2)_o(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;

$R^7$ is alkyl; alkenyl; $-(CH_2)_q(CHR^{61})_sOR^{55}$; $-(CH_2)_q(CHR^{61})_sNR^{33}R^{34}$; $-(CH_2)_q(CHR^{61})_sOCONR^{33}R^{75}$; $-(CH_2)_q(CHR^{61})_sNR^{20}CONR^{33}R^{82}$; $-(CH_2)_r(CHR^{61})_sCOOR^{57}$; $-(CH_2)_r(CHR^{61})_sCONR^{58}R^{59}$; $-(CH_2)_r(CHR^{61})_sPO(OR^{60})_2$; $-(CH_2)_r(CHR^{61})_sSO_2R^{62}$; or $-(CH_2)_r(CHR^{61})_sC_6H_4R^8$;

$R^8$ is H; Cl; F; $CF_3$; $NO_2$; lower alkyl; lower alkenyl; aryl; aryl-lower alkyl; $-(CH_2)_o(CHR^{61})_sR^{77}$ $-(CH_2)_o(CHR^{61})_sOR^{55}$; $-(CH_2)_o(CHR^{61})_sSR^{56}$; $-(CH_2)_o(CHR^{61})NR^{33}R^{34}$; $-(CH_2)_o(CHR^{61})_sOCONR^{33}R^{75}$; $-(CH_2)_o(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sCOR^{64}$;

$R^9$ is alkyl; alkenyl; $-(CH_2)_o(CHR^{61})_sOR^{55}$; $-(CH_2)_o(CHR^{61})_sSR^{56}$; $-(CH_2)_o(CHR^{61})_sNR^{33}R^{34}$; $-(CH_2)_o(CHR^{61})_sOCONR^{33}R^{75}$; $-(CH_2)_o(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;

$R^{10}$ is alkyl; alkenyl; $-(CH_2)_o(CHR^{61})_sOR^{55}$; $-(CH_2)_o(CHR^{61})_sSR^{56}$; $-(CH_2)_o(CHR^{61})_sNR^{33}R^{34}$; $-(CH_2)_o(CHR^{61})_sOCONR^{33}R^{75}$; $-(CH_2)_o(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;

$R^{11}$ is H; alkyl; alkenyl; $-(CH_2)_m(CHR^{61})_sOR^{55}$; $-(CH_2)_m(CHR^{61})_sNR^{33}R^{34}$; $-(CH_2)_m(CHR^{61})_sOCONR^{33}R^{75}$; $-(CH_2)_m(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;

$R^{12}$ is H; alkyl; alkenyl; $-(CH_2)_m(CHR^{61})_sOR^{55}$; $-(CH_2)_m(CHR^{61})_sSR^{56}$; $-(CH_2)_m(CHR^{61})_sNR^{33}R^{34}$; $-(CH_2)_m(CHR^{61})_sOCONR^{33}R^{75}$; $-(CH_2)_m(CHR^{61})_sNR^{20}CONR^{33}R^{82}$; $-(CH_2)_r(CHR^{61})_sCOOR^{57}$; $-(CH_2)_r(CHR^{61})_sCONR^{58}R^{59}$; $-(CH_2)_r(CHR^{61})_sPO(OR^{60})_2$; $-(CH_2)_r(CHR^{61})_sSO_2R^{62}$; or $-(CH_2)_r(CHR^{61})_sC_6H_4R^8$;

$R^{13}$ is alkyl; alkenyl; $-(CH_2)_q(CHR^{61})_sOR^{55}$; $-(CH_2)_q(CHR^{61})_sSR^{56}$; $-(CH_2)_q(CHR^{61})_sNR^{33}R^{34}$; $-(CH_2)_q(CHR^{61})_sOCONR^{33}R^{75}$; $-(CH_2)_q(CHR^{61})_sNR^{20}CONR^{33}R^{82}$; $-(CH_2)_q(CHR^{61})_sCOOR^{57}$; $-(CH_2)_q(CHR^{61})_sCONR^{58}R^{59}$; $-(CH_2)_q(CHR^{61})_sPO(OR^{60})_2$; $-(CH_2)_q(CHR^{61})_sSO_2R^{62}$; or $-(CH_2)_q(CHR^{61})_sC_6H_4R^8$;

$R^{14}$ is H; alkyl; alkenyl; $-(CH_2)_m(CHR^{61})_sOR^{55}$; $-(CH_2)_m(CHR^{61})_sNR^{33}R^{34}$; $-(CH_2)_m(CHR^{61})_sOCONR^{33}R^{75}$; $-(CH_2)_m(CHR^{61})_sNR^{20}CONR^{33}R^{82}$; $-(CH_2)_q(CHR^{61})_sCOOR^{57}$; $-(CH_2)_q(CHR^{61})_sCONR^{58}R^{59}$; $-(CH_2)_q(CHR^{61})_sPO(OR^{60})_2$; $-(CH_2)_q(CHR^{61})_sSOR^{62}$; or $-(CH_2)_q(CHR^{61})_sC_6H_4R^8$;

$R^{15}$ is alkyl; alkenyl; $-(CH_2)_o(CHR^{61})_sOR^{55}$; $-(CH_2)_o(CHR^{61})_sSR^{56}$; $-(CH_2)_o(CHR^{61})_sNR^{33}R^{34}$; $-(CH_2)_o(CHR^{61})_sOCONR^{33}R^{75}$; $-(CH_2)_o(CHR^{61})_sNR^{20}CONR^{33}R^{82}$; $-(CH_2)_o(CHR^{61})_sCOOR^{57}$; $-(CH_2)_o $(CHR^{61})_s CONR^{58}R^{59}$; —$(CH_2)_o(CHR^{61})_s PO(OR^{60})_2$; —$(CH_2)_o(CHR^{61})_s SO_2R^{62}$; or —$(CH_2)_o(CHR^{61})_s C_6H_4R^8$;

$R^{16}$ is alkyl; alkenyl; —$(CH_2)_o(CHR^{61})_s OR^{55}$; —$(CH_2)_o(CHR^{61})_s SR^{56}$; —$(CH_2)_o(CHR^{61})_s NR^{33}R^{34}$; —$(CH_2)_o(CHR^{61})_s OCONR^{33}R^{75}$; —$(CH_2)_o(CHR^{61})_s NR^{20}CONR^{33}R^{82}$; —$(CH_2)_o(CHR^{61})_s COOR^{57}$; —$(CH_2)_o(CHR^{61})_s CONR^{58}R^{59}$; —$(CH_2)_o(CHR^{61})_s PO(OR^{60})_2$; —$(CH_2)_o(CHR^{61})_s SO_2R^{62}$; or —$(CH_2)_o(CHR^{61})_s C_6H_4R^8$;

$R^{17}$ is alkyl; alkenyl; —$(CH_2)_q(CHR^{61})_s OR^{55}$; —$(CH_2)_q(CHR^{61})_s SR^{56}$; —$(CH_2)_q(CHR^{61})_s NR^{33}R^{34}$; —$(CH_2)_q(CHR^{61})_s OCONR^{33}R^{75}$; —$(CH_2)_q(CHR^{61})_s NR^{20}CONR^{33}R^{82}$; —$(CH_2)_q(CHR^{61})_s COOR^{57}$; —$(CH_2)_q(CHR^{61})_s CONR^{58}R^{59}$; —$(CH_2)_q(CHR^{61})_s PO(OR^{60})_2$; —$(CH_2)_q(CHR^{61})_s SO_2R^{62}$; or —$(CH_2)_q(CHR^{61})_s C_6H_4R^8$;

$R^{18}$ is alkyl; alkenyl; —$(CH_2)_p(CHR^{61})_s OR^{55}$; —$(CH_2)_p(CHR^{61})_s SR^{56}$; —$(CH_2)_p(CHR^{61})_s NR^{33}R^{34}$; —$(CH_2)_p(CHR^{61})_s OCONR^{33}R^{75}$; —$(CH_2)_p(CHR^{61})_s NR^{20}CONR^{33}R^{82}$; —$(CH_2)_p(CHR^{61})_s COOR^{57}$; —$(CH_2)_p(CHR^{61})_s CONR^{58}R^{59}$; —$(CH_2)_p(CHR^{61})_s PO(OR^{60})_2$; —$(CH_2)_p(CHR^{61})_s SO_2R^{62}$; or —$(CH_2)_o(CHR^{61})_s C_6H_4R^8$;

$R^{19}$ is lower alkyl; —$(CH_2)_p(CHR^{61})_s OR^{55}$; —$(CH_2)_p(CHR^{61})_s SR^{56}$; —$(CH_2)_p(CHR^{61})_s NR^{33}R^{34}$; —$(CH_2)_p(CHR^{61})_s OCONR^{33}R^{75}$; —$(CH_2)_p(CHR^{61})_s NR^{20}CONR^{33}R^{82}$; —$(CH_2)_p(CHR^{61})_s COOR^{57}$; —$(CH_2)_p(CHR^{61})_s CONR^{58}R^{59}$; —$(CH_2)_p(CHR^{61})_s PO(OR^{60})_2$; —$(CH_2)_p(CHR^{61})_s SO_2R^{62}$; or —$(CH_2)_o(CHR^{61})_s C_6H_4R^8$; or $R^{18}$ and $R^{19}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{20}$ is H; alkyl; alkenyl; or aryl-lower alkyl;

$R^{21}$ is H; alkyl; alkenyl; —$(CH_2)_o(CHR^{61})_s OR^{55}$; —$(CH_2)_o(CHR^{61})_s SR^{56}$; —$(CH_2)_o(CHR^{61})_s NR^{33}R^{34}$; —$(CH_2)_o(CHR^{61})_s OCONR^{33}R^{75}$; —$(CH_2)_o(CHR^{61})_s NR^{20}CONR^{33}R^{82}$; —$(CH_2)_o(CHR^{61})_s COOR^{57}$; —$(CH_2)_o(CHR^{61})_s CONR^{58}R^{59}$; —$(CH_2)_o(CHR^{61})_s PO(OR^{60})_2$; —$(CH_2)_o(CHR^{61})_s SO_2R^{62}$; or —$(CH_2)_o(CHR^{61})_s C_6H_4R^8$;

$R^{22}$ is H; alkyl; alkenyl; —$(CH_2)_o(CHR^{61})_s OR^{55}$; —$(CH_2)_o(CHR^{61})_s SR^{56}$; —$(CH_2)_o(CHR^{61})_s NR^{33}R^{34}$; —$(CH_2)_o(CHR^{61})_s OCONR^{33}R^{75}$; —$(CH_2)_o(CHR^{61})_s NR^{20}CONR^{33}R^{82}$; —$(CH_2)_o(CHR^{61})_s COOR^{57}$; —$(CH_2)_o(CHR^{61})_s CONR^{58}R^{59}$; —$(CH_2)_o(CHR^{61})_s PO(OR^{60})_2$; —$(CH_2)_o(CHR^{61})_s SO_2R^{62}$; or —$(CH_2)_o(CHR^{61})_s C_6H_4R^8$;

$R^{23}$ is alkyl; alkenyl; —$(CH_2)_o(CHR^{61})_s OR^{55}$; —$(CH_2)_o(CHR^{61})_s SR^{56}$; —$(CH_2)_o(CHR^{61})_s NR^{33}R^{34}$; —$(CH_2)_o(CHR^{61})_s OCONR^{33}R^{75}$; —$(CH_2)_o(CHR^{61})_s NR^{20}CONR^{33}R^{82}$; —$(CH_2)_o(CHR^{61})_s COOR^{57}$; —$(CH_2)_o(CHR^{61})_s CONR^{58}R^{59}$; —$(CH_2)_o(CHR^{61})_s PO(OR^{60})_2$; —$(CH_2)_o(CHR^{61})_s SO_2R^{62}$; or —$(CH_2)_o(CHR^{61})_s C_6H_4R^8$;

$R^{24}$ is alkyl; alkenyl; —$(CH_2)_o(CHR^{61})_s OR^{55}$; —$(CH_2)_o(CHR^{61})_s SR^{56}$; —$(CH_2)_o(CHR^{61})_s NR^{33}R^{34}$; —$(CH_2)_o(CHR^{61})_s OCONR^{33}R^{75}$; —$(CH_2)_o(CHR^{61})_s NR^{20}CONR^{33}R^{82}$; —$(CH_2)_o(CHR^{61})_s COOR^{57}$; —$(CH_2)_o(CHR^{61})_s CONR^{58}R^{59}$; —$(CH_2)_o(CHR^{61})_s PO(OR^{60})_2$; —$(CH_2)_o(CHR^{61})_s SO_2R^{62}$; or —$(CH_2)_o(CHR^{61})_s C_6H_4R^8$;

$R^{25}$ is H; alkyl; alkenyl; —$(CH_2)_m(CHR^{61})_s OR^{55}$; —$(CH_2)_m(CHR^{61})_s SR^{56}$; —$(CH_2)_m(CHR^{61})_s NR^{33}R^{34}$; —$(CH_2)_m(CHR^{61})_s OCONR^{33}R^{75}$; —$(CH_2)_m(CHR^{61})_s NR^{20}CONR^{33}R^{82}$; —$(CH_2)_o(CHR^{61})_s COOR^{57}$; —$(CH_2)_o(CHR^{61})_s CONR^{58}R^{59}$; —$(CH_2)_o(CHR^{61})_s PO(OR^{60})_2$; —$(CH_2)_o(CHR^{61})_s SO_2R^{62}$; or —$(CH_2)_o(CHR^{61})_s C_6H_4R^8$;

$R^{26}$ is H; alkyl; alkenyl; —$(CH_2)_m(CHR^{61})_s OR^{55}$; —$(CH_2)_m(CHR^{61})_s SR^{56}$; —$(CH_2)_m(CHR^{61})_s NR^{33}R^{34}$; —$(CH_2)_m(CHR^{61})_s OCONR^{33}R^{75}$; —$(CH_2)_m(CHR^{61})_s NR^{20}CONR^{33}R^{82}$; —$(CH_2)_o(CHR^{61})_s COOR^{57}$; —$(CH_2)_o(CHR^{61})_s CONR^{58}R^{59}$; —$(CH_2)_o(CHR^{61})_s PO(OR^{60})_2$; —$(CH_2)_o(CHR^{61})_s SO_2R^{62}$; or —$(CH_2)_o(CHR^{61})_s C_6H_4R^8$; or $R^{25}$ and $R^{26}$ taken together can form: —$(CH_2)_{2-6}$—; —$(CH_2)_rO(CH_2)_r$—; —$(CH_2)_rS(CH_2)_r$—; or —$(CH_2)_rNR^{57}(CH_2)_r$—;

$R^{27}$ is H; alkyl; alkenyl; —$(CH_2)_o(CHR^{61})_s OR^{55}$; —$(CH_2)_o(CHR^{61})_s SR^{56}$; —$(CH_2)_o(CHR^{61})_s NR^{33}R^{34}$; —$(CH_2)_o(CHR^{61})_s COOR^{57}$; —$(CH_2)_o(CHR^{61})_s CONR^{58}R^{59}$; —$(CH_2)_o(CHR^{61})_s OCONR^{33}R^{75}$; —$(CH_2)_o(CHR^{61})_s NR^{20}CONR^{33}R^{82}$; —$(CH_2)_o(CHR^{61})_s PO(OR^{60})_2$; —$(CH_2)_o(CHR^{61})_s SO_2R^{62}$; or —$(CH_2)_o(CHR^{61})_s C_6H_4R^8$;

$R^{28}$ is alkyl; alkenyl; —$(CH_2)_o(CHR^{61})_s$—$OR^{55}$; —$(CH_2)_o(CHR^{61})_s$ $SR^{56}$; —$(CH_2)_o(CHR^{61})_s NR^{33}R^{34}$; —$(CH_2)_o(CHR^{61})_s OCONR^{33}R^{75}$; —$(CH_2)_o(CHR^{61})_s NR^{20}CONR^{33}R^{82}$; —$(CH_2)_o(CHR^{61})_s COOR^{52}$; —$(CH_2)_o(CHR^{61})_s CONR^{58}R^{59}$; —$(CH_2)_o(CHR^{61})_s PO(OR^{60})_2$; —$(CH_2)_o(CHR^{61})_s SO_2R^{62}$; or —$(CH_2)_o(CHR^{61})_s C_6H_4R^8$;

$R^{29}$ is alkyl; alkenyl; —$(CH_2)_o(CHR^{61})_s OR^{55}$; —$(CH_2)_o(CHR^{61})_s SR^{56}$; —$(CH_2)_o(CHR^{61})_s NR^{33}R^{34}$; —$(CH_2)_o(CHR^{61})_s OCONR^{33}R^{75}$; —$(CH_2)_o(CHR^{61})_s NR^{20}CONR^{33}R^{82}$; —$(CH_2)_o(CHR^{61})_s COOR^{52}$; —$(CH_2)_o(CHR^{61})_s CONR^{58}R^{59}$; —$(CH_2)_o(CHR^{61})_s PO(OR^{60})_2$; —$(CH_2)_o(CHR^{61})_s SO_2R^{62}$; or —$(CH_2)_o(CHR^{61})_s C_6H_4R^8$;

$R^{33}$ is H; alkyl, alkenyl; —$(CH_2)_m(CHR^{61})_s OR^{55}$; —$(CH_2)_m(CHR^{61})_s NR^{34}R^{63}$; —$(CH_2)_m(CHR^{61})_s OCONR^{75}R^{82}$; —$(CH_2)_m(CHR^{61})_s NR^{20}CONR^{78}R^{82}$; —$(CH_2)_o(CHR^{61})_s COR^{64}$; —$(CH_2)_o(CHR^{61})_s$—$CONR^{58}R^{59}$, —$(CH_2)_o(CHR^{61})_s PO(OR^{60})_2$; —$(CH_2)_o(CHR^{61})_s SO_2R^{62}$; or —$(CH_2)_o(CHR^{61})_s C_6H_4R^8$;

$R^{34}$ is H; lower alkyl; aryl, or aryl-lower alkyl; or $R^{33}$ and $R^{34}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{50}$ is H; lower alkyl; or aryl-lower alkyl;

$R^{55}$ is H; lower alkyl; lower alkenyl; aryl-lower alkyl; —$(CH_2)_m(CHR^{61})_s OR^{52}$; —$(CH_2)_m(CHR^{61})_s NR^{34}R^{63}$; —$(CH_2)_m(CHR^{61})_s OCONR^{75}R^{82}$; —$(CH_2)_m(CHR^{61})_s NR^{20}CONR^{78}R^{82}$; —$(CH_2)_o(CHR^{61})_s$—$COR^{64}$; —$(CH_2)_o(CHR^{61})COOR^{57}$; or —$(CH_2)_o(CHR^{61})_s CONR^{58}R^{59}$;

$R^{56}$ is H; lower alkyl; lower alkenyl; aryl-lower alkyl; —$(CH_2)_m(CHR^{61})_s OR^{57}$; —$(CH_2)_m(CHR^{61})_s NR^{34}R^{63}$; —$(CH_2)_m(CHR^{61})_s OCONR^{75}R^{82}$; —$(CH_2)_m(CHR^{61})_s NR^{20}CONR^{78}R^{82}$; —$(CH_2)_o(CHR^{61})_s$—$COR^{64}$; or —$(CH_2)_o(CHR^{61})_s CONR^{58}R^{59}$;

$R^{57}$ is H; lower alkyl; lower alkenyl; aryl lower alkyl; or heteroaryl lower alkyl;

$R^{58}$ is H; lower alkyl; lower alkenyl; aryl; heteroaryl; aryl-lower alkyl; or heteroaryl-lower alkyl;

$R^{59}$ is H; lower alkyl; lower alkenyl; aryl; heteroaryl; aryl-lower alkyl; or heteroaryl-lower alkyl; or $R^{58}$ and $R^{59}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{60}$ is H; lower alkyl; lower alkenyl; aryl; or aryl-lower alkyl;

$R^{61}$ is alkyl; alkenyl; aryl; heteroaryl; aryl-lower alkyl; heteroaryl-lower alkyl; —$(CH_2)_pOR^{55}$; —$(CH_2)_pNR^{33}R^{34}$; —$(CH_2)_pOCONR^{75}R^{82}$; —$(CH_2)_pNR^{20}CONR^{78}R^{82}$; —$(CH_2)_oCOOR^{37}$; or —$(CH_2)_oPO(OR^{60})_2$;

$R^{62}$ is lower alkyl; lower alkenyl; aryl, heteroaryl; or aryl-lower alkyl;

$R^{63}$ is H; lower alkyl; lower alkenyl; aryl, heteroaryl; aryl-lower alkyl; heteroaryl-lower alkyl; —$COR^{64}$; —$COOR^{57}$; —$CONR^{58}R^{58}$; —$SO_2R^{62}$; or —$PO(OR^{60})_2$; or $R^{34}$ and $R^{63}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{64}$ is H; lower alkyl; lower alkenyl; aryl; heteroaryl; aryl-lower alkyl; heteroaryl-lower alkyl; —$(CH_2)_p(CHR^{61})_sOR^{65}$; —$(CH_2)_p(CHR^{61})_sSR^{66}$; —$(CH_2)_p(CHR^{61})_sNR^{34}R^{63}$; —$(CH_2)_p(CHR^{61})_sOCONR^{75}R^{82}$; or —$(CH_2)_p(CHR^{61})_sNR^{20}CONR^{78}R^{82}$;

$R^{65}$ is H; lower alkyl; lower alkenyl; aryl, aryl-lower alkyl; heteroaryl-lower alkyl; —$COR^{57}$; —$COOR^{57}$; or —$CONR^{58}R^{59}$;

$R^{66}$ is H; lower alkyl; lower alkenyl; aryl; aryl-lower alkyl; heteroaryl-lower alkyl; or —$CONR^{58}R^{59}$;

$R^{67}$ is H; Cl; Br; F; $NO_2$; —$NR^{34}COR^{57}$; —$CF_3$; CN; —$OCF_3$; —$OCHF_2$; —$OR^{57}$; —$SR^{62}$; lower alkyl; or lower alkenyl;

$R^{68}$ is H; Cl; Br; F; $NO_2$; —$NR^{34}COR^{57}$; —$CF_3$; CN; —$OCF_3$; —$OCHF_2$; —$OR^{57}$; —$SR^{62}$; lower alkyl; or lower alkenyl;

$R^{69}$ is H; Cl; Br; F; $NO_2$; —$NR^{34}COR^{57}$; —$CF_3$; CN; —$OCF_3$; —$OCHF_2$; —$OR^{57}$; —$SR^{62}$; lower alkyl; or lower alkenyl;

$R^{70}$ is H; Cl; Br; F; $NO_2$; —$NR^{34}COR^{57}$; —$CF_3$; CN; —$OCF_3$; —$OCHF_2$; —$OR^{57}$; —$SR^{62}$; lower alkyl; or lower alkenyl;

$R^{71}$ is lower alkyl; lower alkenyl; —$(CH_2)_p(CHR^{61})_sOR^{75}$; —$(CH_2)_p(CHR^{61})_sSR^{75}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{75}$; —$(CH_2)_pCONR^{58}R^{59}$; —$(CH_2)_pPO(OR^{62})_2$; —$(CH_2)_pSO_2R^{62}$; or —$(CH_2)_o$—$C_6R^{67}R^{68}R^{69}R^{70}R^{76}$;

$R^{72}$ is alkyl; alkenyl; —$(CH_2)_p(CHR^{61})_sOR^{85}$; or —$(CH_2)_p(CHR^{61})_sSR^{85}$;

$R^{73}$ is —$(CH_2)_oR^{77}$; —$(CH_2)_oO(CH_2)_oR^{77}$; —$(CH_2)_rS(CH_2)_oR^{77}$; or —$(CH_2)_rNR^{20}(CH_2)_oR^{77}$;

$R^{74}$ is —$(CH_2)_pNR^{78}R^{79}$; —$(CH_2)_pNR^{77}R^{80}$; —$(CH_2)_pC(=NR^{80})NR^{78}R^{79}$; —$(CH_2)_pC(=NOR^{50})NR^{78}R^{79}$; —$(CH_2)_pC(=NNR^{78}R^{79})NR^{78}R^{79}$; —$(CH_2)_pNR^{80}C(=NR^{80})NR^{78}R^{79}$; —$(CH_2)_pN=C(NR^{78}R^{80})NR^{79}R^{80}$; —$(CH_2)_pC_6H_4NR^{78}R^{79}$; —$(CH_2)_pC_6H_4NR^{77}R^{80}$; —$(CH_2)_pC_6H_4C(=NR^{80})NR^{78}R^{79}$; —$(CH_2)_pC_6H_4C(=NOR^{50})NR^{78}R^{79}$; —$(CH_2)_pC_6H_4C(=NNR^{78}R^{79})NR^{78}R^{79}$; —$(CH_2)_pC_6H_4NR^{80}C(=NR^{80})NR^{78}R^{79}$; —$(CH_2)_pC_6H_4N=C(NR^{78}R^{80})NR^{79}R^{80}$; —$(CH_2)_rO(CH_2)_mNR^{78}R^{79}$; —$(CH_2)_rO(CH_2)_mNR^{77}R^{80}$; —$(CH_2)_rO(CH_2)_pC(=NR^{80})NR^{78}R^{79}$; —$(CH_2)_rO(CH_2)_pC(=NOR^{50})NR^{78}R^{79}$; —$(CH_2)_rO(CH_2)_pC(=NNR^{78}R^{79})NR^{78}R^{79}$; —$(CH_2)_rO(CH_2)_mNR^{80}C(=NR^{80})NR^{78}R^{79}$; —$(CH_2)_rO(CH_2)_mN=C(NR^{78}R^{80})NR^{79}R^{80}$; —$(CH_2)_rO(CH_2)_pC_6H_4CNR^{78}R^{79}$; —$(CH_2)_rO(CH_2)_pC_6H_4C(=NR^{80})NR^{78}R^{79}$; —$(CH_2)_rO(CH_2)_pC_6H_4C(=NOR^{50})NR^{78}R^{79}$; —$(CH_2)_rO(CH_2)_pC_6H_4C(=NNR^{78}R^{79})NR^{78}R^{79}$; —$(CH_2)_rO(CH_2)_pC_6H_4NR^{80}C(=NR^{80})NR^{78}R^{79}$; —$(CH_2)_rS(CH_2)_mNR^{78}R^{79}$; —$(CH_2)_rS(CH_2)_mNR^{77}R^{80}$; —$(CH_2)_rS(CH_2)_pC(=NR^{80})NR^{78}R^{79}$; —$(CH_2)_rS(CH_2)_pC(=NOR^{50})NR^{78}R^{79}$; —$(CH_2)_rS(CH_2)_pC(=NNR^{78}R^{79})NR^{78}R^{79}$; —$(CH_2)_rS(CH_2)_mNR^{80}C(=NR^{80})NR^{78}R^{79}$; —$(CH_2)_rS(CH_2)_mN=C(NR^{78}R^{80})NR^{78}R^{80}$; —$(CH_2)_rS(CH_2)_pC_6H_4CNR^{78}R^{79}$; —$(CH_2)_rS(CH_2)_pC_6H_4C(=NR^{80})NR^{78}R^{79}$; —$(CH_2)_rS(CH_2)_pC_6H_4C(=NOR^{50})NR^{78}R^{79}$; —$(CH_2)_rS(CH_2)_pC_6H_4C(=NNR^{78}R^{79})NR^{78}R^{79}$; —$(CH_2)_rS(CH_2)_pC_6H_4NR^{80}C(=NR^{80})NR^{78}R^{79}$; —$(CH_2)_pNR^{80}COR^{64}$; —$(CH_2)_pNR^{80}COR^{77}$; —$(CH_2)_pNR^{80}CONR^{78}R^{79}$; or —$(CH_2)_pC_6H_4NR^{80}CONR^{78}R^{79}$;

$R^{75}$ is lower alkyl; lower alkenyl; or aryl-lower alkyl; or $R^{33}$ and $R^{75}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; or $R^{75}$ and $R^{82}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{76}$ is H; lower alkyl; lower alkenyl; aryl-lower alkyl; —$(CH_2)_oOR^{72}$; —$(CH_2)_oSR^{72}$; —$(CH_2)_oNR^{33}R^{34}$; —$(CH_2)_oOCONR^{33}R^{75}$; —$(CH_2)_oNR^{20}CONR^{33}R^{81}$; —$(CH_2)_oCOOR^{75}$; —$(CH_2)_oCONR^{58}R^{59}$; —$(CH_2)_pPO(OR^{60})_2$; —$(CH_2)_pSO_2R^{62}$; or —$(CH_2)_oCOR^{64}$;

$R^{77}$ is —$C_6R^{67}R^{68}R^{69}R^{70}R^{76}$ with the proviso that at least two of $R^{67}$, $R^{68}$, $R^{69}$ and $R^{70}$ are H; or a heteroaryl group of one of the formulae

H1

H2

H3

H4

H5

H6

H7

-continued
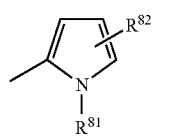
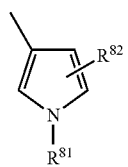
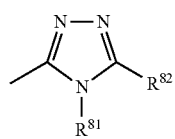
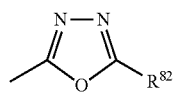
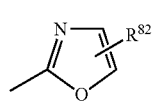
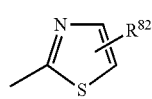
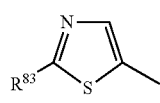
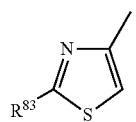
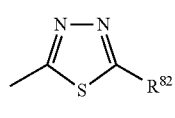
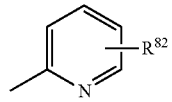
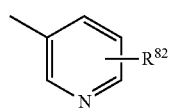
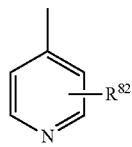
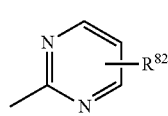
-continued
H8
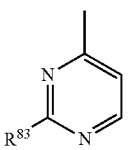
H9
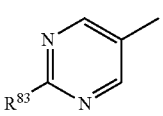
H10
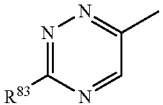
H11
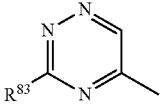
H12
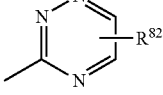
H13
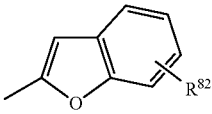
H14
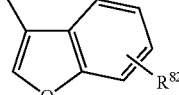
H15
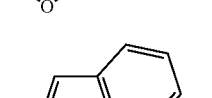
H16
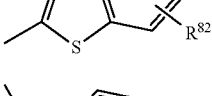
H17
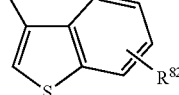
H18
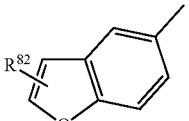
H19
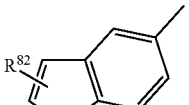
H20
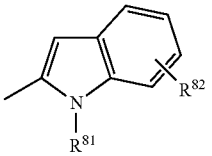

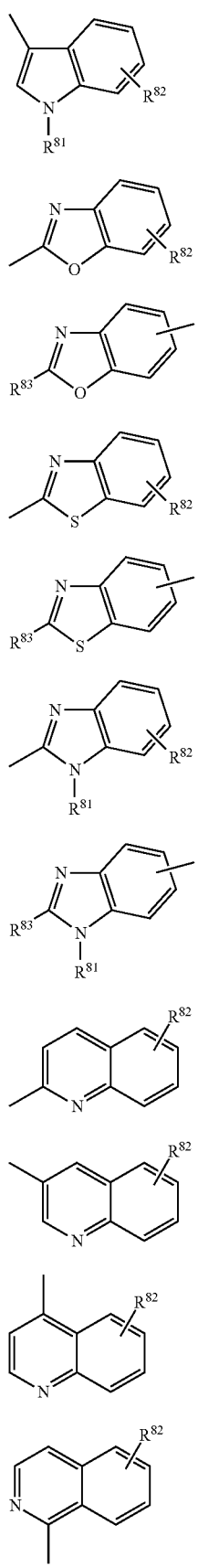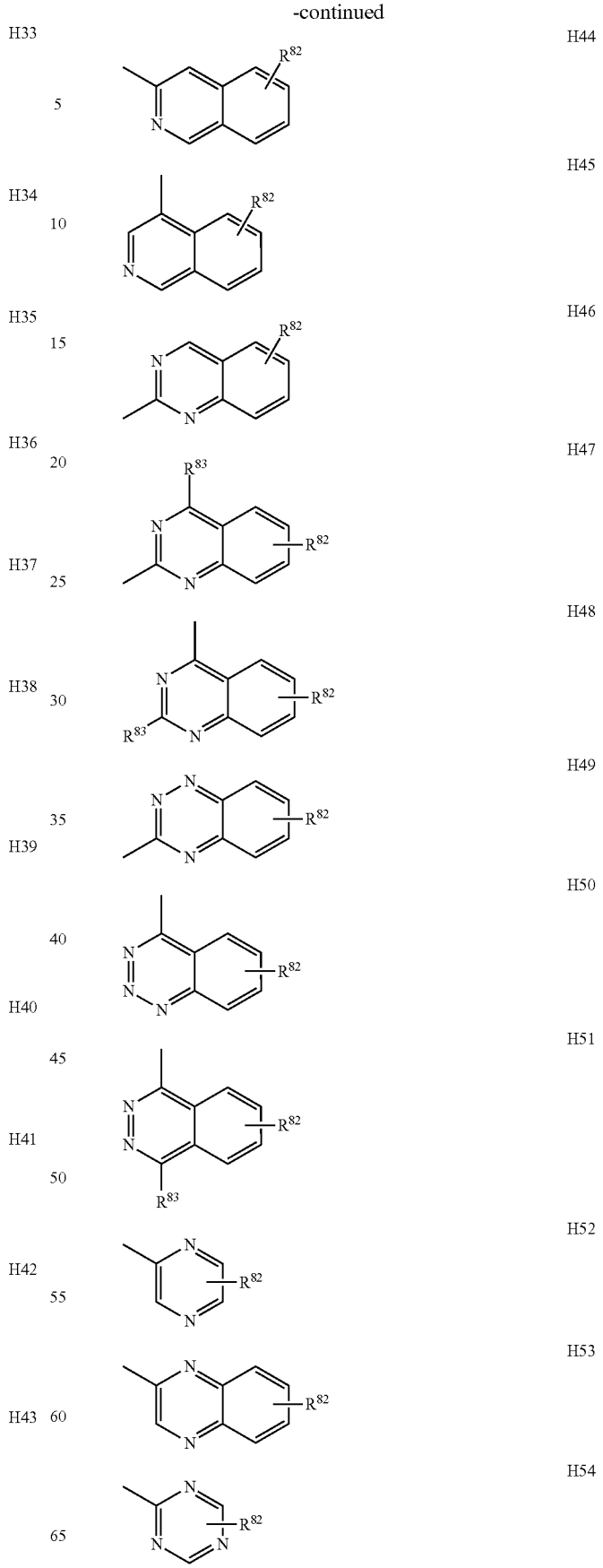

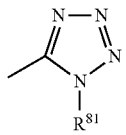
H55

R⁷⁸ is H; lower alkyl; aryl; or aryl-lower alkyl; or
R⁷⁸ and R⁸² taken together can form: —(CH₂)₂₋₆—; —(CH₂)₂O(CH₂)₂—; —(CH₂)₂S(CH₂)₂—; or —(CH₂)₂NR⁵⁷(CH₂)₂—;
R⁷⁹ is H; lower alkyl; aryl; or aryl-lower alkyl; or
R⁷⁸ and R⁷⁹, taken together, can be —(CH₂)₂₋₇—; —(CH₂)₂O(CH₂)₂—; or —(CH₂)₂NR⁵⁷(CH₂)₂—;
R⁸⁰ is H; or lower alkyl;
R⁸¹ is H; lower alkyl; or aryl-lower alkyl; or
R³³ and R⁸¹ taken together can form: —(CH₂)₂₋₆—; —(CH₂)₂O(CH₂)₂—; —(CH₂)₂S(CH₂)₂—; or —(CH₂)₂NR⁵⁷(CH₂)₂—;
R⁸² is H; —CF₃; —OCF₃; —OCHF₂; lower alkyl; aryl; heteroaryl; or aryl-lower alkyl;
R⁸³ is H; lower alkyl; aryl; or —NR⁷⁸R⁷⁹;
R⁸⁴ is —(CH₂)ₚ(CHR⁶¹)ₛOH; —(CH₂)ₚCOOR⁸⁰; —(CH₂)ₚ(CHR⁶¹)ₛSH; —(CH₂)ₚCONR⁷⁸R⁷⁹; —(CH₂)ₚNR⁸⁰CONR⁷⁸R⁷⁹; —(CH₂)ₚC₆H₄CONR⁷⁸R⁷⁹; or —(CH₂)ₚC₆H₄NR⁸⁰CONR⁷⁸R⁷⁹;
R⁸⁵ is lower alkyl; or lower alkenyl;
R⁸⁶ is R⁷⁴; —(CH₂)ₒR⁷⁷; —(CH₂)ₒ—CHR³³R⁷⁵; R⁸⁴; —[(CH₂)ᵤ—X'ₜ—(CH₂)ᵥNR⁷⁸R⁷⁹; —[(CH₂)ᵤ—X'ₜ—(CH₂)ᵥ—C(=NR⁸⁰)NR⁷⁸R⁷⁹; —[(CH₂)ᵤ—X'ₜ—(CH₂)ᵥOR⁷⁸; —[(CH₂)ᵤ—X'ₜ—(CH₂)ᵥ—CONR⁷⁸R⁷⁹; —[(CH₂)ᵤ—X'ₜ—(CH₂)ᵥ—NR⁸⁰CONR⁷⁸R⁷⁹; —[(CH₂)ᵤ—X'ₜ—(CH₂)ᵥSR⁷⁸ where X' is —O—, —NR20—, —S—; or —OCOO—, u is 1-3, t is 1-6, and v is 1-3;

m is 2-4; o is 0-4; p is 1-4; q is 0-2; r is 1 or 2; s is 0 or 1;
the amino acid residue of type C is a residue of formula —NR²⁰CH(R⁷²)CO—;
the amino acid residue of type D is a residue of formula —NR²⁰CH(R⁷³)CO—;
the amino acid residue of type E is a residue of the formula —NR²⁰CH(R⁷⁴)CO—;
the amino acid residue of type F is a residue of the formula —NR²⁰CH(R⁸⁴)CO—;
the N-substituted glycine residue of type I is a residue of formula —NR⁸⁶CH₂CO—;
the amino acid residue of type M is a residue of formulae —NR²⁰CH(R⁷²)(CH₂)₂CO—; —NR²⁰CH(R⁷³)(CH₂)₂CO—; —NR²⁰CH(R⁷⁴)(CH₂)₂CO—; or —NR²⁰CH(R⁸⁴)(CH₂)₂CO—,
the amino acid residue of type N is a residue of formulae —NR²⁰CH(R⁷²)(CH₂)CO—; —NR²⁰CH(R⁷³)(CH₂)CO—; —NR²⁰CH(R⁷⁴)(CH₂)CO—, or —NR²CH(R⁸⁴)(CH₂)CO—;
and pharmaceutically acceptable salts thereof.

In accordance with the present invention these β-hairpin peptidomimetics can be prepared by a process which comprises
(a) coupling an appropriately functionalized solid support with an appropriately N-protected derivative of that amino acid which in the desired end-product corresponds to Xaaⁿ, wherein n is 16, 8, 7, 6, or 3, any functional group which may be present in said N-protected amino acid derivative being likewise appropriately protected;
(b) removing the N-protecting group from the product thus obtained;
(c) coupling the product thus obtained with an appropriately N-protected derivative of that amino acid which in the desired end-product corresponds to Xaaⁿ⁻¹, any functional group which may be present in said N-protected amino acid derivative being likewise appropriately protected;
(d) removing the N-protecting group from the product obtained in step (c);
(e) effecting steps substantially corresponding to steps (c) and (d) using appropriately N-protected derivatives of amino acids which in the desired end-product are in positions n−2 to 1, any functional group(s) which may be present in said N-protected amino acid derivatives being likewise appropriately protected;
(f) if n is not 16, further effecting steps substantially corresponding to steps (c) and (d) using appropriately N-protected derivatives of amino acids which in the desired end-product are in positions 16 to n+1, any functional group(s) which may be present in said N-protected amino acid derivatives being likewise appropriately protected;
(g) forming an interstrand linkage between side-chains of Cys at positions P4 and P11; or alternatively, forming the aforesaid linkage subsequent to step (j), as described herein below;
(h) detaching the product thus obtained from the solid support;
(i) cyclizing the product cleaved from the solid support;
(j) removing any protecting groups present on functional groups of any members of the chain of amino acid residues and, if desired, any protecting group(s) which may in addition be present in the molecule; and
(k) if desired, converting the product thus obtained into a pharmaceutically acceptable salt or converting a pharmaceutically acceptable, or unacceptable, salt thus obtained into the corresponding free compound or into a different, pharmaceutically acceptable, salt.

As used in this description, the term "alkyl", taken alone or in combinations, designates saturated, straight-chain or branched hydrocarbon radicals having up to 24, preferably up to 12, carbon atoms. Similarly, the term "alkenyl" designates straight chain or branched hydrocarbon radicals having up to 24, preferably up to 12, carbon atoms and containing at least one or, depending on the chain length, up to four olefinic double bonds. The term "lower" designates radicals and compounds having up to 6 carbon atoms. Thus, for example, the term "lower alkyl" designates saturated, straight-chain, or branched hydrocarbon radicals having up to 6 carbon atoms, such as methyl, ethyl, n-propyl, isopropyl, n-butyl, sec.-butyl, isobutyl, tert.-butyl, and the like. Similarly, the term "lower cycloalkyl" designates saturated cyclic hydrocarbon radicals having up to 6 carbon atoms, such as cyclopentyl, cyclohexyl and the like. The term "aryl" designates aromatic carbocyclic hydrocarbon radicals containing one or two six-membered rings, such as phenyl or naphthyl, which may be substituted by up to three substituents such as Br, Cl, F, CF₃, NO₂, lower alkyl or lower alkenyl. The term "heteroaryl" designates aromatic heterocyclic radicals containing one or two five- and/or six-membered rings, at least one of them containing up to three heteroatoms selected from the group consisting of O, S and N and said ring(s) being optionally substituted; representative examples of such optionally substituted heteroaryl radicals are indicated hereinabove in connection with the definition of R⁷⁷.

The β-hairpin conformation of Cyclo (-Xaa¹-Xaa²-Xaa³-Cys⁴-Xaa⁵-Xaa⁶-Xaa⁷-Xaa⁸-Arg⁹-Tyr¹⁰-Cys¹¹-Xaa¹²-Xaa¹³-Xaa¹⁴-Xaa¹⁵-Xaa¹⁶-), disulfide bond between Cys⁴ and Cys¹¹, is highly relevant for the CXCR4 antagonizing activity of the β-hairpin mimetics of the present invention.

The β-hairpin stabilizing conformational properties induced by the D-amino acid residue Xaa$^7$ and the D-amino acid or N-substituted glycine residue Xaa$^{15}$ and fostered by the conserved amino acids at positions 4, 9, 10 and 11 within the sequence play a key role not only for the selective antagonizing activity but also for the synthesis process defined hereinabove, as incorporation of aforesaid residues Xaa$^7$ and Xaa$^{15}$ near the beginning or near the middle of the linear protected peptide precursors enhances cyclization yields significantly.

Building blocks A1-A69 and A105 of the structural element -A-CO— belong to a class of amino acids wherein the N-terminus is a secondary amine forming part of a ring. Among the genetically encoded amino acids only proline falls into this class. The configuration of building block A1 through A69 and A105 is (D), and they can be combined with a building block —B—CO— of (L)-configuration. Preferred combinations are -$^D$A1-CO—$^L$B—CO— to -$^D$A69-CO—$^L$B—CO— and -$^D$A105-CO—$^L$B—CO—. Thus, for example, $^D$Pro-$^L$Pro constitutes the prototype of such a combination.

It will be appreciated that building blocks -A1-CO— to -A69-CO— and A105-CO— in which A has (D)-configuration, are carrying a group R$^1$ at the β-position to the N-terminus. The preferred values for R$^1$ are H and lower alkyl with the most preferred values for R$^1$ being H and methyl. It will be recognized by those skilled in the art, that A1-A69 and A105 are shown in (D)-configuration which, for R$^1$ being H and methyl, corresponds to the (R)-configuration. Depending on the priority of other values for R$^1$ according to the Cahn, Ingold and Prelog rules, this configuration may also have to be expressed as (S).

In addition to R$^1$ building blocks -A1-CO— to -A69-CO— and A105-CO— can carry an additional substituent designated as R$^2$ to R$^{17}$. This additional substituent can be H, and if it is other than H, it is preferably a small to medium-sized aliphatic or aromatic group. Examples of preferred values for R$^1$ to R$^{17}$ are:

—R$^1$ is hydrogen or lower alkyl;
—R$^2$ is H; lower alkyl; lower alkenyl;
  —(CH$_2$)$_p$OR$^{55}$ (where R$^{55}$: lower alkyl; or lower alkenyl);
  —(CH$_2$)$_p$SR$^{56}$ (where R$^{56}$: lower alkyl; or lower alkenyl);
  —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl));
  —(CH$_2$)$_p$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—); —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl));
  —(CH$_2$)$_p$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—;
  —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl));
  —(CH$_2$)$_o$N(R$^{20}$)COR$^{64}$ (where R$^{20}$: H; or lower alkyl; R$^{64}$: lower alkyl; or lower alkenyl);
  —(CH$_2$)$_o$COOR$^{57}$ (where R$^{57}$: lower alkyl; or lower alkenyl);
  —(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—;
  —(CH$_2$)$_2$S(CH$_2$)$_2$—; or —(CH$_2$)$_2$NR$^{57}$(CH$_2$)$_2$— (where R$^{57}$: H; or lower alkyl));
  —(CH$_2$)$_o$PO(OR$^{60}$)$_2$ (where R$^{60}$: H; lower alkyl; or lower alkenyl);
  —(CH$_2$)$_o$SO$_2$R$^{62}$ (where R$^{62}$: lower alkyl; or lower alkenyl);
  —(CH$_2$)$_q$C$_6$H$_4$R$^8$ (where R$^8$: H; F; Cl; CF$_3$; lower alkyl; lower alkenyl; or lower alkoxy); or
  —(CH$_2$)$_q$CN$_4$R$^{81}$.
—R$^3$ is H; lower alkyl; lower alkenyl;
  —(CH$_2$)$_m$OR$^{55}$ (where R$^{55}$: lower alkyl; or lower alkenyl);
  —(CH$_2$)$_m$SR$^{56}$ (where R$^{56}$: lower alkyl; or lower alkenyl);
  —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; (CH$_2$)$_2$O(CH$_2$)$_2$—;
  —(CH$_2$)$_2$S(CH$_2$)$_2$—; or —(CH$_2$)$_2$NR$^{57}$(CH$_2$)$_2$— (where R$^{57}$: H; or lower alkyl));
  —(CH$_2$)$_m$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—;
  —(CH$_2$)$_2$S(CH$_2$)$_2$—; or —(CH$_2$)$_2$NR$^{57}$(CH$_2$)$_2$— (where R$^{57}$: H; or lower alkyl));
  —(CH$_2$)$_m$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—;
  —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl));
  —(CH$_2$)$_o$N(R$^{20}$)COR$^{64}$ (where R$^{20}$: H; or lower alkyl; R$^{64}$: lower alkyl; or lower alkenyl);
  —(CH$_2$)$_o$COOR$^{57}$ (where R$^{57}$: lower alkyl; or lower alkenyl);
  —(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—;
  —(CH$_2$)$_2$S(CH$_2$)$_2$—; or —(CH$_2$)$_2$NR$^{57}$(CH$_2$)$_2$— (where R$^{57}$: H; or lower alkyl));
  —(CH$_2$)$_o$PO(OR$^{60}$)$_2$ (where R$^{60}$: H; lower alkyl; or lower alkenyl);
  —(CH$_2$)$_o$SO$_2$R$^{62}$ (where R$^{62}$: lower alkyl; or lower alkenyl); or
  —(CH$_2$)$_q$C$_6$H$_4$R$^8$ (where R$^8$: H; F; Cl; CF$_3$; lower alkyl; lower alkenyl; or lower alkoxy).
—R$^4$ is H; lower alkyl; lower alkenyl;
  —(CH$_2$)$_m$OR$^{55}$ (where R$^{55}$: lower alkyl; or lower alkenyl);
  —(CH$_2$)$_m$SR$^{56}$ (where R$^{56}$: lower alkyl; or lower alkenyl);
  —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—;
  —(CH$_2$)$_2$S(CH$_2$)$_2$—; or —(CH$_2$)$_2$NR$^{57}$(CH$_2$)$_2$— (where R$^{57}$: H; or lower alkyl));
  —(CH$_2$)$_m$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—;
  —(CH$_2$)$_2$S(CH$_2$)$_2$—; or —(CH$_2$)$_2$NR$^{57}$(CH$_2$)$_2$— (where R$^{57}$: H; or lower alkyl));
  —(CH$_2$)$_m$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form:
  —(CH$_2$)$_{2-6}$—;

—$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
—$(CH_2)_mN(R^{20})COR^{64}$ (where $R^{20}$: H; or lower alkyl; $R^{64}$: lower alkyl; or lower alkenyl);
—$(CH_2)_oCOOR^{57}$ (where $R^{57}$: lower alkyl; or lower alkenyl);
—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
—$(CH_2)_oPO(OR^{60})_2$ (where $R^{60}$: lower alkyl; or lower alkenyl);
—$(CH_2)_oSO_2R^{62}$ (where $R^{62}$: lower alkyl; or lower alkenyl); or
—$(CH_2)_qC_6H_4R^8$ (where $R^8$: H; F; Cl; $CF_3$; lower alkyl; lower alkenyl; or lower alkoxy).

—$R^5$ is lower alkyl; lower alkenyl;
—$(CH_2)_oOR^{55}$ (where $R^{55}$: lower alkyl; or lower alkenyl);
—$(CH_2)_oSR^{56}$ (where $R^{56}$: lower alkyl; or lower alkenyl);
—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{84}$ taken together form: —$(CH_2)_{2-6}$—;
—$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
—$(CH_2)_oN(R^{20})COR^{64}$ (where $R^{20}$: H; or lower alkyl; $R^{64}$: alkyl; alkenyl; aryl; aryl-lower alkyl; or heteroaryl-lower alkyl);
—$(CH_2)_oCOOR^{57}$ (where $R^{57}$: lower alkyl; or lower alkenyl);
—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
—$(CH_2)_oPO(OR^{60})_2$ (where $R^{60}$: lower alkyl; or lower alkenyl);
—$(CH_2)_oSO_2R^{62}$ (where $R^{62}$: lower alkyl; or lower alkenyl); or
—$(CH_2)_qC_6H_4R^8$ (where $R^8$: H; F; Cl; $CF_3$; lower alkyl; lower alkenyl; or lower alkoxy).

—$R^6$ is H; lower alkyl; lower alkenyl;
—$(CH_2)_oOR^{55}$ (where $R^{55}$: lower alkyl; or lower alkenyl);
—$(CH_2)_oSR^{56}$ (where $R^{56}$: lower alkyl; or lower alkenyl);
—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—;
—$(CH_2)_2S(CH_2)_2$—; or —$(CH_2)_2NR^{57}(CH_2)_2$— (where $R^{57}$: H; or lower alkyl));
—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—;
—$(CH_2)_2S(CH_2)_2$—; or —$(CH_2)_2NR^{57}(CH_2)_2$— (where $R^{57}$: H; or lower alkyl));
—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—;
—$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
—$(CH_2)_oN(R^{20})COR^{64}$ (where $R^{20}$: H; or lower alkyl; $R^{64}$ lower alkyl; or lower alkenyl);
—$(CH_2)_oCOOR^{57}$ (where $R^{57}$: lower alkyl; or lower alkenyl);
—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;
—$(CH_2)_2S(CH_2)_2$—; or —$(CH_2)_2NR^{57}(CH_2)_2$— (where $R^{57}$: H; or lower alkyl));
—$(CH_2)_oPO(OR^{60})_2$ (where $R^{60}$: lower alkyl; or lower alkenyl);
—$(CH_2)_oSO_2R^{62}$ (where $R^{62}$: lower alkyl; or lower alkenyl); or
—$(CH_2)_qC_6H_4R^8$ (where $R^8$: H; F; Cl; $CF_3$; lower alkyl; lower alkenyl; or lower alkoxy).

—$R^7$ is lower alkyl; lower alkenyl;
—$(CH_2)_qOR^{55}$ (where $R^{55}$: lower alkyl; or lower alkenyl);
—$(CH_2)_qSR^{56}$ (where $R^{56}$: lower alkyl; or lower alkenyl);
—$(CH_2)_qNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—;
—$(CH_2)_2S(CH_2)_2$—; or —$(CH_2)_2NR^{57}(CH_2)_2$— (where $R^{57}$: H; or lower alkyl));
—$(CH_2)_qOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—;
—$(CH_2)_2S(CH_2)_2$—; or —$(CH_2)_2NR^{57}(CH_2)_2$— (where $R^{57}$: H; or lower alkyl));
—$(CH_2)_qNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—;
—$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
—$(CH_2)_qN(R^{20})COR^{64}$ (where $R^{20}$: H; or lower alkyl; $R^{64}$ lower alkyl; or lower alkenyl);
—$(CH_2)_rCOOR^{57}$ (where $R^{57}$: lower alkyl; or lower alkenyl);
—$(CH_2)_rCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;
—$(CH_2)_2S(CH_2)_2$—; or —$(CH_2)_2NR^{57}(CH_2)_2$— (where $R^{57}$: H; or lower alkyl));
—$(CH_2)_rPO(OR^{60})_2$ (where $R^{60}$: lower alkyl; or lower alkenyl);
—$(CH_2)_rSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).
—$R^8$ is H; F; Cl; $CF_3$; lower alkyl; lower alkenyl;
  —$(CH_2)_oOR^{55}$ (where $R^{55}$: lower alkyl; or lower alkenyl);
  —$(CH_2)_oSR^{56}$ (where $R^{56}$: lower alkyl; or lower alkenyl);
  —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oN(R^{20})COR^{64}$ (where $R^{20}$: H; or lower alkyl; $R^{64}$: lower alkyl; or lower alkenyl);
  —$(CH_2)_oCOOR^{57}$ (where $R^{57}$: lower alkyl; or lower alkenyl);
  —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oPO(OR^{60})_2$ (where $R^{60}$: lower alkyl; or lower alkenyl);
  —$(CH_2)_oSO_2R^{62}$ (where $R^{62}$: lower alkyl; or lower alkenyl); or
  —$(CH_2)_qC_6H_4R^8$ (where $R^8$: H; F; Cl; $CF_3$; lower alkyl; lower alkenyl; or lower alkoxy).
—$R^9$ is lower alkyl; lower alkenyl;
  —$(CH_2)_oOR^{55}$ (where $R^{55}$: lower alkyl; or lower alkenyl);
  —$(CH_2)_oSR^{56}$ (where $R^{56}$: lower alkyl; or lower alkenyl);
  —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{80}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oN(R^{20})COR^{64}$ (where $R^{20}$: H; or lower alkyl; $R^{64}$ lower alkyl; or lower alkenyl);
  —$(CH_2)_oCOOR^{57}$ (where $R^{57}$: lower alkyl; or lower alkenyl);
  —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oPO(OR^{60})_2$ (where $R^{60}$: lower alkyl; or lower alkenyl);
  —$(CH_2)_oSO_2R^{62}$ (where $R^{62}$: lower alkyl; or lower alkenyl); or
  —$(CH_2)_qC_6H_4R^8$ (where $R^8$: H; F; Cl; $CF_3$; lower alkyl; lower alkenyl; or lower alkoxy).
—$R^{10}$ is lower alkyl; lower alkenyl;
  —$(CH_2)_oOR^{55}$ (where $R^{55}$: lower alkyl; or lower alkenyl);
  —$(CH_2)_oSR^{56}$ (where $R^{56}$: lower alkyl; or lower alkenyl);
  —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oN(R^{20})COR^{64}$ (where $R^{20}$: H; or lower alkyl; $R^{64}$ lower alkyl; or lower alkenyl);
  —$(CH_2)_oCOOR^{57}$ (where $R^{57}$: lower alkyl; or lower alkenyl);
  —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oPO(OR^{60})_2$ (where $R^{60}$: lower alkyl; or lower alkenyl);
  —$(CH_2)_oSO_2R^{62}$ (where $R^{62}$: lower alkyl; or lower alkenyl); or
  —$(CH_2)_qC_6H_4R^8$ (where $R^8$: H; F; Cl; $CF_3$; lower alkyl; lower alkenyl; or lower alkoxy).
—$R^{11}$ is H; lower alkyl; lower alkenyl;
  —$(CH_2)_mOR^{55}$ (where $R^{55}$: lower alkyl; or lower alkenyl);
  —$(CH_2)_mSR^{56}$ (where $R^{56}$: lower alkyl; or lower alkenyl);
  —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; (where $R^{57}$: H; or lower alkyl));

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—;

—$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_mN(R^{20})COR^{64}$ (where $R^{20}$: H; or lower alkyl; $R^{64}$ lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$— (where $R^{57}$: H; or lower alkyl));

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

—$R^{12}$ is H; lower alkyl; lower alkenyl;

—$(CH_2)_mOR^{55}$ (where $R^{55}$: lower alkyl; or lower alkenyl);

—$(CH_2)_mSR^{56}$ (where $R^{56}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$— (where $R^{57}$: H; or lower alkyl));

—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$— (where $R^{57}$: H; or lower alkyl));

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—;

—$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_mN(R^{20})COR^{64}$ (where $R^{20}$: H; or lower alkyl; $R^{64}$ lower alkyl; or lower alkenyl);

—$(CH_2)_rCOOR^{57}$ (where $R^{57}$: lower alkyl; or lower alkenyl);

—$(CH_2)_rCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$— (where $R^{57}$: H; or lower alkyl));

—$(CH_2)_rPO(OR^{60})_2$ (where $R^{60}$: lower alkyl; or lower alkenyl);

—$(CH_2)_rSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

—$R^{13}$ is lower alkyl; lower alkenyl;

—$(CH_2)_qOR^{55}$ (where $R^{55}$: lower alkyl; or lower alkenyl);

—$(CH_2)_qSR^{56}$ (where $R^{56}$: lower alkyl; or lower alkenyl);

—$(CH_2)_sNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$— (where $R^{57}$: H; or lower alkyl));

—$(CH_2)_qOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$— (where $R^{57}$: H; or lower alkyl));

—$(CH_2)_qNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—;

—$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_qN(R^{20})COR^{64}$ (where $R^{20}$: H; or lower alkyl; $R^{64}$ lower alkyl; or lower alkenyl);

—$(CH_2)_rCOO^{57}$ (where $R^{57}$: lower alkyl; or lower alkenyl);

—$(CH_2)_qCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$— (where $R^{57}$: H; or lower alkyl));

—$(CH_2)_rPO(OR^{60})_2$ (where $R^{60}$: lower alkyl; or lower alkenyl);

—$(CH_2)_rSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

—$R^{14}$ is H; h lower alkyl; lower alkenyl;

—$(CH_2)_mOR^{55}$ (where $R^{55}$: lower alkyl; or lower alkenyl);

—$(CH_2)_mSR^{56}$ (where $R^{56}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$— (where $R^{57}$: H; or lower alkyl));

—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$— (where $R^{57}$: H; or lower alkyl));

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—;

—$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_mN(R^{20})COR^{64}$ (where $R^{20}$: H; lower alkyl; $R^{64}$: lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$— (where $R^{57}$: H; or lower alkyl));

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl);

—$(CH_2)_qC_6H_4R^8$ (where $R^8$: H; F; Cl; $CF_3$; lower alkyl; lower alkenyl; or lower alkoxy).

—$R^{15}$ is lower alkyl; lower alkenyl;

—$(CH_2)_oOR^{55}$ (where $R^{55}$: lower alkyl; or lower alkenyl);

—$(CH_2)_oSR^{56}$ (where $R^{56}$: lower alkyl; or lower alkenyl);

—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_oN(R^{20})COR^{64}$ (where $R^{20}$: H; or lower alkyl; $R^{64}$ lower alkyl; or lower alkenyl); particularly favoured being —$NR^{20}CO$-lower alkyl (where $R^{20}$: H; or lower alkyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

—$R^{16}$ is lower alkyl; lower alkenyl;

—$(CH_2)_oOR^{55}$ (where $R^{55}$: lower alkyl; or lower alkenyl);

—$(CH_2)_oSR^{56}$ (where $R^{56}$: lower alkyl; or lower alkenyl);

—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$; —$(CH_2)_2S(CH_2)_2$—; or —$(CH_2)_2NR^{57}(CH_2)_2$— (where $R^{57}$: H; or lower alkyl));

—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_oN(R^{20})COR^{64}$ (where $R^{20}$: H; or lower alkyl; $R^{64}$ lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

—$R^{17}$ is lower alkyl; lower alkenyl;

—$(CH_2)_qOR^{55}$ (where $R^{55}$: lower alkyl; or lower alkenyl);

—$(CH_2)_qSR^{56}$ (where $R^{56}$: lower alkyl; or lower alkenyl);

—$(CH_2)_qNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_qOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_qNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_qN(R^{20})COR^{64}$ (where $R^{20}$: H; or lower alkyl; $R^{64}$ lower alkyl; or lower alkenyl);

—$(CH_2)_rCOOR^{57}$ (where $R^{57}$: lower alkyl; or lower alkenyl);

—$(CH_2)_qCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_rPO(OR^{60})_2$ (where $R^{60}$: lower alkyl; or lower alkenyl);

—$(CH_2)_rSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

Among the building blocks A1 to A69 and A105 the following are preferred: A5 with $R^2$ being H, A8, A22, A25, A38 with R² being H, A42, A47, A50 and A105. Most preferred are building blocks of type A8':

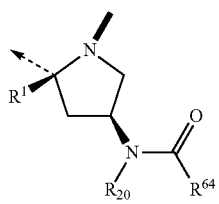

A8' especially those wherein R⁶⁴ is n-hexyl (A8'-1); n-heptyl (A8'-2); 4-(phenyl)benzyl (A8'-3); diphenylmethyl (A8'-4); 3-amino-propyl (A8'-5); 5-amino-pentyl (A8'-6); methyl (A8'-7); ethyl (A8'-8); isopropyl (A8'-9); isobutyl (A8'-10); n-propyl (A8'-11); cyclohexyl (A8'-12); cyclohexylmethyl (A8'-13); n-butyl (A8'-14); phenyl (A8'-15); benzyl (A8'-16); (3-indolyl)methyl (A8'-17); 2-(3-indolyl)ethyl (A8'-18); (4-phenyl)phenyl (A8'-19); and n-nonyl (A8'-20).

Building block A70 belongs to the class of open-chain α-substituted α-amino acids, building blocks A71 and A72 to the corresponding β-amino acid analogues and building blocks A73-A104 to the cyclic analogues of A70. Such amino acid derivatives have been shown to constrain small peptides in well defined reverse turn or U-shaped conformations (C. M. Venkatachalam, *Biopolymers* 1968, 6, 1425-1434; W. Kabsch, C. Sander, *Biopolymers* 1983, 22, 2577). Such building blocks are ideally suited for the stabilization of β-hairpin conformations in peptide loops (D. Obrecht, M. Altorfer, J. A. Robinson, "Novel Peptide Mimetic Building Blocks and Strategies for Efficient Lead Finding", *Adv. Med. Chem.* 1999, Vol. 4, 1-68; P. Balaram, "Non-standard amino acids in peptide design and protein engineering", *Curr. Opin. Struct. Biol.* 1992, 2, 845-851; M. Crisma, G. Valle, C. Toniolo, S. Prasad, R. B. Rao, P. Balaram, "β-turn conformations in crystal structures of model peptides containing α,α-disubstituted amino acids", *Biopolymers* 1995, 35, 1-9; V. J. Hruby, F. Al-Obeidi, W. Kazmierski, *Biochem. J.* 1990, 268, 249-262).

It has been shown that both enantiomers of building blocks -A70-CO— to A104-CO— in combination with a building block —B—CO— being an α-amino acid with L-configuration can efficiently stabilize and induce β-hairpin conformations (D. Obrecht, M. Altorfer, J. A. Robinson, "Novel Peptide Mimetic Building Blocks and Strategies for Efficient Lead Finding", *Adv. Med. Chem.* 1999, Vol. 4, 1-68; D. Obrecht, C. Spiegler, P. Schönholzer, K. Müller, H. Heimgartner, F. Stierli, *Helv. Chim. Acta* 1992, 75, 1666-1696; D. Obrecht, U. Bohdal, J. Daly, C. Lehmann, P. Schönholzer, K. Müller, *Tetrahedron* 1995, 51, 10883-10900; D. Obrecht, C. Lehmann, C. Ruffieux, P. Schönholzer, K. Müller, *Helv. Chim. Acta* 1995, 78, 1567-1587; D. Obrecht, U. Bohdal, C. Broger, D. Bur, C. Lehmann, R. Ruffieux, P. Schönholzer, C. Spiegler, *Helv. Chim. Acta* 1995, 78, 563-580; D. Obrecht, H. Karajiannis, C. Lehmann, P. Schönholzer, C. Spiegler, *Helv. Chim. Acta* 1995, 78, 703-714).

Preferred values for $R^{20}$ in A70 to A104 are H or lower alkyl with methyl being most preferred. Preferred values for $R^{18}$, $R^{19}$ and $R^{21}$-$R^{29}$ in building blocks A70 to A104 are the following:
— $R^{18}$ is lower alkyl.
— $R^{19}$ is lower alkyl; lower alkenyl;
— $-(CH_2)_pOR^{55}$ (where $R^{55}$: lower alkyl; or lower alkenyl);
— $-(CH_2)_pSR^{56}$ (where $R^{56}$: lower alkyl; or lower alkenyl);
— $-(CH_2)_pNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl));
— $-(CH_2)_pOCONR^{33}R^{75}$ (where $R^{33}$: H; lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl));
— $-(CH_2)_pNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: $-(CH_2)_{2-6}-$;
— $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl));
— $-(CH_2)_pN(R^{20})COR^{64}$ (where $R^{20}$: H; or lower alkyl; $R^{64}$ lower alkyl; or lower alkenyl);
— $-(CH_2)_pCOOR^{57}$ (where $R^{57}$: lower alkyl; or lower alkenyl);
— $-(CH_2)_pCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$;
— $-(CH_2)_2S(CH_2)_2-$; or $-(CH_2)_2NR^{57}(CH_2)_2-$ (where $R^{57}$: H; or lower alkyl));
— $-(CH_2)_oPO(OR^{60})_2$ (where $R^{60}$: lower alkyl; or lower alkenyl);
— $-(CH_2)_pSO_2R^{62}$ (where $R^{62}$: lower alkyl; or lower alkenyl); or
— $-(CH_2)_oC_6H_4R^8$ (where $R^8$: H; F; Cl; CF₃; lower alkyl; lower alkenyl; or lower alkoxy).
— $R^{21}$ is H; lower alkyl; lower alkenyl;
— $-(CH_2)_oOR^{55}$ (where $R^{55}$: lower alkyl; or lower alkenyl);
— $-(CH_2)_oSR^{56}$ (where $R^{56}$: lower alkyl; or lower alkenyl);
— $-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl));
— $-(CH_2)_oOCONR^{33}R^{75}$ (where $R^{33}$: H; lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; (where $R^{57}$: H; or lower alkyl));
— $-(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{84}$ taken together form: $-(CH_2)_{2-6}-$;
— $-(CH_2)_2O(CH_2)_2-$; $-(CH_2)_2S(CH_2)_2-$; or $-(CH_2)_2NR^{57}(CH_2)_2-$ (where $R^{57}$: H; or lower alkyl));
— $-(CH_2)_oN(R^{20})COR^{64}$ (where $R^{20}$: H; or lower alkyl; $R^{64}$: lower alkyl; or lower alkenyl);
— $-(CH_2)_oCOOR^{57}$ (where $R^{57}$: lower alkyl; or lower alkenyl);
— $-(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$;
— $-(CH_2)_2S(CH_2)_2-$; or $-(CH_2)_2NR^{57}(CH_2)_2-$ (where $R^{57}$: H; or lower alkyl));

—$(CH_2)_oPO(OR^{60})_2$ (where $R^{60}$: lower alkyl; or lower alkenyl);
—$(CH_2)_oSO_2R^{62}$ (where $R^{62}$: lower alkyl; or lower alkenyl); or
—$(CH_2)_qC_6H_4R^8$ (where $R^8$: H; F; Cl; $CF_3$; lower alkyl; lower alkenyl; or lower alkoxy).

—$R^{22}$ is lower alkyl; lower alkenyl;
  —$(CH_2)_oOR^{55}$ (where $R^{55}$: lower alkyl; or lower alkenyl);
  —$(CH_2)_oSR^{56}$ (where $R^{56}$: lower alkyl; or lower alkenyl);
  —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oN(R^{20})COR^{64}$ (where $R^{20}$: H; or lower alkyl; $R^{64}$ lower alkyl; or lower alkenyl);
  —$(CH_2)_oCOOR^{57}$ (where $R^{57}$: lower alkyl; or lower alkenyl);
  —$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oPO(OR^{60})_2$ (where $R^{60}$: lower alkyl; or lower alkenyl);
  —$(CH_2)_oSO_2R^{62}$ (where $R^{62}$: lower alkyl; or lower alkenyl); or
  —$(CH_2)_qC_6H_4R^8$ (where $R^8$: H; F; Cl; CF; lower alkyl; lower alkenyl; or lower alkoxy).

—$R^{23}$ is H; lower alkyl; lower alkenyl;
  —$(CH_2)_oOR^{55}$ (where $R^{55}$: lower alkyl; or lower alkenyl);
  —$(CH_2)_oSR^{56}$ (where $R^{56}$: lower alkyl; or lower alkenyl);
  —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oNR^{20}CONR^{33}R^{81}$ (where $R^{20}$: H; or lower alkyl; $R^{33}$H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oN(R^{20})COR^{64}$ (where $R^{20}$: H; or lower alkyl; $R^{64}$ lower alkyl; or lower alkenyl); particularly favoured are $NR^{20}$CO-lower alkyl (where $R^{20}$: H; or lower alkyl);
  —$(CH_2)_oCOOR^{57}$ (where $R^{57}$: lower alkyl; or lower alkenyl);
  —$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oPO(OR^{60})_2$ (where $R^{60}$: lower alkyl; or lower alkenyl);
  —$(CH_2)_oSO_2R^{62}$ (where $R^{62}$: lower alkyl; or lower alkenyl); or
  —$(CH_2)_qC_6H_4R^8$ (where $R^8$: H; F; Cl; $CF_3$; lower alkyl; lower alkenyl; or lower alkoxy).

—$R^{24}$ is lower alkyl; lower alkenyl;
  —$(CH_2)_oOR^{55}$ (where $R^{55}$: lower alkyl; or lower alkenyl);
  —$(CH_2)_oSR^{56}$ (where $R^{56}$: lower alkyl; or lower alkenyl);
  —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oOCONR^{33}R^{27}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{84}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oN(R^{20})COR^{64}$ (where $R^{20}$: H; or lower alkyl; $R^{64}$: lower alkyl; or lower alkenyl); particularly favoured are $NR^{20}$CO-lower alkyl (where $R^{20}$: H; or lower alkyl);
  —$(CH_2)_oCOOR^{57}$ (where $R^{57}$: lower alkyl; or lower alkenyl);
  —$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));
  —$(CH_2)_oPO(OR^{60})_2$ (where $R^{60}$: lower alkyl; or lower alkenyl);
  —$(CH_2)_oSO_2R^{62}$ (where $R^{62}$: lower alkyl; or lower alkenyl); or
  —$(CH_2)_qC_6H_4R^8$ (where $R^8$: H; F; Cl; $CF_3$; lower alkyl; lower alkenyl; or lower alkoxy).

—$R^{25}$ is H; lower alkyl; lower alkenyl;
  —$(CH_2)_mOR^{55}$ (where $R^{55}$: lower alkyl; or lower alkenyl);
  —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_mN(R^{20})COR^{64}$ (where $R^{20}$: H; or lower alkyl; $R^{64}$ lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

—$R^{26}$ is H; lower alkyl; lower alkenyl;

—$(CH_2)_mOR^{55}$ (where $R^{55}$: lower alkyl; or lower alkenyl);

—$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_mOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_mNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_mN(R^{20})COR^{64}$ (where $R^{20}$: H; or lower alkyl; $R^{64}$ lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy); or, alternatively, —$R^{25}$ and $R^{26}$ taken together are —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl).

—$R^{27}$ is H; lower alkyl; lower alkenyl;

—$(CH_2)_oOR^{55}$ (where $R^{55}$: lower alkyl; or lower alkenyl);

—$(CH_2)_oSR^{56}$ (where $R^{56}$: lower alkyl; or lower alkenyl);

—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_oOCONR^{33}R^{73}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_oN(R^{22})COR^{64}$ (where $R^{20}$: H; or lower alkyl; $R^{64}$ lower alkyl; or lower alkenyl);

—$(CH_2)_oCOOR^{57}$ (where $R^{57}$: lower alkyl; or lower alkenyl);

—$(CH_2)_oCONR^{58}R^{59}$ (where $R^{58}$: lower alkyl, or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_oPO(OR^{60})_2$ (where $R^{60}$: lower alkyl; or lower alkenyl);

—$(CH_2)_oSO_2R^{62}$ (where $R^{62}$: lower alkyl; or lower alkenyl); or

—$(CH_2)_qC_6H_4R^8$ (where $R^8$: H; F; Cl; $CF_3$; lower alkyl; lower alkenyl; or lower alkoxy).

—$R^{28}$ is lower alkyl; lower alkenyl;

—$(CH_2)_oOR^{55}$ (where $R^{55}$: lower alkyl; or lower alkenyl);

—$(CH_2)_oSR^{56}$ (where $R^{56}$: lower alkyl; or lower alkenyl);

—$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_oOCONR^{33}R^{75}$ (where $R^{33}$: H; lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_oNR^{20}CONR^{33}R^{81}$ (where $R^{20}$: H; or lower alkyl; $R^{33}$: H; lower alkyl; or lower alkenyl; $R^{81}$: H; or lower alkyl; or $R^{33}$ and $R^{81}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl));

—$(CH_2)_oN(R^{20})COR^{64}$ (where $R^{20}$: H; or lower alkyl; $R^{64}$ lower alkyl; or lower alkenyl);

—$(CH_2)_oCOOR^{57}$ (where $R^{57}$: lower alkyl; or lower alkenyl);

—(CH$_2$)$_o$CONR$^{58}$R$^{59}$ (where R$^{58}$: lower alkyl, or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl));

—(CH$_2$)$_o$PO(OR$^{60}$)$_2$ (where R$^{60}$: lower alkyl; or lower alkenyl);

—(CH$_2$)$_o$SO$_2$R$^{62}$ (where R$^{62}$: lower alkyl; or lower alkenyl); or

—(CH$_2$)$_q$C$_6$H$_4$R$^8$ (where R$^8$: H; F; Cl; CF$_3$; lower alkyl; lower alkenyl; or lower alkoxy).

—R$^{29}$ is lower alkyl; lower alkenyl;

—(CH$_2$)$_o$OR$^{55}$ (where R$^{55}$: lower alkyl; or lower alkenyl);

—(CH$_2$)$_o$SR$^{56}$ (where R$^{56}$: lower alkyl; or lower alkenyl);

—(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl));

—(CH$_2$)$_o$OCONR$^{33}$R$^{75}$ (where R$^{33}$: H; lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl));

—(CH$_2$)$_o$NR$^{20}$CONR$^{33}$R$^{81}$ (where R$^{20}$: H; or lower alkyl; R$^{33}$: H; lower alkyl; or lower alkenyl; R$^{81}$: H; or lower alkyl; or R$^{33}$ and R$^{81}$ taken together form: —(CH$_2$)$_{2-6}$—;

—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl));

—(CH$_2$)$_o$N(R$^{20}$)COR$^{64}$ (where R$^{20}$: H; or lower alkyl; R$^{64}$ lower alkyl; or lower alkenyl); particularly favored are NR$^{20}$CO-lower-alkyl (where R$^{20}$: H; or lower alkyl);

—(CH$_2$)$_o$COOR$^{57}$ (where R$^{57}$: lower alkyl; or lower alkenyl);

—(CH$_2$)$_o$CONR$^{58}$R$^{59}$ (where R$^{58}$: lower alkyl, or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{11}$(CH$_2$)$_2$— (where R$^{57}$: H; or lower alkyl));

—(CH$_2$)$_o$PO(OR$^{60}$)$_2$ (where R$^{60}$: lower alkyl; or lower alkenyl);

—(CH$_2$)$_o$SO$_2$R$^{62}$ (where R$^{62}$: lower alkyl; or lower alkenyl); or

—(CH$_2$)$_q$C$_6$H$_4$R$^8$ (where R$^8$: H; F; Cl; CF$_3$; lower alkyl; lower alkenyl; or lower alkoxy).

Among the building blocks A70 to A104 the following are preferred: A74 with R$^{22}$ being H, A75, A76, A77 with R$^{22}$ being H, A78 and A79.

The building block —B—CO— designates an L-amino acid residue. Preferred values for B are: —NR$^{20}$CH(R$^{71}$)—, enantiomers of groups A5 with R$^2$ being H, A8, A22, A25, A38 with R$^2$ being H, A42, A47, A50, and A105. Most preferred building blocks —B—CO— are Ala L-Alanine
Arg L-Arginine
Asn L-Asparagine
Asp L-Aspartic acid
Cys L-Cysteine
Gln L-Glutamine
Glu L-Glutamic acid
Gly Glycine
His L-Histidine
Ile L-Isoleucine
Leu L-Leucine
Lys L-Lysine
Met L-Methionine
Phe L-Phenylalanine
Pro L-Proline
Ser L-Serine
Thr L-Threonine
Trp L-Tryptophan
Tyr L-Tyrosine
Val L-Valine
Cit L-Citrulline
Orn L-Ornithine
tBuA L-t-Butylalanine
Sar Sarcosine
t-BuG L-tert.-Butylglycine
4AmPhe L-para-Aminophenylalanine
3AmPhe L-meta-Aminophenylalanine
2AmPhe L-ortho-Aminophenylalanine
Phe(mC(NH$_2$)=NH) L-meta-Amidinophenylalanine
Phe(pC(NH$_2$)=NH) L-para-Amidinophenylalanine
Phe(mNHC(NH$_2$)=NH) L-meta-Guanidinophenylalanine
Phe(pNHC(NH$_2$)=NH) L-para-Guanidinophenylalanine
Phg L-Phenylglycine
Cha L-Cyclohexylalanine
C$_4$al L-3-Cyclobutylalanine
C$_5$al L-3-Cyclopentylalanine
Nle L-Norleucine
2-Nal L-2-Naphthylalanine
1-Nal L-1-Naphthylalanine
4Cl-Phe L-4-Chlorophenylalanine
3Cl-Phe L-3-Chlorophenylalanine
2Cl-Phe L-2-Chlorophenylalanine
3,4Cl$_2$-Phe L-3,4-Dichlorophenylalanine
4F-Phe L-4-Fluorophenylalanine
3F-Phe L-3-Fluorophenylalanine
2F-Phe L-2-Fluorophenylalanine
Tic L-1,2,3,4-Tetrahydroisoquinoline-3-carboxylic acid
Thi L-β-2-Thienylalanine
Tza L-2-Thiazolylalanine
Mso L-Methionine sulfoxide
AcLys L-N-Acetyllysine
Dpr L-2,3-Diaminopropionic acid
A$_2$Bu L-2,4-Diaminobutyric acid
Dbu (2S,3S)-2,3-Diaminobutyric acid
Abu γ-Aminobutyric acid (GABA)
Aha ε-Aminohexanoic acid
Aib α-Aminoisobutyric acid
Tyr(Bzl) L-O-Benzyltyrosine
Bip L-Biphenylalanine
Ser(Bzl) L-O-Benzylserine
Thr(Bzl) L-O-Benzylthreonine
hCha L-Homo-cyclohexylalanine
hCys L-Homo-cysteine
hSer L-Homo-serine
hArg L-Homo-arginine
hPhe L-Homo-phenylalanine
Bpa L-4-Benzoylphenylalanine
Pip L-Pipecolic acid
OctG L-Octylglycine
MePhe L-N-Methylphenylalanine
MeNle L-N-Methylnorleucine
MeAla L-N-Methylalanine
MeIle L-N-Methylisoleucine
MeVal L-N-Methyaline MeLeu L-N-Methylleucine
4Hyp1 (4S)-L-Hydroxyproline
4Hyp2 (4R)-L-Hydroxyproline
4 Mp1 (4S)-L-Mercaptoproline
4 Mp2 (4R)-L-Mercaptoproline
Oic (3aS, 7aS)-L-1-Octahydro-1H-indole-2-carboxylic acid In addition, the most preferred values for B also include groups of type A8″ of (L)-configuration:

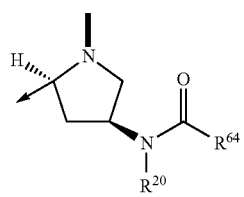

A8″ wherein $R^{20}$ is H or lower alkyl and $R^{64}$ is alkyl; alkenyl; —[(CH$_2$)$_u$—X]$_t$—CH$_3$ (where X is —O—; —NR$^{20}$—, or —S—; u=1-3, and t=1-6), aryl; aryl-lower alkyl; or heteroaryl-lower alkyl; especially those wherein $R^{64}$ is n-hexyl (A8″-21); n-heptyl (A8″-22); 4-(phenyl)benzyl (A8″-23); diphenylmethyl (A8″-24); 3-amino-propyl (A8″-25); 5-amino-pentyl (A8″-26); methyl (A8″-27); ethyl (A8″-28); isopropyl (A8″-29); isobutyl (A8″-30); n-propyl (A8″-31); cyclohexyl (A8″-32); cyclohexyl-methyl (A8″-33); n-butyl (A8″-34); phenyl (A8″-35); benzyl (A8″-36); (3-indolyl)methyl (A8″-37); 2-(3-indolyl)ethyl (A8″-38); (4-phenyl)-phenyl (A8″-39); n-nonyl (A8″-40); CH$_3$—OCH$_2$CH$_2$—OCH$_2$— (A8″-41) and CH$_3$—(OCH$_2$CH$_2$)$_2$—OCH$_2$— (A8″-42).

Besides the structural element —B—CO— the β-hairpin peptidomimetics of the present invention can comprise the structural element -A-CO— and amino acid residues belonging to one of the following groups:

Group C —NR$^{20}$CH(R$^{22}$)CO—; "hydrophobic: small to medium-sized"
Group D —NR$^{20}$CH(R$^{73}$)CO—; "hydrophobic: large aromatic or heteroaromatic"
Group E —NR$^{20}$CH(R$^{74}$)CO—; "polar-cationic" and "urea-derived"
Group F —NR$^{20}$CH(R$^{84}$)CO—; "polar-non-charged or anionic"
Group I —NR$^{86}$CH$_2$CO—;
Group M —NR$^{20}$CH(R$^{72}$)(CH$_2$)$_2$CO—; —NR$^{20}$CH(R$^{73}$)(CH$_2$)$_2$CO—; —NR$^{20}$CH(R$^{74}$)(CH$_2$)$_2$CO—; or —NR$^{20}$CH(R$^{84}$)(CH$_2$)$_2$CO—; "γ$^4$-amino acids"
Group N —NR$^{20}$CH(R$^{72}$)(CH$_2$)CO—; —NR$^{20}$CH(R$^{73}$)(CH$_2$)CO—; —NR$^{20}$CH(R$^{74}$)(CH$_2$)CO—, or —NR$^{20}$CH(R$^{84}$)(CH$_2$)CO—; "β$^3$-amino acids"

Group C comprises amino acid residues with small to medium-sized hydrophobic side chain groups according to the general definition for substituent $R^{72}$. A hydrophobic residue refers to an amino acid side chain that is uncharged at physiological pH and that is repelled by aqueous solution. Furthermore these side chains generally do not contain hydrogen bond donor groups, such as (but not limited to) primary and secondary amides, primary and secondary amines and the corresponding protonated salts thereof, thiols, alcohols, phosphonates, phosphates, ureas or thioureas. However, they may contain hydrogen bond acceptor groups such as ethers, thioethers, esters, tertiary amides, alkyl- or aryl phosphonates and phosphates or tertiary amines. Genetically encoded small-to-medium-sized hydrophobic amino acids include alanine, isoleucine, leucine, methionine and valine.

Group D comprises amino acid residues with aromatic and heteroaromatic side chain groups according to the general definition for substituent $R^{73}$. An aromatic amino acid residue refers to a hydrophobic amino acid having a side chain containing at least one ring having a conjugated π-electron system (aromatic group). In addition they may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tetriary amides, alkyl- or aryl phosphonates- and phosphates or tertiary amines. Genetically encoded aromatic amino acids include phenylalanine and tyrosine.

A heteroaromatic amino acid residue refers to a hydrophobic amino acid having a side chain containing at least one ring having a conjugated π-system incorporating at least one heteroatom such as (but not limited to) O, S and N according to the general definition for substituent $R^{77}$. In addition such residues may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tetriary amides, alkyl- or aryl phosphonates- and phosphates or tertiary amines. Genetically encoded heteroaromatic amino acids include tryptophan and histidine.

Group E comprises amino acids containing side chains with polar-cationic, acylamino- and urea-derived residues according to the general definition for substituent $R^{74}$. Polar-cationic refers to a basic side chain which is protonated at physiological pH. Genetically encoded polar-cationic amino acids include arginine, lysine and histidine. Citrulline is an example for an urea derived amino acid residue.

Group F comprises amino acids containing side chains with polar-non-charged or anionic residues according to the general definition for substituent $R^{84}$. A polar-non-charged or anionic residue refers to a hydrophilic side chain that is uncharged and, respectively anionic at physiological pH (carboxylic acids being included), but that is not repelled by aqueous solutions. Such side chains typically contain hydrogen bond donor groups such as (but not limited to) primary and secondary amides, carboxyclic acids and esters, primary and secondary amines, thiols, alcohols, phosphonates, phosphates, ureas or thioureas. These groups can form hydrogen bond networks with water molecules. In addition they may also contain hydrogen bond acceptor groups such as (but not limited to) ethers, thioethers, esters, tetriary amides, carboxylic acids and carboxylates, alkyl- or aryl phosphonates- and phosphates or tertiary amines. Genetically encoded polar-non-charged amino acids include asparagine, cysteine, glutamine, serine and threonine, but also aspartic acid and glutamic acid.

Group I comprises glycine having the amino group substituted by chains containing polar-cationic, hydrophobic, aromatic, heteroaromatic, polar-non-charged or anionic residues according to the general definition for substituent $R^{86}$. Polar-cationic refers to a basic side chain which is protonated at physiological pH. A hydrophobic residue refers to an amino acid side chain that is uncharged at physiological pH and that is repelled by aqueous solution. Aromatic refers to a hydrophobic side chain containing at least one ring having a conjugated π-electron system (aromatic group). Heteroaromatic refers to a hydrophobic side chain containing at least one ring having a conjugated π-system incorporating at least one heteroatom. A polar-non-charged or anionic residue refers to a hydrophilic side chain that is uncharged and, respectively anionic at physiological pH (carboxylic acids being included), but that is not repelled by aqueous solutions.

Group M comprises $\gamma^4$-amino acid residues having both the amino group and the side chain attached to the γ-carbon atom with side chain groups according to the general definition for substituent $R^{71}$; $\gamma^4$-amino acid residues with small to medium-sized hydrophobic side chain groups according to the general definition for substituent $R^{72}$; $\gamma^4$-amino acid residues with aromatic and heteroaromatic side chain groups according to the general definition for substituent $R^{73}$; $\gamma^4$-amino acid residues with polar-cationic, acylamino- and urea-derived side chain groups according to the general definition for substituent $R^{74}$; and $\gamma^4$-amino acid residues with polar-non-charged or anionic groups according to the general definition for substituent $R^{84}$. Hydrophobic side chain groups are uncharged at physiological pH and repelled by aqueous solution. An aromatic side chain group is hydrophobic and contains at least one ring having a conjugated π-electron system (aromatic group). A heteroaromatic side chain group is hydrophobic and contains at least one ring having a conjugated π-system incorporating at least one heteroatom such as (but not limited to) O, S and N according to the general definition for substituent $R^{77}$. A polar-cationic side chain group refers to a basic side chain which is protonated at physiological pH. A polar-non-charged or anionic side chain group is uncharged and, respectively anionic at physiological pH (carboxylic acids being included), but is not repelled by aqueous solutions.

Group N comprises $\beta^3$-amino acid residues having both the amino group and the side chain attached to the β-carbon atom with side chain groups according to the general definition for substituent $R^{71}$; $\beta^3$-amino acid residues with small to medium-sized hydrophobic side chain groups according to the general definition for substituent $R^{72}$; $\beta^3$-amino acid residues with aromatic and heteroaromatic side chain groups according to the general definition for substituent $R^{73}$; $\beta^3$-amino acid residues with polar-cationic, acylamino- and urea-derived side chain groups according to the general definition for substituent $R^{74}$; and $\beta^3$-amino acid residues with polar-non-charged or anionic groups according to the general definition for substituent $R^{84}$. Hydrophobic side chain groups are uncharged at physiological pH and repelled by aqueous solution. An aromatic side chain group is hydrophobic and contains at least one ring having a conjugated π-electron system (aromatic group). A heteroaromatic side chain group is hydrophobic and contains at least one ring having a conjugated π-system incorporating at least one heteroatom such as (but not limited to) O, S and N according to the general definition for substituent $R^{77}$. A polar-cationic side chain group refers to a basic side chain which is protonated at physiological pH. A polar-non-charged or anionic side chain group is uncharged and, respectively anionic at physiological pH (carboxylic acids being included), but is not repelled by aqueous solutions.

As mentioned earlier, the β-hairpin peptidomimetics of the invention contain a disulfide bond between $Cys^4$ and $Cys^{11}$. Such an interstrand linkage is known to stabilize the β-hairpin conformations and thus constitute an important structural element for the design of β-hairpin mimetics.

Most preferred amino acid residues in Cyclo(-$Xaa^1$-$Xaa^2$-$Xaa^3$-$Cys^4$-$Xaa^5$-$Xaa^6$-$Xaa^7$-$Xaa^8$-$Arg^9$-$Tyr^{10}$-$Cys^{11}$-$Xaa^{12}$-$Xaa^{13}$-$Xaa^{14}$-$Xaa^{15}$-$Xaa^{16}$-), disulfide bond between $Cys^4$ and $Cys^{11}$, are those derived from natural α-, β- and γ-amino acids. Hereinafter follows a list of amino acids which, or the residues of which, are suitable for the purposes of the present invention, the abbreviations corresponding to generally adopted usual practice:

| three letter code | | one letter code |
|---|---|---|
| Ala | L-Alanine | A |
| $^D$Ala | D-Alanine | $^D$A |
| Arg | L-Arginine | R |
| $^D$Arg | D-Arginine | $^D$R |
| Asn | L-Asparagine | N |
| $^D$Asn | D-Asparagine | $^D$N |
| Asp | L-Aspartic acid | D |
| $^D$Asp | D-Aspartic acid | $^D$D |
| Cys | L-Cysteine | C |
| $^D$Cys | D-Cysteine | $^D$C |
| Glu | L-Glutamic acid | E |
| $^D$Glu | D-Glutamic acid | $^D$E |
| Gln | L-Glutamine | Q |
| $^D$Gln | D-Glutamine | $^D$Q |
| Gly | Glycine | G |
| His | L-Histidine | H |
| $^D$His | D-Histidine | $^D$H |
| Ile | L-Isoleucine | I |
| $^D$Ile | D-Isoleucine | $^D$I |
| Leu | L-Leucine | L |
| $^D$Leu | D-Leucine | $^D$L |
| Lys | L-Lysine | K |
| $^D$Lys | D-Lysine | $^D$K |
| Met | L-Methionine | M |
| $^D$Met | D-Methionine | $^D$M |
| Phe | L-Phenylalanine | F |
| $^D$Phe | D-Phenylalanine | $^D$F |
| Pro | L-Proline | P |
| $^D$Pro | D-Proline | $^D$P |
| Ser | L-Serine | S |
| $^D$Ser | D-Serine | $^D$S |
| Thr | L-Threonine | T |
| $^D$Thr | D-Threonine | $^D$T |
| Trp | L-Tryptophan | W |
| $^D$Trp | D-Tryptophan | $^D$W |
| Tyr | L-Tyrosine | Y |
| $^D$Tyr | D-Tyrosine | $^D$Y |
| Val | L-Valine | V |
| $^D$Val | D-Valine | $^D$V |

3-Amino-propanoic acid

H-$\beta^3$-HAla-OH (3S)-3-Amino-butyric acid

H-$\beta^3$-HVal-OH (3R)-3-Amino-4-methyl-valeric acid

H-$\beta^3$-HIle-OH (3R,4S)-3-Amino-4-methyl-hexanoic acid

H-$\beta^3$-HLeu-OH (3S)-3-Amino-5-methyl-hexanoic acid

H-$\beta^3$-HMet-OH (3S)-3-Amino-5-methylthio-pentanoic acid

H-$\beta^3$-HTyr-OH (3S)-3-Amino-4-(4'-hydroxyphenyl)-butyric acid

H-$\beta^3$-HHis-OH (3S)-3-Amino-4-(imidazole-4'-yl)-butyric acid

H-$\beta^3$-HPhe-OH (3S)-3-Amino-4-phenyl-butyric acid

H-$\beta^3$-HTrp-OH (3S)-3-Amino-4-(indol-3'-yl)-butyric acid

H-$\beta^3$-HSer-OH (3R)-3-Amino-4-hydroxy-butyric acid

H-$\beta^3$-HAsp-OH 3-Amino-pentanedioic acid

H-$\beta^3$-HGlu-OH (3S)-3-Amino-hexanedioic acid

H-$\beta^3$-HLys-OH (3S)-3,7-Diamino-heptanoic acid

H-$\beta^3$-HArg-OH (3S)-3-Amino-6-guanidino-hexanoic-acid

H-$\beta^3$-HCys-OH (3R)-3-Amino-4-mercapto-butyric acid

H-$\beta^3$-HAsn-OH (3S)-3-Amino-4-carbamoyl-butyric acid

H-$\beta^3$-HGln-OH (3S)-3-Amino-5-carbamoyl-pentanoic acid

H-β³-HThr-OH (3R,4R)-3-Amino-4-hydroxy-pentanoic acid

4-Amino-butyric acid

H-γ⁴-DiHAla-OH (4S)-4-Amino-pentanoic acid
H-γ⁴-DiHVal-OH (4R)-4-Amino-5-methyl-hexanoic acid
H-γ⁴-DiHIle-OH (4R,5S)-4-Amino-5-methyl-heptanoic acid
H-γ⁴-DiHLeu-OH (4R)-4-Amino-6-methyl-heptanoic acid
H-γ⁴-DiHMet-OH (4R)-4-Amino-6-methylthio-hexanoic acid
H-γ⁴-DiHTyr-OH (4R)-4-Amino-5-(4'-hydroxyphenyl)-pentanoic acid
H-γ⁴-DiHHis-OH (4R)-4-Amino-5-(imidazole-4'-yl)-pentanoic acid
H-γ⁴-DiHPhe-OH (4R)-4-Amino-5-phenyl-pentanoic acid
H-γ⁴-DiHTrp-OH (4R)-4-Amino-5-(indol-3'-yl)-pentanoic acid
H-γ⁴-DiHSer-OH (4R)-4-Amino-5-hydroxy-pentanoic acid
H-γ⁴-DiHAsp-OH (4R)-4-Amino-hexanedioic acid
H-γ⁴-DiHGlu-OH 4-Amino-heptanedioic acid
H-γ⁴-DiHLys-OH (4S)-4,8-Diamino-octanoic acid
H-γ⁴-DiHArg-OH (4S)-4-Amino-7-guanidino-heptanoic-acid
H-γ⁴-DiHCys-OH (4R)-4-Amino-5-mercapto-pentanoic acid
H-γ⁴-DiHAsn-OH (4R)-4-Amino-5-carbamoyl-pentanoic acid
H-γ⁴-DiHGln-OH (3S)-3-Amino-5-carbamoyl-hexanoic acid
H-γ⁴-DiHThr-OH (4R,5R)-4-Amino-5-hydroxy-hexanoic acid Other α-, β- and γ-amino acids which, or the residues of which, are suitable for the purposes of the present invention include:

Cit L-Citrulline
$^D$Cit D-Citrulline
Orn L-Ornithine
$^D$Orn D-Ornithine
tBuA L-t-Butylalanine
$^D$tBuA D-t-Butylalanine
Sar Sarcosine
Pen L-Penicillamine
$^D$Pen D-Penicillamine
tBuG L-tert.-Butylglycine
$^D$tBuG D-tert.-Butylglycine
4AmPhe L-para-Aminophenylalanine
$^D$4AmPhe D-para-Aminophenylalanine
3AmPhe L-meta-Aminophenylalanine
$^D$3AmPhe D-meta-Aminophenylalanine
2AmPhe L-ortho-Aminophenylalanine
$^D$2AmPhe D-ortho-Aminophenylalanine
Phe(mC(NH₂)=NH) L-meta-Amidinophenylalanine
$^D$Phe(mC(NH₂)=NH) D-meta-Amidinophenylalanine
Phe(pC(NH₂)=NH) L-para-Amidinophenylalanine
$^D$Phe(pC(NH₂)=NH) D-para-Amidinophenylalanine
Phe(mNHC(NH₂)=NH) L-meta-Guanidinophenylalanine
$^D$Phe(mNHC(NH₂)=NH) D-meta-Guanidinophenylalanine
Phe(pNHC(NH₂)=NH) L-para-Guanidinophenylalanine
$^D$Phe(pNHC(NH₂)=NH) D-para-Guanidinophenylalanine
2 Pal (2S)-2-Amino-3-(pyridine-2'-yl)-propionic acid
$^D$2 Pal (2R)-2-Amino-3-(pyridine-2'-yl)-propionic acid
4 Pal (2S)-2-Amino-3-(pyridine-4'-yl)-propionic acid
$^D$4 Pal (2R)-2-Amino-3-(pyridine-4'-yl)-propionic acid
Phg L-Phenylglycine
$^D$Phg D-Phenylglycine
Cha L-Cyclohexylalanine
$^D$Cha D-Cyclohexylalanine
C₄al L-3-Cyclobutylalanine
$^D$C₄al D-3-Cyclobutylalanine
C₅al L-3-Cyclopentylalanine
$^D$C₅al D-3-Cyclopentylalanine
Nle L-Norleucine
$^D$Nle D-Norleucine
2-Nal L-2-Naphthylalanine
$^D$2Nal D-2-Naphthylalanine
1-Nal L-1-Naphthylalanine
$^D$1Nal D-1-Naphthylalanine
4ClPhe L-4-Chlorophenylalanine
$^D$4ClPhe D-4-Chlorophenylalanine
3ClPhe L-3-Chlorophenylalanine
$^D$3ClPhe D-3-Chlorophenylalanine
2ClPhe L-2-Chlorophenylalanine
$^D$2ClPhe D-2-Chlorophenylalanine
3,4Cl₂Phe L-3,4-Dichlorophenylalanine
$^D$3,4Cl₂Phe D-3,4-Dichlorophenylalanine
4FPhe L-4-Fluorophenylalanine
$^D$4FPhe D-4-Fluorophenylalanine
3FPhe L-3-Fluorophenylalanine
$^D$3FPhe D-3-Fluorophenylalanine
2FPhe L-2-Fluorophenylalanine
$^D$2FPhe D-2-Fluorophenylalanine
Thi L-β-2-Thienylalanine
$^D$Thi D-β-2-Thienylalanine
Tza L-2-Thiazolylalanine
$^D$Tza D-2-Thiazolylalanine
Mso L-Methionine sulfoxide
$^D$Mso D-Methionine sulfoxide
AcLys N-Acetyllysine
$^D$AcLys N-Acetyl-D-lysine
Dpr 2,3-Diaminopropionic acid
$^D$Dpr D-2,3-Diaminopropionic acid
A₂Bu 2,4-Diaminobutyric acid
$^D$A₂BU (2R)-2,4-Diaminobutyric acid
Dab L-2,4-Diaminobutyric acid
$^D$Dab D-2,4-Diaminobutyric acid
Dbu (2S)-2,3-Diamino-butyric acid
$^D$Dbu (2R)-2,3-Diamino-butyric acid
Abu γ-Aminobutyric acid (GABA)
Aha ε-Aminohexanoic acid
Aib α-Aminoisobutyric acid
Cyp 1-Amino cyclopentane carboxylic acid
Tyr(Bzl) L-O-Benzyltyrosine
$^D$Tyr(Bzl) D-O-Benzyltyrosine
His(Bzl) (3S)-2-Amino-3-(1'-benzylimidazole-4'-yl)-propionic acid
$^D$His(Bzl) (3R)-2-Amino-3-(1'-benzylimidazole-4'-yl)-propionic acid
Bip L-(4-phenyl)phenylalanine
$^D$Bip D-(4-phenyl)phenylalanine
Ser(Bzl) L-O-Benzylserine
$^D$Ser(Bzl) D-O-Benzylserine
Thr(Bzl) L-O-Benzylthreonine
$^D$Thr(Bzl) D-O-Benzylthreonine
alloT (2S,3S)-2-Amino-3-hydroxy-butyric acid
$^D$alloT (2R,3S)-2-Amino-3-hydroxy-butyric acid
Leu3OH (2S,3R)-2-Amino-3-hydroxy-4-methyl-pentanoic acid
$^D$Leu3OH (2R,3R)-2-Amino-3-hydroxy-4-methyl-pentanoic acid
hAla L-Homo-alanine
$^D$hAla D-Homo-alanine
hArg L-Homo-arginine
$^D$hArg D-Homo-arginine hCys L-Homo-cysteine
$^D$hCys D-Homo-cysteine
hGlu L-Homo-glutamic acid
$^D$hGlu D-glutamic acid
hGln L-Homo-glutamine
$^D$hGln D-Homo-glutamine
hHis L-Homo-histidine
$^D$hHis D-Homo-histidine
hIle L-Homo-isoleucine
$^D$hIle D-Homo-isoleucine
hLeu L-Homo-leucine
$^D$hLeu D-Homo-leucine
hNle L-Homo-norleucine
$^D$hNle D-Homo-norleucine
hLys L-Homo-lysine
$^D$hLys D-Homo-lysine
hMet L-Homo-Methionine
$^D$hMet D-Homo-Methionine
hPhe L-Homo-phenylalanine
$^D$hPhe D-Homo-phenylalanine
hSer L-Homo-serine
$^D$hSer D-Homo-serine
hThr L-Homo-threonine
$^D$hThr D-Homo-threonine
hTrp L-Homo-tryptophan
$^D$hTrp D-Homo-tryptophan
hTyr L-Homo-tyrosine
$^D$hTyr D-Homo-tyrosine
hVal L-Homo-valine
$^D$hVal D-Homo-valine
hCha L-Homo-cyclohexylalanine
$^D$hCha D-Homo-cyclohexylalanine
Bpa L-4-Benzoylphenylalanine
$^D$Bpa D-4-Benzoylphenylalanine
OctG L-Octylglycine
$^D$OctG D-Octylglycine
Tic (3S)-1,2,3,4-Tetrahydroisoquinoline-3-carboxylic acid
$^D$Tic (3R)-1,2,3,4-Tetrahydroisoquinoline-3-carboxylic acid
Tiq (1S)-1,2,3,4-Tetrahydroisoquinoline-1-carboxylic acid
$^D$Tiq (1R)-1,2,3,4-Tetrahydroisoquinoline-1-carboxylic acid
Oic (2S,3aS,7aS)-1-Octahydro-1H-indole-2-carboxylic acid
$^D$Oic (2R, 3aS, 7aS)-1-Octahydro-1H-indole-2-carboxylic acid
4AmPyrrl (2S,4S)-4-Amino-pyrrolidine-2-carboxylic acid
$^D$4AmPyrr1 (2R,4S)-4-Amino-pyrrolidine-2-carboxylic acid
4AmPyrr2 (2S,4R)-4-Amino-pyrrolidine-2-carboxylic acid
$^D$4AmPyrr2 (2R,4R)-4-Amino-pyrrolidine-2-carboxylic acid
4PhePyrr1 (2S,4R)-4-Phenyl-pyrrolidine-2-carboxylic acid
$^D$4PhePyrr1 (2R,4R)-4-Phenyl-pyrrolidine-2-carboxylic acid
4PhePyrr2 (2S,4S)-4-Phenyl-pyrrolidine-2-carboxylic acid
$^D$4PhePyrr2 (2R,4S)-4-Phenyl-pyrrolidine-2-carboxylic acid
5PhePyrr1 (2S,5R)-5-Phenyl-pyrrolidine-2-carboxylic acid
$^D$5PhePyrr1 (2R,5R)-5-Phenyl-pyrrolidine-2-carboxylic acid
5PhePyrr2 (2S,5S)-5-Phenyl-pyrrolidine-2-carboxylic acid
$^D$5PhePyrr2 (2R,5S)-5-Phenyl-pyrrolidine-2-carboxylic acid
4Hyp1 (4S)-L-Hydroxyproline
$^D$4Hyp1 (4S)-D-Hydroxyproline
4Hyp2 (4R)-L-Hydroxyproline
$^D$4Hyp2 (4R)-D-Hydroxyproline
4 Mp1 (4S)-L-Mercaptoproline
$^D$4 Mp1 (4S)-D-Mercaptoproline
4 Mp2 (4R)-L-Mercaptoproline
$^D$4 Mp2 (4R)-D-Mercaptoproline
Pip L-Pipecolic acid
$^D$pip D-Pipecolic acid
H-$\beta^3$-HCit-OH (3S)-3-Amino-6-carbamidyl-hexanoic acid
H-$\beta^3$-HOrn-OH (3S)-3,6-Diamino-hexanoic acid
H-$\beta^3$-HtBuA-OH (3S)-3-Amino-5,5-dimethyl-hexanoic acid
H-$\beta^3$-HSar-OH N-Methyl-3-amino-propionic acid
H-$\beta^3$-HPen-OH (3R)-3-Amino-4-methyl-4-mercapto-pentanoic acid
H-$\beta^3$-HtBuG-OH (3R)-3-Amino-4,4-dimethyl-pentanoic acid
H-$\beta^3$-H4AmPhe-OH (3S)-3-Amino-4-(4'-aminophenyl)-butyric acid
H-$\beta^3$-H3AmPhe-OH (3S)-3-Amino-4-(3'-aminophenyl)-butyric acid
H-$\beta^3$-H2AmPhe-OH (3S)-3-Amino-4-(2'-aminophenyl)-butyric acid
H-$\beta^3$-HPhe(mC(NH$_2$)=NH)—OH (3S)-3-Amino-4-(3'-amidinophenyl)-butyric acid
H-$\beta^3$-HPhe(pC(NH$_2$)=NH)—OH (3S)-3-Amino-4-(4'-amidinophenyl)-butyric acid
H-$\beta^3$-HPhe(mNHC(NH$_2$)=NH)—OH (3S)-3-Amino-4-(3'-guanidinophenyl)-butyric acid
H-$\beta^3$-HPhe(pNHC(NH$_2$)=NH)—OH (3S)-3-Amino-4-(4'-guanidino-phenyl)-butyric acid
H-$\beta^3$-H2Pal-OH (3S)-3-Amino-4-(pyridine-2'-yl)-butyric acid
H-$\beta^3$-H4Pal-OH (3S)-3-Amino-4-(pyridine-4'-yl)-butyric acid
H-$\beta^3$-HPhg-OH (3R)-3-Amino-3-phenyl-propionic acid
H-$\beta^3$-HCha-OH (3S)-3-Amino-4-cyclohexyl-butyric acid
H-$\beta^3$-HC$_4$al-OH (3S)-3-Amino-4-cyclobutyl-butyric acid
H-$\beta^3$-HC$_5$al-OH (3S)-3-Amino-4-cyclopentyl-butyric acid
H-$\beta^3$-HNle-OH (3S)-3-Amino-heptanoic acid
H-$\beta^3$-H2Nal-OH (3S)-3-Amino-4-(2'-naphthyl)-butyric acid
H-$\beta^3$-H1Nal-OH (3S)-3-Amino-4-(1'-naphthyl)-butyric acid
H-$\beta^3$-H4ClPhe-OH (3S)-3-Amino-4-(4'-chlorophenyl)-butyric acid
H-$\beta^3$-H3ClPhe-OH (3S)-3-Amino-4-(3'-chlorophenyl)-butyric acid
H-$\beta^3$-H2ClPhe-OH (3S)-3-Amino-4-(2'-chlorophenyl)-butyric acid
H-$\beta^3$-H3,4Cl$_2$Phe-OH (3S)-3-Amino-4-(3',4'-dichlorophenyl)-butyric acid
H-$\beta^3$-H4FPhe-OH (3S)-3-Amino-4-(4'-fluorophenyl)-butyric acid
H-$\beta^3$-H3FPhe-OH (3S)-3-Amino-4-(3'-fluorophenyl)-butyric acid
H-$\beta^3$-H2FPhe-OH (3S)-3-Amino-4-(2'-fluorophenyl)-butyric acid
H-$\beta^3$-HThi-OH (3R)-3-Amino-4-(2'-thienyl)-butyric acid
H-$\beta^3$-HTza-OH (3R)-3-Amino-4-(2'-thiazolyl)-butyric acid
H-$\beta^3$-HMso-OH (3R)-3-Amino-4-methylsulfoxyl-butyric acid
H-$\beta^3$-HAcLys-OH (3S)-7-Acetylamino-3-amino-heptanoic acid
H-$\beta^3$-HDpr-OH (3R)-3,4-diamino-butyric acid
H-$\beta^3$-HA$_2$Bu-OH (3S)-3,5-Diamino-pentanoic acid
H-$\beta^3$-HDbu-OH (3R)-3,4-Diamino-pentanoic acid
H-$\beta^3$-HAib-OH Amino-dimethyl-acetic acid
H-$\beta^3$-HCyp-OH 1-Amino-cyclopentane-1-yl-acetic acid
H-$\beta^3$-HY(Bzl)-OH (3S)-3-Amino-4-(4'-benzyloxyphenyl)-butyric acid
H-$\beta^3$-HH(Bzl)-OH (3S)-3-Amino-4-(1'-benzylimidazole-4'-yl)-butyric acid
H-$\beta^3$-HBip-OH (3S)-3-Amino-4-biphenylyl-butyric acid
H-$\beta^3$-HS(Bzl)-OH (3S)-3-Amino-4-(benzyloxy)-butyric acid H-β³-HT(Bzl)-OH (3R,4R)-3-Amino-4-benzyloxy-pentanoic acid
H-β³-HalloT-OH (3R,4S)-3-Amino-4-hydroxy-pentanoic acid
H-β³-HLeu3OH-OH (3R,4R)-3-Amino-4-hydroxy-5-methyl-hexanoic acid
H-β³-HhAla-OH (3S)-3-Amino-pentanoic acid
H-β³-HhArg-OH (3S)-3-Amino-7-guanidino-heptanoic acid
H-β³-HhCys-OH (3R)-Amino-5-mercapto-pentanoic acid
H-β³-HhGlu-OH (3S)-3-Amino-heptanedioic acid
H-β³-HhGln-OH (3S)-3-Amino-6-carbamoyl-hexanoic acid
H-β³-HhHis-OH (3S)-3-Amino-5-(imidazole-4'-yl)-pentanoic acid
H-β³-HhIle-OH (3S,5S)-3-Amino-5-methyl-heptanoic acid
H-β³-HhLeu-OH (3S)-3-Amino-6-methyl-heptanoic acid
H-β³-HhNle-OH (3S)-3-Amino-octanoic acid
H-β³-DiAoc-OH (3S)-3,8-Diamino-octanoic acid
H-β³-HhMet-OH (3S)-3-Amino-6-methylthio-hexanoic acid
H-β³-HhPe-OH (3S)-3-Amino-5-phenyl-pentanoic acid
H-β³-HhSer-OH (3S)-3-Amino-5-hydroxy-pentanoic acid
H-β³-HhThr-OH (3S,5R)-3-Amino-5-hydroxy-hexanoic acid
H-β³-HhTrp-OH (3S)-3-Amino-5-(indol-3'-yl)-pentanoic acid
H-β³-HhThr-OH (3S)-3-Amino-5-(4'-hydroxyphenyl)-pentanoic acid
H-β³-HhCha-OH (3S)-3-Amino-5-cyclohexyl-pentanoic acid
H-β³-HBpa-OH (3S)-3-Amino-4-(4'-benzoylphenyl)-butyric acid
H-β³-HOctG-OH (3S)-3-Amino-undecanoic acid
H-β³-HNle-OH (3S)-3-Amino-heptanoic acid
H-β³-HTic-OH (3S)-1,2,3,4-Tetrahydroisoquinoline-3-yl-acetic acid
H-β³-HTiq-OH (1S)-1,2,3,4-Tetrahydroisoquinoline-1-acetic acid
H-β³-HOic-OH (2S,3aS, 7aS)-1-Octahydro-1H-indole-2-yl-acetic acid
H-β³-H4AmPyrr1-OH (2S,4S)-4-Amino-pyrrolidine-2-acetic acid
H-β³-H4AmPyrr2-OH (2S,4R)-4-Amino-pyrrolidine-2-acetic acid
H-β³-H4PhePyrr1-OH (2S,4R)-4-Phenyl-pyrrolidine-2-acetic acid
H-β³-H4PhePyrr2-OH (2S,4S)-4-Phenyl-pyrrolidine-2-acetic acid
H-β³-H5PhePyrr1-OH (2S,5R)-5-Phenyl-pyrrolidine-2-acetic acid
H-β³-H5PhePyrr2-OH (2S,5S)-5-Phenyl-pyrrolidine-2-acetic acid
H-β³-H4Hyp1-OH (2S,4S)-4-Hydroxy-pyrrolidine-2-acetic acid
H-β³-H4Hyp2-OH (2S,4R)-4-Hydroxy-pyrrolidine-2-acetic acid
H-β³-H4 Mp1-OH (2R,4S)-4-Mercapto-pyrrolidine-2-acetic acid
H-β³-H4 Mp2-OH (2R,4R)-4-Mercapto-pyrrolidine-2-acetic acid
H-β³-HPip-OH (2S)-piperidine-2-acetic acid
H-β³-HPro-OH (2S)-pyrrolidine-2-acetic acid
H-β³-H$^D$Pro-OH (2R)-pyrrolidine-2-acetic acid
Ahb 4-Amino-2-hydroxy-butyric acid
H-γ⁴-DiHCit-OH (4S)-4-Amino-7-carbamidyl-heptanoic acid
H-γ⁴-DiHOrn-OH (4S)-4,7-Diamino-heptanoic acid
H-γ⁴-DiHtBuA-OH (4R)-4-Amino-6,6-dimethyl-heptanoic acid
H-γ⁴-DiHSar-OH N-Methyl-4-amino-butyric acid
H-γ⁴-DiHPen-OH (4R)-4-Amino-5-methyl-5-mercapto-hexanoic acid
H-γ⁴-DiHtBuG-OH (4R)-4-Amino-5,5-dimethyl-hexanoic acid
H-γ⁴-DiH4AmPhe-OH (4R)-4-Amino-5-(4'-aminophenyl)-pentanoic acid
H-γ⁴-DiH3AmPhe-OH (4R)-4-Amino-5-(3'-aminophenyl)-pentanoic acid
H-γ⁴-DiH2AmPhe-OH (4R)-4-Amino-5-(2'-aminophenyl)-pentanoic acid
H-γ⁴-DiHPhe (mC(NH$_2$)=NH)—OH (4R)-4-Amino-5-(3'-amidinophenyl)-pentanoic acid
H-γ⁴-DiHPhe (pC(NH$_2$)=NH)—OH (4R)-4-Amino-5-(4'-amidinophenyl)-pentanoic acid
H-γ⁴-DiHPhe (mNHC(NH$_2$)=NH)—OH (4R)-4-Amino-5-(3'-guanidino-phenyl)-pentanoic acid
H-γ⁴-DiHPhe (pNHC(NH$_2$)=NH)—OH (4R)-4-Amino-5-(4'-guanidino-phenyl)-pentanoic acid
H-γ⁴-DiH2 Pal-OH (4R)-4-Amino-5-(pyridine-4'-yl)-pentanoic acid
H-γ⁴-DiH4 Pal-OH (4R)-4-Amino-5-(pyridine-4'-yl)-pentanoic acid
H-γ⁴-DiHPhg-OH (4R)-4-Amino-4-phenyl-butyric acid
H-γ⁴-DiHCha-OH (4R)-4-Amino-5-cyclohexyl-pentanoic acid
H-γ⁴-DiHC₄al-OH (4R)-4-Amino-5-cyclobutyl-pentanoic acid
H-γ⁴-DiHC₅al-OH (4R)-4-Amino-5-cyclopentyl-pentanoic acid
H-γ⁴-DiHNle-OH (4S)-4-Amino-octanoic acid
H-γ⁴-DiH2Nal-OH (4S)-4-Amino-5-(2'-naphthyl)-pentanoic acid
H-γ⁴-DiH1Nal-OH (4S)-4-Amino-5-(1'-naphthyl)-pentanoic acid
H-γ⁴-DiH4ClPhe-OH (4R)-4-Amino-5-(4'-chlorophenyl)-pentanoic acid
H-γ⁴-DiH3ClPhe-OH (4R)-4-Amino-5-(3'-chlorophenyl)-pentanoic acid
H-γ⁴-DiH2ClPhe-OH (4R)-4-Amino-5-(2'-chlorophenyl)-pentanoic acid
H-γ⁴-DiH3,4Cl₂Phe-OH (4R)-4-Amino-5-(3',4'-dichloro-phenyl)-pentanoic acid
H-γ⁴-DiH4FPhe-OH (4R)-4-Amino-5-(4'-fluorophenyl)-pentanoic acid
H-γ⁴-DiH3FPhe-OH (4R)-4-Amino-5-(3'-fluorophenyl)-pentanoic acid
H-γ⁴-DiH2FPhe-OH (4R)-4-Amino-5-(2'-fluorophenyl)-pentanoic acid
H-γ⁴-DiHThi-OH (4R)-4-Amino-5-(2'-thienyl)-pentanoic acid
H-γ⁴-DiHTza-OH (4R)-4-Amino-5-(2'-thiazolyl)-pentanoic acid
H-γ⁴-DiHMso-OH (4R)-4-Amino-5-methylsulfoxyl-pentanoic acid
H-γ⁴-DiHAcLys-OH (4S)-8-Acetylamino-4-amino-ocatanoic acid
H-γ⁴-DiHDpr-OH (4R)-4,5-diamino-pentanoic acid
H-γ⁴-DiHA₂Bu-OH (4R)-4,5-Diamino-hexanoic acid
H-γ⁴-DiHDbu-OH (4R)-4,5-Diamion-hexanoic acid
H-γ⁴-DiHAib-OH 3-Amino-3,3-dimethyl-propionic acid
H-γ⁴-DiHCyp-OH (1'-Amino-cyclopentane-1'-yl)-3-propionic acid
H-γ⁴-DiHY(Bzl)-OH (4R)-4-Amino-5-(4'-benzyloxyphenyl)-pentanoic acid
H-γ⁴-DiHH(Bzl)-OH (4R)-4-Amino-5-(1'-benzylimidazole-4'-yl)-pentanoic acid H-γ⁴-DiHBip-OH (4R)-4-Amino-5-biphenylyl-pentanoic acid
H-γ⁴-DiHS (Bzl)-OH (4S)-4-Amino-5-(benzyloxy)-pentanoic acid
H-γ⁴-DiHT(Bzl)-OH (4R,5R)-4-Amino-5-benzyloxy-hexanoic acid
H-γ⁴-DiHalloT-OH (4R,5S)-4-Amino-5-hydroxy-hexanoic acid
H-γ⁴-DiHLeu3OH—OH (4R,5R)-4-Amino-5-hydroxy-6-methyl-heptanoic acid
H-γ⁴-DiHhAla-OH (4S)-4-Amino-hexanoic acid
H-γ⁴-DiHhArg-OH (4S)-4-Amino-8-guanidino-octanoic acid
H-γ⁴-DiHhCys-OH (4R)-Amino-6-mercapto-hexanoic acid
H-γ⁴-DiHhGlu-OH (4S)-4-Amino-octanedioic acid
H-γ⁴-DiHhGln-OH (4S)-4-Amino-7-carbamoyl-heptanoic acid
H-γ⁴-DiHhHis-OH (4S)-4-Amino-6-(imidazole-4'-yl)-hexanoic acid
H-γ⁴-DiHhIle-OH (4S,6S)-4-Amino-6-methyl-octanoic acid
H-γ⁴-DiHhLeu-OH (4S)-4-Amino-7-methyl-ocatanoic acid
H-γ⁴-DiHhNle-OH (4S)-4-Amino-nonanoic acid
H-γ⁴-DiHhLys-OH (4S)-4,9-Diamino-nonanoic acid
H-γ⁴-DiHhMet-OH (4R)-4-Amino-7-methylthioheptanoic acid
H-γ⁴-DiHhPhe-OH (4S)-4-Amino-6-phenyl-hexanoic acid
H-γ⁴-DiHhSer-OH (4R)-4-Amino-6-hydroxy-hexanoic acid
H-γ⁴-DiHhThr-OH (4R,6R)-4-Amino-6-hydroxy-heptanoic acid
H-γ⁴-DiHhTrp-OH (4S)-4-Amino-6-(indol-3'-yl)-hexanoic acid
H-γ⁴-DiHhTyr-OH (4S)-4-Amino-6-(4'-hydroxyphenyl)-hexanoic acid
H-γ⁴-DiHhCha-OH (4R)-4-Amino-5-cyclohexyl-pentanoic acid
H-γ⁴-DihBpa-OH (4R)-4-Amino-5-(4'-benzoylphenyl)-pentanoic acid
H-γ⁴-DiHOctG-OH (4S)-4-Amino-dodecanoic acid
H-γ⁴-DiHNle-OH (4S)-4-Amino-octanoic acid
H-γ⁴-DiHTic-OH (3R)-1',2',3',4'-Tetrahydroisoquinoline-3'-yl-3-propionic acid
H-γ⁴-DiHTiq-OH (1'R)-1',2',3',4'-Tetrahydroisoquinoline-1'-yl-3-propionic acid
H-γ⁴-DiHOic-OH (2'S, 3' aS, 7' aS)-1'-Octahydro-1H-indole-2'-yl-3-propionic acid
H-γ⁴-DiH4AmPyrr1-OH (2'R, 4'S)-4'-Amino-pyrrolidine-2'-yl-3-propionic acid
H-γ⁴-DiH4AmPyrr2-OH (2'R, 4'R)-4'-Amino-pyrrolidine-2'-yl-3-propionic acid
H-γ⁴-DiH4PhePyrr1-OH (2'R, 4'R)-4'-Phenyl-pyrrolidine-2'-yl-3-propionic acid
H-γ⁴-DiH4PhePyrr2-OH (2'R, 4'S)-4'-Phenyl-pyrrolidine-2'-yl-3-propionic acid
H-γ⁴-DiH5PhePyrr1-OH (2'S, 5'R)-5'-Phenyl-pyrrolidine-2'-yl-3-propionic acid
H-γ⁴-DiH5PhePyrr2-OH (2'S, 5'S)-5'-Phenyl-pyrrolidine-2'-yl-3-propionic acid
H-γ⁴-DiH4Hyp1-OH (2'R, 4'S)-4'-Hydroxy-pyrrolidine-2'-yl-2-propionic acid
H-γ⁴-DiH4Hyp2-OH (2'R, 4'R)-4'-Hydroxy-pyrrolidine-2'-yl-3-propionic acid
H-γ⁴-DiH4 Mp1-OH (2'R, 4'S)-4'-Mercapto-pyrrolidine-2'-yl-3-propionic acid
H-γ⁴-DiH4 Mp2-OH (2'R, 4'R)-4'-Mercapto-pyrrolidine-2'-yl-3-propionic acid
H-γ⁴-DiHPip-OH (2'S)-Piperidine-2'-yl-3-propionic acid
H-γ⁴-DiHPro-OH (2'S)-Pyrrolidine-2'-yl-3-propionic acid
H-γ⁴-DiH^DPro-OH (2'R)-Pyrrolidine-2'-yl-3-propionic acid
(AEt)G N-(2-Aminoethyl)glycine
(APr)G N-(3-Amino-n-propyl)glycine
(ABu)G N-(4-Amino-n-butyl)glycine
(APe)G N-(5-Amino-n-pentyl)glycine
(GuEt) G N-(2-Guanidinoethyl)glycine
(GuPr)G N-(3-Guanidino-n-propyl)glycine
(GuBu)G N-(4-Guanidino-n-butyl)glycine
(GuPe)G N-(5-Guanidino-n-pentyl)glycine
(PEG₃-NH₂)G N—[H₂N—(CH₂)₃—(OCH₂—CH₂)₂—O(CH₂)₃]glycine
(Me)G N-Methylglycine
(Et)G N-Ethylglycine
(Bu)G N-Butylglycine
(Pe)G N-Pentylglycine
(Ip)G N-Isopropylglycine
(2MePr)G N-(2-Methylpropyl)glycine
(3MeBu)G N-(3-Methylbutyl)glycine
(1MePr)G (1S)—N-(1-Methylpropyl)glycine
(2MeBu)G (2S)—N-(2-Methylbutyl)glycine
(MthEt)G N-(Methylthioethyl)glycine
(MthPr)G N-(Methylthiopropyl)glycine
(Ben) G N-(Benzyl) glycine
(PhEt)G N-(2-Phenylethyl)glycine
(HphMe)G N-([4'-hydroxyphenyl]methyl)glycine
(HphEt)G N-(2-[4'-hydroxyphenyl]ethyl)glycine
(ImMe)G N-(Imidazol-5-yl-methyl)glycine
(ImEt)G N-(2-(Imidazol-5'-yl)ethyl)glycine
(InMe)G N-(Indol-2-yl-methyl)glycine
(InEt)G N-(2-(Indol-2'-yl)ethyl)glycine
(CboMe)G N-(Carboxymethyl)glycine
(CboEt)G N-(2-Carboxyethyl)glycine
(CboPr)G N-(3-Carboxypropyl)glycine
(CbaMe)G N-(Carbamoylmethyl)glycine
(CbaEt)G N-(2-Carbamoylethyl)glycine
(CbaPr)G N-(3-Carbamoylpropyl)glycine
(HyEt)G N-(2-Hydroxyethyl)glycine
(HyPr)G (2R)—N-(2-Hydroxypropyl)glycine
(Mcet)G N-(2-Mercaptoethyl)glycine
NMeAla L-N-Methylalanine
NMe^DAla D-N-Methylalanine
NMeVal L-N-Methylvaline
NMe^DVal D-N-Methylvaline
NMeIle L-N-Methylisoleucine
NMe^DIle D-N-Methylisoleucine
NMeLeu L-N-Methylleucine
NMe^DLeu D-N-Methylleucine
NMeNle L-N-Methylnorleucine
NMe^DNle D-N-Methylnorleucine
NMeMet L-N-Methylmethionine
NMe^DMet D-N-Methylmethionine
NMeTyr L-N-Methyltyrosine
NMe^DTyr D-N-Methyltyrosine
NMeHis L-N-Methylhistidine
NMe^DHis D-N-Methylhistidine
NMePhe L-N-Methylphenylalanine
NMe^DPhe D-N-Methylphenylalanine
NMeTrp L-N-Methyltryptophane
NMe^DTrp D-N-Methyltryptophane
NMeSer L-N-Methylserine
NMe^DSer D-N-Methylserine
NMeAsp L-N-Methylaspartic acid
NMe^DAsp D-N-Methylaspartic acid
NMeGlu L-N-Methylglutamic acid
NMe^DGlu D-N-Methylglutamic acid
NMeLys L-N-Methyllysine
NMe^DLys D-N-Methyllysine NMeArg L-N-Methylarginine
NMe$^D$Arg D-N-Methylarginine
NMeDab L-N-Methyl-2,4-diamino butyric acid
NMe$^D$Dab D-N-Methyl-2,4-diamino butyric acid
NMeCys L-N-Methylcysteine
NMe$^D$Cys D-N-Methylcysteine
NMeAsn L-N-Methylasparagine
NMe$^c$Asn D-N-Methylasparagine
NMeGln L-N-Methylglutamine
NMe$^D$Gln D-N-Methylglutamine
NMeThr L-N-Methylthreonine
NMe$^D$Thr D-N-Methylthreonine
    Particularly preferred residues for group C are:
Ala L-Alanine
$^D$Ala D-Alanine
Ile L-Isoleucine
$^D$Ile D-Isoleucine
Leu L-Leucine
$^D$Leu D-Leucine
Met L-Methionine
$^D$Met D-Methionine
Val L-Valine
$^D$Val D-Valine
tBuA L-t-Butylalanine
$^D$tBuA D-t-Butylalanine
tBuG L-tert.-Butylglycine
$^D$tBuG D-tert.-Butylglycine
Cha L-Cyclohexylalanine
$^D$Cha D-Cyclohexylalanine
C$_4$al L-3-Cyclobutylalanine
$^D$C$_4$al D-3-Cyclobutylalanine
C$_5$al L-3-Cyclopentylalanine
$^D$C$_5$al D-3-Cyclopentylalanine
Nle L-Norleucine
$^D$Nle D-Norleucine
hAla L-Homo-alanine
$^D$hAla D-Homo-alanine
hIle L-Homo-isoleucine
$^D$hIle D-Homo-isoleucine
hLeu L-Homo-leucine
$^D$hLeu D-Homo-leucine
hMet L-Homo-Methionine
$^D$hMet D-Homo-Methionine
hVal L-Homo-valine
$^D$hVal D-Homo-valine
hCha L-Homo-cyclohexylalanine
$^D$hCha D-Homo-cyclohexylalanine
OctG L-Octylglycine
$^D$OctG D-Octylglycine
NMeAla L-N-Methylalanine
NMe$^D$Ala D-N-Methylalanine
NMeVal L-N-Methylvaline
NMe$^D$Val D-N-Methylvaline
NMeIle L-N-Methylisoleucine
NMe$^D$Ile D-N-Methylisoleucine
NMeLeu L-N-Methylleucine
NMe$^D$Leu D-N-Methylleucine
NMeNle L-N-Methylnorleucine
NMe$^D$Nle D-N-Methylnorleucine
NMeNle L-N-Methylnorleucine
NMe$^D$Nle D-N-Methylnorleucine
NMeMet L-N-Methylmethionine
NMe$^D$Met D-N-Methylmethionine
    Particularly preferred residues for group D are:
His L-Histidine
$^D$His D-Histidine
Phe L-Phenylalanine
$^D$Phe D-Phenylalanine
Trp L-Tryptophan
$^D$Trp D-Tryptophan
Tyr L-Tyrosine
$^D$Tyr D-Tyrosine
2 Pal (2S)-2-Amino-3-(pyridine-2'-yl)-propionic acid
$^D$2 Pal (2R)-2-Amino-3-(pyridine-2'-yl)-propionic acid
4 Pal (2S)-2-Amino-3-(pyridine-4'-yl)-propionic acid
$^D$4 Pal (2R)-2-Amino-3-(pyridine-4'-yl)-propionic acid
Phg L-Phenylglycine
$^D$Phg D-Phenylglycine
2NaI L-2-Naphthylalanine
$^D$2NaI D-2-Naphthylalanine
1Nal L-1-Naphthylalanine
$^D$1Nal D-1-Naphthylalanine
4ClPhe L-4-Chlorophenylalanine
$^D$4ClPhe D-4-Chlorophenylalanine
3ClPhe L-3-Chlorophenylalanine
$^D$3ClPhe D-3-Chlorophenylalanine
2ClPhe L-2-Chlorophenylalanine
$^D$2ClPhe D-2-Chlorophenylalanine
3,4Cl$_2$Phe L-3,4-Dichlorophenylalanine
$^D$3,4Cl$_2$Phe D-3,4-Dichlorophenylalanine
4FPhe L-4-Fluorophenylalanine
$^D$4FPhe D-4-Fluorophenylalanine
3FPhe L-3-Fluorophenylalanine
$^D$3FPhe D-3-Fluorophenylalanine
2FPhe L-2-Fluorophenylalanine
$^D$2FPhe D-2-Fluorophenylalanine
Thi L-β-2-Thienylalanine
$^D$Thi D-β-2-Thienylalanine
Tza L-2-Thiazolylalanine
$^D$Tza D-2-Thiazolylalanine
Tyr(Bzl) L-O-Benzyltyrosine
$^D$Tyr(Bzl) D-O-Benzyltyrosine
His(Bzl) (3S)-2-Amino-3-(1'-benzylimidazole-4'-yl)-propionic acid
$^D$His(Bzl) (3R)-2-Amino-3-(1'-benzylimidazole-4'-yl)-propionic acid
Bip L-(4-phenyl)phenylalanine
$^D$Bip D-(4-phenyl)phenylalanine
Ser(Bzl) L-O-Benzylserine
$^D$Ser(Bzl) D-O-Benzylserine
Thr(Bzl) L-O-Benzylthreonine
$^D$Thr(Bzl) D-O-Benzylthreonine
hPhe L-Homo-phenylalanine
$^D$hPhe D-Homo-phenylalanine
hTrp L-Homo-tryptophan
$^D$hTrp D-Homo-tryptophan
hTyr L-Homo-tyrosine
$^D$hTyr D-Homo-tyrosine
hHis L-Homo-histidine
$^D$hHis D-Homo-histidine
Bpa L-4-Benzoylphenylalanine
$^D$Bpa D-4-Benzoylphenylalanine
NMePhe L-N-Methylphenylalanine
NMe$^D$Phe D-N-Methylphenylalanine
NMeTyr L-N-Methyltyrosine
NMe$^D$Tyr D-N-Methyltyrosine
NMeHis L-N-Methylhistidine
NMe$^D$His D-N-Methylhistidine
NMeTrp L-N-Methyltryptophane
NMe$^D$Trp D-N-Methyltryptophane
    Particularly preferred residues for group E are
Arg L-Arginine
$^D$Arg D-Arginine
Lys L-Lysine <sup>D</sup>Lys D-Lysine
Orn L-Ornithine
<sup>D</sup>Orn D-Ornithine
Dpr L-2,3-Diaminopropionic acid
<sup>D</sup>Dpr D-2,3-Diaminopropionic acid
A$_2$Bu L-2,4-Diaminobutyric acid
<sup>D</sup>A$_2$Bu (2R)-2,4-Diaminobutyric acid
Dab L-2,4-Diaminobutyric acid
<sup>D</sup>Dab D-2,4-Diaminobutyric acid
Dbu (2S,3S)-2,3-Diaminobutyric acid
<sup>D</sup>Dbu (2R)-2,3-Diamino-butyric acid
4AmPhe L-para-Aminophenylalanine
<sup>D</sup>4AmPhe D-para-Aminophenylalanine
3AmPhe L-meta-Aminophenylalanine
<sup>D</sup>3AmPne D-meta-Aminophenylalanine
2AmPhe L-ortho-Aminophenylalanine
<sup>D</sup>2AmPhe D-ortho-Aminophenylalanine
Phe(mC(NH$_2$)=NH) L-meta-Amidinophenylalanine
<sup>D</sup>Phe(mC(NH$_2$)=NH) D-meta-Amidinophenylalanine
Phe(pC(NH$_2$)=NH) L-para-Amidinophenylalanine
<sup>D</sup>Phe(pC(NH$_2$)=NH) D-para-Amidinophenylalanine
Phe(mNHC(NH$_2$)=NH) L-meta-Guanidinophenylalanine
<sup>D</sup>Phe(mNHC(NH$_2$)=NH) D-meta-Guanidinophenylalanine
Phe(pNHC(NH$_2$)=NH) L-para-Guanidinophenylalanine
<sup>D</sup>Phe(pNHC(NH$_2$)=NH) D-para-Guanidinophenylalanine
hArg L-Homo-arginine
<sup>D</sup>hArg D-Homo-arginine
hLys L-Homo-lysine
<sup>D</sup>hLys D-Homo-lysine
NMeLys L-N-Methyllysine
NMe<sup>D</sup>Lys D-N-Methyllysine
NMeArg L-N-Methylarginine
NMe<sup>D</sup>Arg D-N-Methylarginine
NMeDab L-N-Methyl-2,4-diamino butyric acid
NMe<sup>D</sup>Dab D-N-Methyl-2,4-diamino butyric acid
  Particularly preferred residues for group F are
Asn L-Asparagine
<sup>D</sup>Asn D-Asparagine
Asp L-Aspartic acid
<sup>D</sup>Asp D-Aspartic acid
Cys L-Cysteine
<sup>D</sup>Cys D-Cysteine
Gln L-Glutamine
<sup>D</sup>Gln D-Glutamine
Glu L-Glutamic acid
<sup>D</sup>Glu D-Glutamic acid
Ser L-Serine
<sup>D</sup>Ser D-Serine
Thr L-Threonine
<sup>D</sup>Thr D-Threonine
Cit L-Citrulline
<sup>D</sup>Cit D-Citrulline
Pen L-Penicillamine
<sup>D</sup>Pen D-Penicillamine
AcLys L-N'-Acetyllysine
<sup>D</sup>AcLys N-Acetyl-D-lysine
alloT (2S,3S)-2-Amino-3-hydroxy-butyric acid
<sup>D</sup>alloT (2R,3S)-2-Amino-3-hydroxy-butyric acid
Leu3OH (2S,3R)-2-Amino-3-hydroxy-4-methyl-pentanoic acid
<sup>D</sup>Leu3OH (2R,3R)-2-Amino-3-hydroxy-4-methyl-pentanoic acid
hCys L-Homo-cysteine
<sup>D</sup>hCys D-Homo-cysteine
hSer L-Homo-serine
<sup>D</sup>hSer D-Homo-serine
hGlu L-Homo-glutamic acid
<sup>D</sup>hGlu D-glutamic acid
hGln L-Homo-glutamine
<sup>D</sup>hGln D-Homo-glutamine
hThr L-Homo-threonine
<sup>D</sup>hThr D-Homo-threonine
NMeSer L-N-Methylserine
NMe<sup>D</sup>Ser D-N-Methylserine
NMeAsp L-N-Methylaspartic acid
NMe<sup>D</sup>Asp D-N-Methylaspartic acid
NMeGlu L-N-Methylglutamic acid
NMe<sup>D</sup>Glu D-N-Methylglutamic acid
NMeCys L-N-Methylcysteine
NMe<sup>D</sup>Cys D-N-Methylcysteine
NMeAsn L-N-Methylasparagine
NMe<sup>c</sup>Asn D-N-Methylasparagine
NMeGln L-N-Methylglutamine
NMe<sup>D</sup>Gln D-N-Methylglutamine
NMeThr L-N-Methylthreonine
NMe<sup>D</sup>Thr D-N-Methylthreonine
  Particularly preferred residues for group I are
(AEt)G N-(2-Aminoethyl)glycine
(APr)G N-(3-Amino-n-propyl)glycine
(ABu)G N-(4-Amino-n-butyl)glycine
(APe)G N-(5-Amino-n-pentyl)glycine
(GuEt)G N-(2-Guanidinoethyl)glycine
(GuPr) G N-(3-Guanidino-n-propyl) glycine
(GuBu)G N-(4-Guanidino-n-butyl)glycine
(GuPe)G N-(5-Guanidino-n-pentyl)glycine
(PEG$_3$-NH$_2$)G  N—[H$_2$N—(CH$_2$)$_3$—(OCH$_2$—CH$_2$)$_2$—O(CH$_2$)$_3$]glycine
(Me)G N-Methylglycine
(Et)G N-Ethylglycine
(Bu)G N-Butylglycine
(Pe)G N-Pentylglycine
(Ip)G N-Isopropylglycine
(2MePr)G N-(2-Methylpropyl)glycine
(3MeBu)G N-(3-Methylbutyl)glycine
(1MePr)G (1S)—N-(1-Methylpropyl)glycine
(2MeBu)G (2S)—N-(2-Methylbutyl)glycine
(MthEt)G N-(Methylthioethyl)glycine
(MthPr)G N-(Methylthiopropyl)glycine
(Ben) G N-(Benzyl)glycine
(PhEt)G N-(2-Phenylethyl)glycine
(HphMe)G N-([4'-hydroxyphenyl]methyl)glycine
(HphEt)G N-(2-[4'-hydroxyphenyl]ethyl)glycine
(ImMe)G N-(Imidazol-5-yl-methyl)glycine
(ImEt)G N-(2-(Imidazol-5'-yl)ethyl)glycine
(InMe)G N-(Indol-2-yl-methyl)glycine
(InEt)G N-(2-(Indol-2'-yl)ethyl)glycine
(CboMe)G N-(Carboxymethyl)glycine
(CboEt)G N-(2-Carboxyethyl)glycine
(CboPr)G N-(3-Carboxypropyl)glycine
(CbaMe)G N-(Carbamoylmethyl)glycine
(CbaEt)G N-(2-Carbamoylethyl)glycine
(CbaPr)G N-(3-Carbamoylpropyl)glycine
(HyEt)G N-(2-Hydroxyethyl)glycine
(HyPr)G (2R)—N-(2-Hydroxypropyl)glycine
(Mcet)G N-(2-Mercaptoethyl)glycine
  Particularly preferred residues for group M are
Ahb 4-Amino-2-hydroxy-butyric acid
H-γ$^4$-DihAla-OH (4S)-4-Amino-pentanoic acid
H-γ$^4$-DihVal-OH (4R)-4-Amino-5-methyl-hexanoic acid
H-γ$^4$-DihIle-OH (4R,5S)-4-Amino-5-methyl-heptanoic acid
H-γ$^4$-DihLeu-OH (4R)-4-Amino-6-methyl-heptanoic acid
H-γ$^4$-DihMet-OH (4R)-4-Amino-6-methylthio-hexanoic acid H-γ⁴-DihTyr-OH (4R)-4-Amino-5-(4'-hydroxyphenyl)-pentanoic acid
H-γ⁴-DihHis-OH (4R)-4-Amino-5-(imidazole-4'-yl)-pentanoic acid
H-γ⁴-DihPhe-OH (4R)-4-Amino-5-phenyl-pentanoic acid
H-γ⁴-DiTrp-OH (4R)-4-Amino-5-(indol-3'-yl)-pentanoic acid
H-γ⁴-DihSer-OH (4R)-4-Amino-5-hydroxy-pentanoic acid
H-γ⁴-DihAsp-OH (4R)-4-Amino-hexanedioic acid
H-γ⁴-DihGlu-OH 4-Amino-heptanedioic acid
H-γ⁴-DihLys-OH (4S)-4,8-Diamino-octanoic acid
H-γ⁴-DihArg-OH (4S)-4-Amino-7-guanidino-heptanoic acid
H-γ⁴-DihCys-OH (4R)-4-Amino-5-mercapto-pentanoic acid
H-γ⁴-DihAsn-OH (4R)-4-Amino-5-carbamoyl-pentanoic acid
H-γ⁴-DihGln-OH (3S)-3-Amino-5-carbamoyl-hexanoic acid
H-γ⁴-DihThr-OH (4R,5R)-4-Amino-5-hydroxy-hexanoic acid
H-γ⁴-DiHCit-OH (4S)-4-Amino-7-carbamidyl-heptanoic acid
H-γ⁴-DiHOrn-OH (4S)-4,7-Diamino-heptanoic acid
H-γ⁴-DiHtBuA-OH (4R)-4-Amino-6,6-dimethyl-heptanoic acid
H-γ⁴-DiHSar-OH N-Methyl-4-amino-butyric acid
H-γ⁴-DiHPen-OH (4R)-4-Amino-5-methyl-5-mercapto-hexanoic acid
H-γ⁴-DiHtBuG-OH (4R)-4-Amino-5,5-dimethyl-hexanoic acid
H-γ⁴-DiH4AmPhe-OH (4R)-4-Amino-5-(4'-aminophenyl)-pentanoic acid
H-γ⁴-DiH3AmPhe-OH (4R)-4-Amino-5-(3'-aminophenyl)-pentanoic acid
H-γ⁴-DiH2AmPhe-OH (4R)-4-Amino-5-(2'-aminophenyl)-pentanoic acid
H-γ⁴-DiHPhe (mC(NH₂)=NH)—OH (4R)-4-Amino-5-(3'-amidinophenyl)-pentanoic acid
H-γ⁴-DiHPhe (pC(NH₂)=NH)—OH (4R)-4-Amino-5-(4'-amidinophenyl)-pentanoic acid
H-γ⁴-DiHPhe (mNHC(NH₂)=NH)—OH (4R)-4-Amino-5-(3'-guanidino-phenyl)-pentanoic acid
H-γ⁴-DiHPhe (pNHC(NH₂)=NH)—OH (4R)-4-Amino-5-(4'-guanidino-phenyl)-pentanoic acid
H-γ⁴-DiH2 Pal-OH (4R)-4-Amino-5-(pyridine-4'-yl)-pentanoic acid
H-γ⁴-DiH4 Pal-OH (4R)-4-Amino-5-(pyridine-4'-yl)-pentanoic acid
H-γ⁴-DiHPhg-OH (4R)-4-Amino-4-phenyl-butyric acid
H-γ⁴-DiHCha-OH (4R)-4-Amino-5-cyclohexyl-pentanoic acid
H-γ⁴-DiHC₄al-OH (4R)-4-Amino-5-cyclobutyl-pentanoic acid
H-γ⁴-DiHC₅al-OH (4R)-4-Amino-5-cyclopentyl-pentanoic acid
H-γ⁴-DiHNle-OH (4S)-4-Amino-octanoic acid
H-γ⁴-DiH2Nal-OH (4S)-4-Amino-5-(2'-naphthyl)-pentanoic acid
H-γ⁴-DiH1Nal-OH (4S)-4-Amino-5-(1'-naphthyl)-pentanoic acid
H-γ⁴-DiH4ClPhe-OH (4R)-4-Amino-5-(4'-chlorophenyl)-pentanoic acid
H-γ⁴-DiH3ClPhe-OH (4R)-4-Amino-5-(3'-chlorophenyl)-pentanoic acid
H-γ⁴-DiH2ClPhe-OH (4R)-4-Amino-5-(2'-chlorophenyl)-pentanoic acid
H-γ⁴-DiH3,4Cl₂Phe-OH (4R)-4-Amino-5-(3',4'-dichlorophenyl)-pentanoic acid
H-γ⁴-DiH4FPhe-OH (4R)-4-Amino-5-(4'-fluorophenyl)-pentanoic acid
H-γ⁴-DiH3FPhe-OH (4R)-4-Amino-5-(3'-fluorophenyl)-pentanoic acid
H-γ⁴-DiH2FPhe-OH (4R)-4-Amino-5-(2'-fluorophenyl)-pentanoic acid
H-γ⁴-DiHThi-OH (4R)-4-Amino-5-(2'-thienyl)-pentanoic acid
H-γ⁴-DiHTza-OH (4R)-4-Amino-5-(2'-thiazolyl)-pentanoic acid
H-γ⁴-DiHMso-OH (4R)-4-Amino-5-methylsulfoxyl-pentanoic acid
H-γ⁴-DiHAcLys-OH (4S)-8-Acetylamino-4-amino-ocatanoic acid
H-γ⁴-DiHDpr-OH (4R)-4,5-diamino-pentanoic acid
H-γ⁴-DiHA₂Bu-OH (4R)-4,5-Diamino-hexanoic acid
H-γ⁴-DiHDbu-OH (4R)-4,5-Diamion-hexanoic acid
H-γ⁴-DiHY(Bzl)-OH (4R)-4-Amino-5-(4'-benzyloxyphenyl)-pentanoic acid
H-γ⁴-DiHH(Bzl)-OH (4R)-4-Amino-5-(1'-benzylimidazole-4'-yl)-pentanoic acid
H-γ⁴-DiHBip-OH (4R)-4-Amino-5-biphenylyl-pentanoic acid
H-γ⁴-DiHS (Bzl)-OH (4S)-4-Amino-5-(benzyloxy)-pentanoic acid
H-γ⁴-DiHT(Bzl)-OH (4R,5R)-4-Amino-5-benzyloxy-hexanoic acid
H-γ⁴-DiHalloT-OH (4R,5S)-4-Amino-5-hydroxy-hexanoic acid
H-γ⁴-DiHLeu3OH—OH (4R,5R)-4-Amino-5-hydroxy-6-methyl-heptanoic acid
H-γ⁴-DiHhAla-OH (4S)-4-Amino-hexanoic acid
H-γ⁴-DiHhArg-OH (4S)-4-Amino-8-guanidino-octanoic acid
H-γ⁴-DiHhCys-OH (4R)-Amino-6-mercapto-hexanoic acid
H-γ⁴-DiHhGlu-OH (4S)-4-Amino-ocatanedioic acid
H-γ⁴-DiHhGln-OH (4S)-4-Amino-7-carbamoyl-heptanoic acid
H-γ⁴-DiHhHis-OH (4S)-4-Amino-6-(imidazole-4'-yl)-hexanoic acid
H-γ⁴-DiHhIle-OH (4S,6S)-4-Amino-6-methyl-octanoic acid
H-γ⁴-DiHhLeu-OH (4S)-4-Amino-7-methyl-ocatanoic acid
H-γ⁴-DiHhNle-OH (4S)-4-Amino-nonanoic acid
H-γ⁴-DiHhLys-OH (4S)-4,9-Diamino-nonanoic acid
H-γ⁴-DiHhMet-OH (4R)-4-Amino-7-methylthioheptanoic acid
H-γ⁴-DiHhPhe-OH (4S)-4-Amino-6-phenyl-hexanoic acid
H-γ⁴-DiHhSer-OH (4R)-4-Amino-6-hydroxy-hexanoic acid
H-γ⁴-DiHhThr-OH (4R,6R)-4-Amino-6-hydroxy-heptanoic acid
H-γ⁴-DiHhTrp-OH (4S)-4-Amino-6-(indol-3'-yl)-hexanoic acid
H-γ⁴-DiHhTyr-OH (4S)-4-Amino-6-(4'-hydroxyphenyl)-hexanoic acid
H-γ⁴-DiHhCha-OH (4R)-4-Amino-5-cyclohexyl-pentanoic acid
H-γ⁴-DihBpa-OH (4R)-4-Amino-5-(4'-benzoylphenyl)-pentanoic acid
H-γ⁴-DiHOctG-OH (4S)-4-Amino-dodecanoic acid
H-γ⁴-DiHNle-OH (4S)-4-Amino-octanoic acid
Particularly preferred residues for group N are:
H-β³-HAla-OH (3S)-3-Amino-butyric acid
H-β³-HVal-OH (3R)-3-Amino-4-methyl-valeric acid
H-β³-HIle-OH (3R,4S)-3-Amino-4-methyl-hexanoic acid
H-β³-HLeu-OH (3S)-3-Amino-5-methyl-hexanoic acid
H-β³-HMet-OH (3S)-3-Amino-5-methylthio pentanoic acid H-β³-HTyr-OH (3S)-3-Amino-4-(4'-hydroxyphenyl)-butyric acid
H-β³-HHis-OH (3S)-3-Amino-4-(imidazole-4'-yl)-butyric acid
H-β³-HPhe-OH (3S)-3-Amino-4-phenyl-butyric acid
H-β³-HTrp-OH (3S)-3-Amino-4-(indol-3'-yl)-butyric acid
H-β³-HSer-OH (3R)-3-Amino-4-hydroxy-butyric acid
H-β³-HAsp-OH 3-Amino-pentanedioic acid
H-β³-HGlu-OH (3S)-3-Amino-hexanedioic acid
H-β³-HLys-OH (3S)-3,7-Diamino-heptanoic acid
H-β³-HArg-OH (3S)-3-Amino-6-guanidino-hexanoic-acid
H-β³-HCys-OH (3R)-3-Amino-4-mercapto-butyric acid
H-β³-HAsn-OH (3S)-3-Amino-4-carbamoyl-butyric acid
H-β³-HGln-OH (3S)-3-Amino-5-carbamoyl-pentanoic acid
H-β³-HThr-OH (3R,4R)-3-Amino-4-hydroxy-pentanoic acid
H-β³-HCit-OH (3S)-3-Amino-6-carbamidyl-hexanoic acid
H-β³-HOrn-OH (3S)-3,6-Diamino-hexanoic acid
H-β³-HtBuA-OH (3S)-3-Amino-5,5-dimethyl-hexanoic acid
H-β³-HSar-OH N-Methyl-3-amino-propionic acid
H-β³-HPen-OH (3R)-3-Amino-4-methyl-4-mercapto-pentanoic acid
H-β³-HtBuG-OH (3R)-3-Amino-4,4-dimethyl-pentanoic acid
H-β³-H4AmPhe-OH (3S)-3-Amino-4-(4'-aminophenyl)-butyric acid
H-β³-H3AmPhe-OH (3S)-3-Amino-4-(3'-aminophenyl)-butyric acid
H-β³-H2AmPhe-OH (3S)-3-Amino-4-(2'-aminophenyl)-butyric acid
H-β³-HPhe(mC(NH₂)=NH)—OH (3S)-3-Amino-4-(3'-amidinophenyl)-butyric acid
H-β³-HPhe(pC(NH₂)=NH)—OH (3S)-3-Amino-4-(4'-amidinophenyl)-butyric acid
H-β³-HPhe(mNHC(NH₂)=NH)—OH (3S)-3-Amino-4-(3'-guanidinophenyl)-butyric acid
H-β³-HPhe(pNHC(NH₂)=NH)—OH (3S)-3-Amino-4-(4'-guanidino-phenyl)-butyric acid
H-β³-H2 Pal-OH (3S)-3-Amino-4-(pyridine-2'-yl)-butyric acid
H-β³-H4 Pal-OH (3S)-3-Amino-4-(pyridine-4'-yl)-butyric acid
H-β³-HPhg-OH (3R)-3-Amino-3-phenyl-propionic acid
H-β³-HCha-OH (3S)-3-Amino-4-cyclohexyl-butyric acid
H-β³-HC₄al-OH (3S)-3-Amino-4-cyclobutyl-butyric acid
H-β³-HC₅al-OH (3S)-3-Amino-4-cyclopentyl-butyric acid
H-β³-HNle-OH (3S)-3-Amino-heptanoic acid
H-β³-H2Nal-OH (3S)-3-Amino-4-(2'-naphthyl)-butyric acid
H-β³-H1Nal-OH (3S)-3-Amino-4-(1'-naphthyl)-butyric acid
H-β³-H4ClPhe-OH (3S)-3-Amino-4-(4'-chlorophenyl)-butyric acid
H-β³-H3ClPhe-OH (3S)-3-Amino-4-(3'-chlorophenyl)-butyric acid
H-β³-H2ClPhe-OH (3S)-3-Amino-4-(2'-chlorophenyl)-butyric acid
H-β³-H3, 4Cl₂Phe-OH (3S)-3-Amino-4-(3',4'-dichlorophenyl)-butyric acid
H-β³-H₄FPhe-OH (3S)-3-Amino-4-(4'-fluorophenyl)-butyric acid
H-β³-H₃FPhe-OH (3S)-3-Amino-4-(3'-fluorophenyl)-butyric acid
H-β³-H₂FPhe-OH (3S)-3-Amino-4-(2'-fluorophenyl)-butyric acid
H-β³-HThi-OH (3R)-3-Amino-4-(2'-thienyl)-butyric acid
H-β³-HTza-OH (3R)-3-Amino-4-(2'-thiazolyl)-butyric acid
H-β³-HMso-OH (3R)-3-Amino-4-methylsulfoxyl-butyric acid
H-β³-HAcLys-OH (3S)-7-Acetylamino-3-amino-heptanoic acid
H-β³-HDpr-OH (3R)-3,4-diamino-butyric acid
H-β³-HA₂Bu-OH (3S)-3,5-Diamino-pentanoic acid
H-β³-HDbu-OH (3R)-3,4-Diamino-pentanoic acid
H-β³-HY(Bzl)-OH (3S)-3-Amino-4-(4'-benzyloxyphenyl)-butyric acid
H-β³-HH(Bzl)-OH (3S)-3-Amino-4-(1'-benzylimidazole-4'-yl)-butyric acid
H-β³-HBip-OH (3S)-3-Amino-4-biphenylyl-butyric acid
H-β³-HS(Bzl)-OH (3S)-3-Amino-4-(benzyloxy)-butyric acid
H-β³-HT(Bzl)-OH (3R,4R)-3-Amino-4-benzyloxy-pentanoic acid
H-β³-HalloT-OH (3R,4S)-3-Amino-4-hydroxy-pentanoic acid
H-β³-HLeu3OH—OH (3R,4R)-3-Amino-4-hydroxy-5-methyl-hexanoic acid
H-β³-HhAla-OH (3S)-3-Amino-pentanoic acid
H-β³-HhArg-OH (3S)-3-Amino-7-guanidino-heptanoic acid
H-β³-HhCys-OH (3R)-Amino-5-mercapto-pentanoic acid
H-β³-HhGlu-OH (3S)-3-Amino-heptanedioic acid
H-β³-HhGln-OH (3S)-3-Amino-6-carbamoyl-hexanoic acid
H-β³-HhHis-OH (3S)-3-Amino-5-(imidazole-4'-yl)-pentanoic acid
H-β³-HhIle-OH (3S,5S)-3-Amino-5-methyl-heptanoic acid
H-β³-HhLeu-OH (3S)-3-Amino-6-methyl-heptanoic acid
H-β³-HhNle-OH (3S)-3-Amino-octanoic acid
H-β³-HDiAoc-OH (3S)-3,8-Diamino-octanoic acid
H-β³-HhMet-OH (3S)-3-Amino-6-methylthio-hexanoic acid
H-β³-HhPe-OH (3S)-3-Amino-5-phenyl-pentanoic acid
H-β³-HhSer-OH (3S)-3-Amino-5-hydroxy-pentanoic acid
H-β³-HhThr-OH (3S,5R)-3-Amino-5-hydroxy-hexanoic acid
H-β³-HhTrp-OH (3S)-3-Amino-5-(indol-3'-yl)-pentanoic acid
H-β³-HhThr-OH (3S)-3-Amino-5-(4'-hydroxyphenyl)-pentanoic acid
H-β³-HhCha-OH (3S)-3-Amino-5-cyclohexyl-pentanoic acid
H-β³-HBpa-OH (3S)-3-Amino-4-(4'-benzoylphenyl)-butyric acid
H-β³-HOctG-OH (3S)-3-Amino-undecanoic acid
H-β³-HNle-OH (3S)-3-Amino-heptanoic acid In a particular embodiment of the invention Xaa¹⁵ is ᴰPro, ᴰCha, NMeᴰIle, ᴰTyr, ᴰHis, ᴰHis(Bzl), ᴰ4Pal, NMeᴰTyr, NMeᴰLys, (ABu)G, ᴰIle, NMeᶜAla, ᴰLys, or ᴰDab; and Xaa¹⁶ is ᴸPro or Oic; the aforesaid ᴰPro moiety and/or the aforesaid ᴸPro moiety being optionally substituted as shown in Formula A8' and, respectively, A8", as defined above.

The amino acid residues in Cyclo (-Xaa¹-Xaa²-Xaa³-Cys⁴-Xaa⁵-Xaa⁶-Xaa⁷-Xaa⁸-Arg⁹-Tyr¹⁰-Cys¹¹-Xaa¹²-Xaa¹³-Xaa¹⁴-Xaa¹⁵-Xaa¹⁶-), disulfide bond between Cys⁴ and Cys¹¹, are preferably:

Xaa¹: Tyr or of type M;
Xaa²: His;
Xaa³: Ala;
Xaa⁵: Ser, D-isomer of type F, γ⁴-amino acid residue of type M or β³-amino acid residue of type N;
Xaa⁶: Ala;
Xaa⁷: of formula -A-CO— or D-isomer of type D;
Xaa⁸: Dab;
Xaa¹²: Tyr;
Xaa¹³: Gln;
Xaa¹⁴: Lys;

Xaa$^{15}$: of formula -A-CO—, D-isomer of type C, D, E or F, or N-substituted glycine of type I
Xaa$^{16}$: of formula B—CO—
with the proviso that
Xaa$^1$: is a γ$^4$-amino acid residue of type M; and/or
Xaa$^5$: is the D-isomer of type F, or a γ$^4$-amino of type M or a β$^3$-amino acid residue of type N; and/or;
Xaa$^{15}$: is the D-isomer of type C, D, E or F, or a N-substituted glycine of type I; and/or
Xaa$^{16}$: is of formula —B—CO— with B being the enantiomer of group A105.

The amino acid residues in Cyclo(-Xaa$^1$-Xaa$^2$-Xaa$^3$-Cys$^4$-Xaa$^5$-Xaa$^6$-Xaa$^7$-Xaa$^8$-Arg$^9$-Tyr$^{10}$-Cys$^{11}$-Xaa$^{12}$-Xaa$^{13}$-Xaa$^{14}$-Xaa$^{15}$-Xaa$^{16}$-), disulfide bond between Cys$^4$ and Cys$^{11}$, are most preferably:
Xaa$^1$: Tyr, H-γ$^4$-DiHTyr-OH;
Xaa$^2$: His;
Xaa$^3$: Ala;
Xaa$^5$: Ser, $^D$alloT, Ahb, or H-β$^3$-HSer-OH;
Xaa$^6$: Ala;
Xaa$^7$: $^D$Pro, $^D$Tyr, or $^D$Trp;
Xaa$^8$: Dab;
Xaa$^{12}$: Tyr;
Xaa$^{13}$: Gln;
Xaa$^{14}$: Lys;
Xaa$^{15}$: $^D$Cha, NMe$^D$Ile, $^D$His, $^D$His(Bzl), $^D$4Pal, NMe$^D$-Tyr, NMe$^D$Lys, (ABu)G, $^D$Ile, NMe$^D$Ala, $^D$Tyr, $^D$Lys, $^D$Dab or $^D$Pro;
Xaa$^{16}$: Pro, or Oic;
with the proviso that
Xaa$^1$ is H-γ4-DiHTyr-OH; and/or
Xaa$^5$ is $^D$alloT, Ahb, or H-β$^3$-HSer-OH; and/or
Xaa$^{15}$ is $^D$Cha, NMe$^D$Ile, $^D$His, $^D$His(Bzl), $^D$4 Pal, NMe$^D$-Tyr, NMe$^D$Lys, (ABu)G, $^D$Ile, NMe$^D$Ala, $^D$Tyr, $^D$Lys, or $^D$Dab; and/or
Xaa$^{16}$ is Oic.

If it is desired to exclusively incorporate α-amino acid residues in Cyclo (-Xaa$^1$-Xaa$^2$-Xaa$^3$-Cys$^4$-Xaa$^5$-Xaa$^6$-Xaa$^7$-Xaa$^8$-Arg$^9$-Tyr$^{10}$-Cys$^{11}$-Xaa$^{12}$-Xaa$^{13}$-Xaa$^{14}$-Xaa$^{15}$-Xaa$^{16}$-), disulfide bond between Cys$^4$ and Cys$^{11}$, then the α-amino acid residues are preferably
Xaa$^1$: Tyr;
Xaa$^2$: His;
Xaa$^3$: Ala;
Xaa$^5$: Ser or D-isomer of type F;
Xaa$^6$: Ala;
Xaa$^7$: of formula -A-CO— or D-isomer of type D;
Xaa$^8$: Dab;
Xaa$^{12}$: Tyr;
Xaa$^{13}$: Gln;
Xaa$^{14}$: Lys;
Xaa$^{15}$: of formula -A-CO—, D-isomer of type C, D, E, F, or N-substituted glycine of type I;
Xaa$^{16}$: of formula —B—CO—;
with the proviso that
Xaa$^5$ is the D-isomer of type D; and/or
Xaa$^{15}$ is the D-isomer of type C, D, E, or F; or a N-substituted glycine type I; and/or
Xaa$^{16}$ is of formula —B—CO— with B being the enantiomer of A105.

If it is desired to exclusively incorporate α-amino acid residues in Cyclo(-Xaa$^1$-Xaa$^2$-Xaa$^3$-Cys$^4$-Xaa$^5$-Xaa$^6$-Xaa$^7$-Xaa$^8$-Arg$^9$-Tyr$^{10}$-Cys$^{11}$-Xaa$^{12}$-Xaa$^{13}$-Xaa$^{14}$-Xaa$^{15}$-Xaa$^{16}$-), disulfide bond between Cys$^4$ and Cys$^{11}$, then the α-amino acid residues are most preferably
Xaa$^1$: Tyr;
Xaa$^2$: His;
Xaa$^3$: Ala;
Xaa$^5$: Ser or $^D$alloT;
Xaa$^6$: Ala;
Xaa$^7$: $^D$Pro, $^D$Tyr or $^D$Trp;
Xaa$^8$: Dab;
Xaa$^{12}$: Tyr;
Xaa$^{13}$: Gln;
Xaa$^{14}$: Lys;
Xaa$^{15}$: $^D$Cha, NMe$^D$Ile, $^D$His, $^D$His(Bzl), $^D$4Pal, NMe$^D$-Tyr, NMe$^D$Lys, (ABu)G, $^D$Ile, NMe$^c$Ala, $^D$Tyr, $^D$Lys, $^D$Dab or $^D$Pro
Xaa$^{16}$: Pro or Oic;
with the proviso that
Xaa$^5$ is $^D$alloT; and/or
Xaa$^{15}$ is $^D$Cha, NMe$^D$Ile, $^D$His, $^D$His (Bzl), $^D$4Pal, NMe$^D$-Tyr, NMe$^D$Lys, (ABu)G, $^D$Ile, NMe$^c$Ala, $^D$Tyr, $^D$Lys, or $^D$Dab; and/or
Xaa$^{16}$ is Oic.

Particularly preferred β-peptidomimetics of the invention include those described in Examples 3, 7 and 12.

The processes of the invention can advantageously be carried out as parallel array syntheses to yield libraries of β-hairpin peptidomimetics of the invention. Such parallel syntheses allow one to obtain arrays of numerous (normally 12 to 192, typically 96) compounds as described above in moderate to high yields and defined purities, minimizing the formation of dimeric and polymeric by-products. The proper choice of the functionalized solid-support (i.e. solid support plus linker molecule) and site of cyclization play thereby key roles.

The functionalized solid support is conveniently derived from polystyrene crosslinked with, preferably 1-5%, divinylbenzene; polystyrene coated with polyethyleneglycol spacers (Tentagel®); and polyacrylamide resins (see also D. Obrecht, J.-M. Villalgordo, "Solid-Supported Combinatorial and Parallel Synthesis of Small-Molecular-Weight Compound Libraries", *Tetrahedron Organic Chemistry Series, Vol. 17*, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acid conditions (H. Rink, *Tetrahedron Lett.* 1987, 28, 3783-3790). Linkers of this kind form amides of the carboxyl group of the amino acids; examples of resins functionalized by such linker structures include 4-[(((2,4-dimethoxy-phenyl)Fmoc-aminomethyl)phenoxyacetamido) aminomethyl] PS resin, 4-[(((2,4-dimethoxyphenyl)Fmoc-aminomethyl) phenoxy-acetamido) aminomethyl]-4-methyl-benzydrylamine PS resin (Rink amide MBHA PS Resin), and 4-[(((2,4-dimethoxy-phenyl)Fmoc-aminomethyl) phenoxyacetamido) aminomethyl]benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxy-phenyl)Fmoc-aminomethyl)phenoxyacetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (Sasrin® linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl. Preferably, the support is derived from polystyrene crosslinked with, most preferably 1-5%, divinylbenzene and functionalized by means of the 2-chlorotrityl linker.

When carried out as parallel array syntheses the processes of the invention can be advantageously carried out as described herein below but it will be immediately apparent to those skilled in the art how these procedures will have to be modified in case it is desired to synthesize one single compound of the invention.

A number of reaction vessels (normally 12 to 192, typically 96) equal to the total number of compounds to be synthesized by the parallel method are loaded with 25 to 1000 mg, preferably 60 mg, of the appropriate functionalized solid support, preferably 1 to 3% cross-linked polystyrene or Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (G. B. Fields, C. G. Fields, *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin® linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2,4-dimethoxyphenyl-hydroxymethyl)-phenoxy linker (Rink linker, H. Rink, *Tetrahedron Lett.* 1987, 28, 3787-3790), where the removal of the depsipeptide requires 10% acetic acid in DCM or 0.2% trifluoroacetic acid in DCM; the 4-(4-hydroxymethyl-3-methoxyphenoxy)butyric acid-derived linker (HMPB-linker, Flörsheimer & Riniker, *Peptides* 1991, 1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the peptide detachment using a mixture of glacial acetic acid/trifluoroethanol/DCM (1:2:7) for 30 min.

Suitable protecting groups for α-, β- and γ-amino acids and, respectively, for their residues are, for example, for the amino group (as is present e.g. also in the side-chain of lysine)
Cbz benzyloxycarbonyl
Boc tert.-butyloxycarbonyl
Fmoc 9-fluorenylmethoxycarbonyl
Alloc allyloxycarbonyl
Teoc trimethylsilylethoxycarbonyl
Tcc trichloroethoxycarbonyl
Nps o-nitrophenylsulfonyl;
Trt triphenymethyl or trityl for the carboxyl group (as is present e.g. also in the side-chain of aspartic and glutamic acid) by conversion into esters with the alcohol components
tBu tert.-butyl
Bn benzyl
Me methyl
Ph phenyl
Pac phenacyl
allyl
Tse trimethylsilylethyl
Tce trichloroethyl;

for the guanidino group (as is present e.g. in the side-chain of arginine)
Pmc 2,2,5,7,8-pentamethylchroman-6-sulfonyl
Ts tosyl (i.e. p-toluenesulfonyl)
Cbz benzyloxycarbonyl
Pbf pentamethyldihydrobenzofuran-5-sulfonyl for the hydroxy group (as is present e.g. in the side-chain of threonine and serine)
tBu tert.-butyl
Bn benzyl
Trt trityl
Alloc allyloxycarbonyl and for the mercapto group (as is present e.g. in the side-chain of cysteine)
Acm acetamidomethyl
tBu tert.-butyl
Bn benzyl
Trt trityl
Mtr 4-methoxytrityl.

The 9-fluorenylmethoxycarbonyl-(Fmoc)-protected amino acid derivatives are preferably used as the building blocks for the construction of the β-hairpin loop mimetics of the invention. For the deprotection, i.e. cleaving off of the Fmoc group, 20% piperidine in DMF or 2% DBU/2% piperidine in DMF can be used.

The quantity of the reactant, i.e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The preferred workstations (without, however, being limited thereto) are Labsource's Combi-chem station, Protein Technologies' Symphony and MultiSyn Tech's-Syro synthesizer, the latter additionally equipped with a transfer unit and a reservoir box during the process of detachment of the fully protected linear peptide from the solid support. All synthesizers are able to provide a controlled environment, for example, reactions can be accomplished at temperatures different from room temperature as well as under inert gas atmosphere, if desired.

Amide bond formation requires the activation of the α-carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and, respectively, diisopropylurea is insoluble and, respectively, soluble in the solvents generally used. In a variation of the carbodiimide method 1-hydroxybenzotriazole (HOBt, König & Geiger, *Chem. Ber.* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethyl-amino)-phosphonium hexafluorophosphate (BOP, Castro et al., *Tetrahedron Lett.* 1975, 14, 1219-1222; *Synthesis* 1976, 751-752), or benzotriazol-1-yl-oxytris-pyrrolidino-phosphonium hexafluorophoshate (Py-BOP, Coste et al., *Tetrahedron Lett.* 1990, 31, 205-208), or 2-(1H-benzotriazol-1-yl)1,1,3,3-tetramethyluronium tetrafluoroborate (TBTU), or hexafluorophosphate (HBTU, Knorr et al., *Tetrahedron Lett.* 1989, 30, 1927-1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279-2281) or -(6-Chloro-1H-benzotriazol-1-yl-)-N,N,N',N'-1,1,3,3-tetramethyluronium tetrafluoroborate (TCTU), or hexafluorophosphate (HCTU, Marder, Shivo and Albericio: HCTU and TCTU: New Coupling Reagents: Development and Industrial Applications, Poster Presentation, Gordon Conference February 2002) have also been used as coupling reagents as well as 1,1,3,3-Bis(tetramethylene) chlorouronium hexafluoro-phosphate (PyClU) especially for coupling N-methylated amino acids (J. Coste, E. Frérot, P. Jouin, B. Castro, *Tetrahedron Lett.* 1991, 32, 1967).

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide or depsipeptide indicates qualitatively the presence of the primary amine, can easily and quickly be performed after each coupling step. Fmoc chemistry allows the spectrophotometric detection of the Fmoc chromophore when it is released with the base (Meienhofer et al., Int. *J. Peptide Protein Res.* 1979, 13, 35-42).

The resin-bound intermediate within each reaction vessel is washed free of excess of retained reagents, of solvents, and of by-products by repetitive exposure to pure solvent(s) by one of the two following methods:
1) The reaction vessels are filled with solvent (preferably 5 ml), agitated for 5 to 300 minutes, preferably 15 minutes, and drained to expel the solvent;
2) The reaction vessels are filled with solvent (preferably 5 ml) and drained into a receiving vessel such as a test tube or vial.

Both of the above washing procedures are repeated up to about 50 times (preferably about 10 times), monitoring the efficiency of reagent, solvent, and by-product removal by methods such as TLC, GC, or inspection of the washings.

The above described procedure of reacting the resin-bound compound with reagents within the reaction tubes followed by removal of excess reagents, by-products, and solvents is repeated with each successive transformation until the final resin-bound fully protected linear depsipeptide has been obtained.

Before this fully protected linear peptide is detached from the solid support, the disulfide bridge between $Cys^4$ and $Cys^{11}$ of $Xaa^1$-$Xaa^2$-$Xaa^3$-$Cys^4$-$Xaa^5$-$Xaa^6$-$Xaa^7$-$Xaa^8$-$Arg^9$-$Tyr^{10}$-$Cys^{11}$-$Xaa^{12}$-$Xaa^{13}$-$Xaa^{14}$-$Xaa^{15}$-$Xaa^{16}$ can be formed. For the formation of this disulfide bridge preferably a solution of 10 equivalents of iodine solution is applied in DMF or in a mixture of $CH_2Cl_2$/MeOH for 1.5 h which is repeated for another 3 h with a fresh iodine solution after filtering of the iodine solution, or in a mixture of DMSO and acetic acid solution, buffered with 5% $NaHCO_3$ to pH 5-6 for 4 h, or in water after adjusting to pH 8 with ammonium hydroxide solution by stirring for 24 h, or in a solution of NMP and tri-n-butylphosphine (preferably 50 eq.).

Alternatively, the formation of the disulfide bridge between $Cys^4$ and $Cys^{11}$ of $Xaa^1$-$Xaa^2$-$Xaa^3$-$Cys^4$-$Xaa^5$-$Xaa^6$-$Xaa^7$-$Xaa^8$-$Arg^9$-$Tyr^{10}$-$Cys^{11}$-$Xaa^{12}$-$Xaa^{13}$-$Xaa^{14}$-$Xaa^{15}$-$Xaa^{16}$ can be carried out subsequent to the work-up method 2), as described herein below, by stirring the crude fully deprotected and cyclized peptide for 24 h in water containing DMSO up to 15% by volume, buffered with 5% $NaHCO_3$ to pH 5-6, or buffered with ammonium acetate to pH 7-8, or adjusted with ammonium hydroxide to pH 8. Following evaporation to dryness Cyclo(-$Xaa^1$-$Xaa^2$-$Xaa^3$-$Cys^4$-$Xaa^5$-$Xaa^6$-$Xaa^7$-$Xaa^8$-$Arg^9$-$Tyr^{10}$)-$Cys^{11}$-$Xaa^{12}$-$Xaa^{13}$-$Xaa^{14}$-$Xaa^{15}$-$Xaa^{16}$-), disulfide bond between $Cys^4$ and $Cys^{11}$ is obtained as end-product.

Detachment of the fully protected linear peptide from the solid support is achieved by exposing the loaded resin with a solution of the cleavage reagent (preferably 3 to 5 ml). Temperature control, agitation, and reaction monitoring are implemented as described above. Via a transfer-unit the reaction vessels are connected with a reservoir box containing reservoir tubes to efficiently collect the cleaved product solutions. The resins remaining in the reaction vessels are then washed 2 to 5 times as above with 3 to 5 ml of an appropriate solvent to extract (wash out) as much of the detached products as possible. The product solutions thus obtained are combined, taking care to avoid cross-mixing. The individual solutions/extracts are then manipulated as needed to isolate the final compounds.

Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as DCM, DMF, dioxane, THF and the like. Various coupling reagents which were mentioned earlier can be used for the cyclization. The duration of the cyclization is about 6-48 hours, preferably about 16 hours. The progress of the reaction is followed, e.g. by RP-HPLC (Reverse Phase High Performance Liquid Chromatography). Then the solvent is removed by evaporation, the fully protected cyclic depsipeptide derivative is dissolved in a solvent which is not miscible with water, such as DCM, and the solution is extracted with water or a mixture of water-miscible solvents, in order to remove any excess of the coupling reagent.

Finally, the fully protected peptide derivative is treated with 95% TFA, 2.5% $H_2O$, 2.5% TIS or another combination of scavengers for effecting the cleavage of protecting groups. The cleavage reaction time is commonly 30 minutes to 12 hours, preferably about 2.5 hours.

Alternatively, the detachment and complete deprotection of the fully protected peptide from the solid support can be achieved manually in glass vessels.

After full deprotection one of the following methods can be used for further work-up:
1) The volatiles are evaporated to dryness and the crude peptide is dissolved in 20% AcOH in water and extracted with isopropyl ether or other solvents which are suitable therefor. The aqueous layer is collected and evaporated to dryness, and the fully deprotected peptide, Cyclo(-$Xaa^1$-$Xaa^2$-$Xaa^3$-$Cys^4$-$Xaa^5$-$Xaa^6$-$Xaa^7$-$Xaa^8$-$Arg^9$-$Tyr^{10}$-$Cys^{11}$-$Xaa^{12}$-$Xaa^{13}$-$Xaa^{14}$-$Xaa^{15}$-$Xaa^{16}$-), disulfide bond between $Cys^4$ and $Cys^{11}$, is obtained as end-product;
2) The deprotection mixture is concentrated under vacuum. Following precipitation of the fully deprotected peptide in diethylether at preferably 0° C. the solid is washed up to about 10 times, preferably 3 times, dried, and the fully deprotected peptide, Cyclo(-Xaa$^1$-Xaa$^2$-Xaa$^3$-Cys$^4$-Xaa$^5$-Xaa$^6$-Xaa$^7$-Xaa$^8$-Arg$^9$-Tyr$^{10}$-Cys$^{11}$-Xaa$^{12}$-Xaa$^{13}$-Xaa$^{14}$-Xaa$^{15}$-Xaa$^{16}$-), disulfide bond between Cys$^4$ and Cys$^{11}$, is obtained as end-product, if disulfide bond has been formed on solid support as described herein above.

As mentioned earlier, it is thereafter possible, if desired, to convert the fully deprotected product of Cyclo(-Xaa$^1$-Xaa$^2$-Xaa$^3$-Cys$^4$-Xaa$^5$-Xaa$^6$-Xaa$^7$-Xaa$^8$-Arg$^9$-Tyr$^{10}$-Cys$^{11}$-Xaa$^{12}$-Xaa$^{13}$-Xaa$^{14}$-Xaa$^{15}$-Xaa$^{16}$-), disulfide bond between Cys$^4$ and Cys$^{11}$, thus obtained into a pharmaceutically acceptable salt or to convert a pharmaceutically acceptable, or unacceptable, salt thus obtained into the corresponding free compound of Cyclo(-Xaa$^1$-Xaa$^2$-Xaa$^3$-Cys$^4$-Xaa$^5$-Xaa$^6$-Xaa$^7$-Xaa$^8$-Arg$^9$-Tyr$^{10}$-Cys$^{11}$-Xaa$^{12}$-Xaa$^{13}$-Xaa$^{14}$-Xaa$^{15}$-Xaa$^{16}$-), disulfide bond between Cys$^4$ and Cys$^{11}$, or into a different, pharmaceutically acceptable, salt. Any of these operations can be carried out by methods well known in the art.

The β-hairpin peptidomimetics of the invention can be used in a wide range of applications in order to prevent HIV infections in healthy individuals and slow or halt viral progression in infected patients, or where cancer is mediated or resulting from the CXCR4 receptor activity, or where immunological diseases are mediated or resulting from CXCR4 receptor activity; or these β-hairpin peptidomimetics can be used to treat immunosuppression, or they can be used during apheresis collections of peripheral blood stem cells and/or as agents to induce mobilization of stem cells to regulate tissue repair.

The β-hairpin peptidomimetics of the invention may be administered per se or may be applied as an appropriate formulation together with carriers, diluents or excipients well known in the art.

When used to treat or prevent HIV infections or cancer such as breast cancer, brain cancer, prostate cancer, heptatocellular carcinoma, colorectal cancer, lung cancer, kidney cancer, neuroblastoma, ovarian cancer, endometrial cancer, germ cell tumor, eye cancer, multiple myeloma, pancreatic cancer, gastric cancer, rhabdomyo-sarcoma, melanoma, chronic lyphomphocytic leukemia, acute myelogenous leukemia, acute lymphoblastic leukemia, multiple myeloma, Non-Hodgkin's lymphoma; metastasis, angiogenesis, and haematopoetic tissues; or inflammatory disorders such as asthma, allergic rhinitis, hypersensitivity lung diseases, hypersensitivity pneumonitis, eosinophilic pneumonias, delayed-type hypersensitivity, interstitial lung diseas (ILD), idiopathic pulmonary fibrosis, ILD associated with rheumatoid arthritis, systemic lupus erythematosus, ankylosing sponylitis, systemic sclerosis, Sjogren's syndrome, systemic anaphylaxis or hypersensitivity responses, drug allergies, rheumatoid arthritis, psoriatic arthritis, systemic lupus erythematosus, myasthenia gravis, juvenile onset diabetes, glomerulonephritis, autoimmune throiditis, graft rejection, including allograft rejection or graft-versus-host disease, inflammatory bowel diseases, inflammatory dermatoses; or to treat glaucoma; or to treat focal ischemic stroke, global cerebral ischemia, myocardial infarction, hind limb ischemia and peripheral ischemia; or to treat injury of the liver, kidney and lung or to treat immunosuppression, including immunosuppression induced by chemotherapy, radiation therapy or graft/transplantation rejection, the β-hairpin peptidomimetics of the invention can be administered singly, as mixtures of several β-hairpin peptidomimetics, in combination with other anti-HIV agents, or antimicrobial agents or anti cancer agents or anti-inflammatory agents, or in combination with other pharmaceutically active agents. The β-hairpin peptidomimetics of the invention can be administered per se or as pharmaceutical compositions.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxilliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solutions may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion by a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the β-hairpin peptidomimetics of the invention are conveniently delivered in form of an aeorosol spray from pressurized packs or a nebulizer, with the use of a suitable propellant, e.g. dichlorodifluoromethane, trichlorofluoromethane, carbon dioxide or another suitable gas. In the case of a pressurized aerosol the dose unit may be determined by providing a valve to deliver a metered amount.

Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as suppositories together with appropriate suppository bases such as cocoa butter or other glycerides.

In addition to the formulations described above, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide may also be employed. Additionally, the β-hairpin peptidomimetics of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the β-hairpin pepdidomimetics of the invention may contain charged residues, they may be included in any of the above-described formulations as such or as pharmaceutically acceptable salts. Pharmaceutically acceptable salts tend to be more soluble in aqueous and other protic solvents than are the corresponding free forms.

The β-hairpin peptidomimetics of the invention, or compositions thereof, will generally be used in an amount effective to achieve the intended purpose. It is to be understood that the amount used will depend on a particular application.

For topical administration to treat or prevent HIV infections a therapeutically effective dose can be determined using, for example, the in vitro assays provided in the examples. The treatment may be applied while the HIV infection is visible, or even when it is not visible. An ordinary skilled expert will be able to determine therapeutically effective amounts to treat topical HIV infections without undue experimentation.

For systemic administration, a therapeutically effective dose can be estimated initially from in vitro assays. For example, a dose can be formulated in animal models to achieve a circulating β-hairpin peptidomimetic concentration range that includes the $IC_{50}$ as determined in the cell culture (i.e. the concentration of a test compound that is lethal to 50% of a cell culture). Such information can be used to more accurately determine useful doses in humans.

Initial dosages can also be determined from in vivo data, e.g. animal models, using techniques that are well known in the art. One having ordinary skill in the art could readily optimize administration to humans based on animal data.

Dosage amounts for applications as anti-HIV agents may be adjusted individually to provide plasma levels of the β-hairpin peptidomimetics of the invention which are sufficient to maintain the therapeutic effect. Therapeutically effective serum levels may be achieved by administering multiple doses each day.

In cases of local administration or selective uptake, the effective local concentration of the β-hairpin peptidomimetics of the invention may not be related to plasma concentration. One having the ordinary skill in the art will be able to optimize therapeutically effective local dosages without undue experimentation.

The amount of β-hairpin peptidomimetics administered will, of course, be dependent on the subject being treated, on the subject's weight, the severity of the affliction, the manner of administration and the judgement of the prescribing physician.

The anti-HIV therapy may be repeated intermittently while infections are detectable or even when they are not detectable. The therapy may be provided alone or in combination with other drugs, such as for example other anti-HIV agents or anti cancer agents, or other antimicrobial agents.

Normally, a therapeutically effective dose of the β-hairpin peptidomimetics described herein will provide therapeutic benefit without causing substantial toxicity.

Toxicity of the β-hairpin peptidomimetics of the invention can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, In: *The Pharmacological Basis of Therapeutics*, Ch.1, p. 1).

The following Examples illustrate the present invention but are not to be construed as limiting its scope in any way.

EXAMPLES

1. Peptide Synthesis

Coupling of the First Protected Amino Acid Residue to the Resin 1 g (1.4 mMol) of 2-chlorotritylchloride resin (1.4 mMol/g; Barlos et al. *Tetrahedron Lett.* 1989, 30, 3943-3946) was filled into a dried flask. The resin was suspended in $CH_2Cl_2$ (5 ml) and allowed to swell at room temperature under constant shaking for 30 min. A solution of 0.98 mMol (0.7 eq) of the first suitably protected amino acid residue (see below) in $CH_2Cl_2$ (5 ml) completed by 960 µl (4 eq) of diisopropylethylamine (DIEA) was added. After shaking the reaction mixture for 4 hours at 25° C. the resin was filtered off and washed successively with $CH_2Cl_2$ (1×), DMF (1×) and $CH_2Cl_2$ (1×). A solution of $CH_2Cl_2$/MeOH/DIEA (17/2/1, 10 ml) was added to the resin and the suspension was shaken for 30 min. After filtration the resin was washed in the following order with $CH_2Cl_2$ (1×), DMF (1×), $CH_2Cl_2$ (1×), MeOH (1×), $CH_2Cl_2$ (1×), MeOH (1×), $CH_2Cl_2$ (2×), $Et_2O$ (2×) and dried under vacuum for 6 hours.

Loading was typically 0.6-0.7 mMol/g.

The following preloaded resins were prepared:

Fmoc-ProO-chlorotrityl resin, Fmoc-OicO-chlorotrityl resin, and

Fmoc-AlaO-chlorotrityl resin.

The synthesis was carried out employing a Syro-peptide synthesizer (MultiSynTech) using 24-96 reaction vessels. In each vessel 0.04 mMol of the above resin were placed and the resin was swollen in $CH_2Cl_2$ and DMF for 15 min, respectively. The following reaction cycles were programmed and carried out:

| Step | Reagent | Time |
|---|---|---|
| 1 | DMF, wash | 2 × 1 min |
| 2 | 20% piperidine/DMF | 1 × 5 min, 1 × 15 min |
| 3 | DMF, wash | 5 × 1 min |
| 4a | 5 eq Fmoc amino acid/DMF + 5 eq HCTU/DMF, 10 eq DIEA/DMF | 1 × 60 min |
| 5 | DMF, wash | 3 × 1 min |

Step 4a was repeated once.

Unless indicated otherwise, the final coupling of an amino acid was followed by a Fmoc deprotection by applying steps 1-3 of the above described reaction cycle.

To introduce a N-substituted glycine building block into position Xaa[15] the following steps 4b.1-4-b.3 were used instead of step 4a:

| | | |
|---|---|---|
| 4b.1 | 11 eq $BrCH_2COOH$/DMF + 13 eq DIC | 1 × 90 min |
| 4b.2 | DMF, wash | 4 × 2 min |
| 4b.3 | 20 eq amine building block with protective residue/DMF | 1 × 120 min |

Moreover, if a N-substituted glycine building block had been introduced in the previous cycle, step 4a was modified as follows:

| | | |
|---|---|---|
| 4c | 5 eq Fmoc amino acid/DMF + 3.5 eq HATU/DMF, 7 eq DIEA/DMF | 1 × 120 min |

To introduce a N-Methyl-substituted amino acid building block into position Xaa[15] the following steps 4d.1-4d.10 were used instead of step 4a:

| | | |
|---|---|---|
| 4d.1 | 5 eq oNBS-Cl, 10 eq Collidine/NMP | 2 × 15 min |
| 4d.2 | NMP, wash | 2 × 1 min |
| 4d.3 | DMF, wash | 2 × 1 min |
| 4d.4 | THF, wash | 2 × 1 min |
| 4d.5 | 5 eq $Ph_3P$, MeOH/THF 1:1 [v/v], 5 eq DIAD | 2 × 20 min |
| 4d.6 | THF, wash | 3 × 1 min |
| 4d.7 | NMP, wash | 2 × 1 min |
| 4d.8 | 10 eq Mercaptoethanol, 5 eq DBU/NMP | 3 × 10 min |
| 4d.9 | NMP, wash | 3 × 1 min |
| 4d.10 | DMF, wash | 2 × 1 min |

Furthermore, if a N-Methyl-substituted amino acid building block had been introduced in the previous cycle, steps 1-3 were skipped and step 4a was modified as follows:

| | | |
|---|---|---|
| 4e | 3 eq Fmoc amino acid/DMF + 3 eq PyClU/DMF, 5 eq DIEA/DMF | 2 × 60 min |

Cyclization and Work Up of Backbone Cyclized Peptides
Cleavage of the Fully Protected Peptide Fragment After completion of the synthesis, the resin (0.04 mMol) was suspended in 1 ml (0.13 mMol, 3.4 eq) of 1% TFA in $CH_2Cl_2$ (v/v) for 3 minutes, filtered, and the filtrate was neutralized with 1 ml (0.58 mMol, 14.6 eq) of 10% DIEA in $CH_2Cl_2$ (v/v). This procedure was repeated three times to ensure completion of the cleavage. The filtrate was evaporated to dryness and a sample of the product was fully deprotected by using a cleavage mixture containing 95% trifluoroacetic acid (TFA), 2.5% water and 2.5% triisopropylsilane (TIS) to be analyzed by reverse phase-HPLC (column $C_{18}$) and ESI-MS to monitor the efficiency of the linear peptide synthesis.

Cyclization of the Linear Peptide

The fully protected linear peptide (0.04 mMol) was dissolved in DMF (4 μMol/ml). Then 30.4 mg (0.08 mMol, 2 eq) of HATU, 10.9 mg (0.08 mMol, 2 eq) of HOAt and 28 μl (0.16 mMol, 4 eq) DIEA were added, and the mixture was vortexed at 25° C. for 16 hours and subsequently concentrated under high vacuum. The residue was partitioned between $CH_2Cl_2$ and $H_2O/CH_3CN$ (90/10: v/v). The $CH_2Cl_2$ phase was evaporated to yield the fully protected cyclic peptide.

Full Deprotection of the Cyclic Peptide

The cyclic peptide obtained was dissolved in 3 ml of the cleavage mixture containing 82.5% trifluoroacetic acid (TFA), 5% water, 5% thioanisole, 5% phenol and 2.5% ethandithiole (EDT). The mixture was allowed to stand at 25° C. for 2.5 hours and thereafter concentrated under vacuum. After precipitation of the cyclic fully deprotected depsipeptide in diethylether ($Et_2O$) at 0° C. the solid was washed twice with $Et_2O$ and dried.

Formation of Disulfide β-Strand Linkage and Purification

After full deprotection, the crude peptide was dissolved in 0.1 M ammonium acetate buffer (1 mg/1 ml, pH=7-8). DMSO (up to 5% by volume) was added and the solution was shaken overnight. Following evaporation the residue was purified by preparative reverse phase HPLC.

Analytical Method:

Analytical HPLC retention times (RT, in minutes) were determined using an Xbridge C18 2.5 μm column with the following solvents A ($H_2O$+0.1% TFA) and B ($CH_3CN$+ 0.09% TFA) and the gradient: 0 min: 97% A, 3% B; 3 min: 3% A, 97% B; 3.01-3.6 min: 3% A, 97% B; 3.7 min: 97% A, 3% B; 3.71-4.3 min: 97% A, 3% B.

Examples 1-4, 6-15, 17-18 and 20 are shown in Table 1. The peptides were synthesized starting with the amino acid Pro (Xaa[16]) which was grafted to the resin. Starting resin was Fmoc-ProO-chlorotrityl resin, which was prepared as described above. The linear peptides were synthesized on solid support according to the procedure described above in the following sequence: Resin-Pro[16]-Xaa[15]-Xaa[14]-Xaa[13]-Xaa[12]-Cys[11]-Tyr[10]-Arg[9]-Xaa[8]-Xaa[7]-Xaa[6]-Xaa[5]-Cys[4]-Xaa[3]-Xaa[2]-Xaa[1].

Following a final Fmoc deprotection as described above, the peptides were cleaved from the resin, cyclized, deprotected and after formation of the disulfide β-strand linkage purified as indicated above.

HPLC-retention times (minutes) were determined using the gradient method as described above.

Example 5 is shown in Table 1, too. The peptide was synthesized starting with the amino acid Dab (Xaa[8]) which was grafted to the resin. Starting resin was Fmoc-Dab(Boc) O-chlorotrityl resin, which was prepared as described above. The linear peptide was synthesized on solid support according to the procedure described above in the following sequence: Resin-Dab[8]-Xaa[7]-Xaa[6]-Xaa[5]-Cys[4]-Xaa[3]-Xaa[2]-Xaa[1]-Xaa[16]-Xaa[15]-Xaa[14]-Xaa[13]-Xaa[12]-Cys[11]-Tyr[10]-Arg[9].

Following a final Fmoc deprotection as described above, the peptide was cleaved from the resin, cyclized, deprotected and after formation of the disulfide β-strand linkage purified as indicated above.

HPLC-retention time (minutes) was determined using the gradient method as described above Example 16 is likewise shown in Table 1. The peptide was synthesized starting with the amino acid Oic (Xaa$^{16}$) which was grafted to the resin. Starting resin was Fmoc-OicO-chlorotrityl resin, which was prepared as described above. The linear peptide was synthesized on solid support according to the procedure described above in the following sequence: Resin-Oic$^{16}$-Xaa$^{15}$-Xaa$^{14}$-Xaa$^{13}$-Xaa$^{12}$-Cys$^{11}$-Tyr$^{10}$-Arg$^{9}$-Xaa$^{8}$-Xaa$^{7}$-Xaa$^{6}$-Xaa$^{5}$-Cys$^{4}$-Xaa$^{3}$-Xaa$^{2}$-Xaa$^{1}$. Following a final Fmoc deprotection as described above, the peptide was cleaved from the resin, cyclized, deprotected and after formation of the disulfide β-strand linkage purified as indicated above.

HPLC-retention time (minutes) was determined using the gradient method as described above Example 19 is shown in Table 1 as well. The peptide was synthesized starting with the amino acid Ala (Xaa$^{3}$) which was grafted to the resin. Starting resin was Fmoc-AlaO-chlorotrityl resin, which was prepared as described above. The linear peptide was synthesized on solid support according to the procedure described above in the following sequence: Resin-Ala$^{3}$-Xaa$^{2}$-Xaa$^{1}$-Xaa$^{16}$-Xaa$^{15}$-Xaa$^{14}$-Xaa$^{13}$-Xaa$^{12}$-Cys$^{11}$-Tyr$^{10}$-Arg$^{9}$-Xaa$^{8}$-Xaa$^{7}$-Xaa$^{6}$-Xaa$^{5}$-Cys$^{4}$. Following a final Fmoc deprotection as described above, the peptide was cleaved from the resin, cyclized, deprotected and after formation of the disulfide β-strand linkage purified as indicated above.

HPLC-retention times (minutes) was determined using the gradient method as described above.

TABLE 1

Examples (Ex.)

| Ex. Seq ID | Xaa$^1$ | Xaa$^2$ | Xaa$^3$ | Cys$^4$ | Xaa$^5$ | Xaa$^6$ | Xaa$^7$ | Xaa$^8$ | Arg$^9$ | Tyr$^{10}$ | Cys$^{11}$ | Xaa$^{12}$ | Xaa$^{13}$ | Xaa$^{14}$ | Xaa$^{15}$ | Xaa$^{16}$ |
|---|---|---|---|---|---|---|---|---|---|---|---|---|---|---|---|---|
| 1. SEQ ID NO: 1 | Tyr | His | Ala | Cys | Ser | Ala | $^D$Pro | Dab | Arg | Tyr | Cys | Tyr | Gln | Lys | $^D$Cha | Pro |
| 2. SEQ ID NO: 2 | Tyr | His | Ala | Cys | Ser | Ala | $^D$Pro | Dab | Arg | Tyr | Cys | Tyr | Gln | Lys | NMe$^D$Ile | Pro |
| 3. SEQ ID No: 3 | Tyr | His | Ala | Cys | Ser | Ala | $^D$Pro | Dab | Arg | Tyr | Cys | Tyr | Gln | Lys | $^D$Tyr | Pro |
| 4. SEQ ID NO: 4 | Tyr | His | Ala | Cys | Ser | Ala | $^D$Pro | Dab | Arg | Tyr | Cys | Tyr | Gln | Lys | $^D$His | Pro |
| 5. SEQ ID NO: 5 | Tyr | His | Ala | Cys | Ser | Ala | $^D$Pro | Dab | Arg | Tyr | Cys | Tyr | Gln | Lys | $^D$His(Bzl) | Pro |
| 6. SEQ ID NO: 6 | Tyr | His | Ala | Cys | Ser | Ala | $^D$Pro | Dab | Arg | Tyr | Cys | Tyr | Gln | Lys | $^D$4Pal | Pro |
| 7. SEQ ID NO: 7 | Tyr | His | Ala | Cys | Ser | Ala | $^D$Pro | Dab | Arg | Tyr | Cys | Tyr | Gln | Lys | NMe$^D$Tyr | Pro |
| 8. SEQ ID NO: 8 | Tyr | His | Ala | Cys | Ser | Ala | $^D$Pro | Dab | Arg | Tyr | Cys | Tyr | Gln | Lys | NMe$^D$Lys | Pro |
| 9. SEQ ID NO: 9 | Tyr | His | Ala | Cys | Ser | Ala | $^D$Pro | Dab | Arg | Tyr | Cys | Tyr | Gln | Lys | (ABu)G | Pro |
| 10. SEQ ID NO: 10 | Tyr | His | Ala | Cys | Ser | Ala | $^D$Tyr | Dab | Arg | Tyr | Cys | Tyr | Gln | Lys | $^D$Ile | Pro |
| 11. SEQ ID NO: 11 | Tyr | His | Ala | Cys | Ser | Ala | $^D$Trp | Dab | Arg | Tyr | Cys | Tyr | Gln | Lys | $^D$Ile | Pro |
| 12. SEQ ID NO: 12 | Tyr | His | Ala | Cys | Ser | Ala | $^D$Tyr | Dab | Arg | Tyr | Cys | Tyr | Gln | Lys | NMe$^D$Ala | Pro |
| 13. SEQ ID NO: 13 | Tyr | His | Ala | Cys | Ser | Ala | $^D$Tyr | Dab | Arg | Tyr | Cys | Tyr | Gln | Lys | $^D$Tyr | Pro |
| 14. SEQ ID NO: 14 | Tyr | His | Ala | Cys | Ser | Ala | $^D$Tyr | Dab | Arg | Tyr | Cys | Tyr | Gln | Lys | $^D$Lys | Pro |
| 15. SEQ ID NO: 15 | Tyr | His | Ala | Cys | Ser | Ala | $^D$Tyr | Dab | Arg | Tyr | Cys | Tyr | Gln | Lys | $^D$Dab | Pro |
| 16. SEQ ID NO: 16 | Tyr | His | Ala | Cys | Ser | Ala | $^D$Pro | Dab | Arg | Tyr | Cys | Tyr | Gln | Lys | $^D$Pro | Oic |
| 17. SEQ ID NO: 17 | Tyr | His | Ala | Cys | $^D$alloT | Ala | $^D$Pro | Dab | Arg | Tyr | Cys | Tyr | Gln | Lys | $^D$Pro | Pro |
| 18. SEQ ID NO: 18 | γ$^4$Y$^{b)}$ | His | Ala | Cys | Ser | Ala | $^D$Pro | Dab | Arg | Tyr | Cys | Tyr | Gln | Lys | $^D$Pro | Pro |
| 19. SEQ ID NO: 19 | Tyr | His | Ala | Cys | Ahb | Ala | $^D$Pro | Dab | Arg | Tyr | Cys | Tyr | Gln | Lys | $^D$Pro | Pro |
| 20. SEQ ID NO: 20 | Tyr | His | Ala | Cys | β$^3$S$^{c)}$ | Ala | $^D$Pro | Dab | Arg | Tyr | Cys | Tyr | Gln | Lys | $^D$Pro | Pro |

Cys in pos.4 and 11 in Ex. 1-20 form a disulfide bridge,
$^{b)}$γ$^4$Y: H-γ$^4$-DiFlTyr-OH
$^{c)}$β$^3$S: H-β$^3$-HSer-OH

TABLE 2

| Ex. | Purity [%][a] | (M + 2H)/2 | RT |
|---|---|---|---|
| 1 | 95 | 960.8 | 1.86 |
| 2 | 95 | 947.8 | 1.72 |
| 3 | 95 | 965.7 | 1.59 |
| 4 | 95 | 952.7 | 1.55 |
| 5 | 95 | 997.7 | 1.64 |
| 6 | 95 | 958.3 | 1.55 |
| 7 | 95 | 972.8 | 1.64 |
| 8 | 88 | 955.2 | 1.52 |
| 9 | 95 | 948.3 | 1.53 |
| 10 | 95 | 973.8 | 1.72 |
| 11 | 95 | 985.3 | 1.76 |
| 12 | 95 | 959.8 | 1.60 |
| 13 | 95 | 998.8 | 1.66 |
| 14 | 95 | 981.2 | 1.57 |
| 15 | 91 | 967.5 | 1.56 |
| 16 | 95 | 960.0 | 1.72 |
| 17 | 95 | 939.4 | 1.61 |
| 18 | 95 | 946.7 | 1.61 |
| 19 | 95 | 939.5 | 1.62 |
| 20 | 95 | 939.4 | 1.58 |

[a]%-purity of compounds after prep. HPLC.

2. Biological Methods 2.1. Preparation of the Peptides

Lyophilized peptides were weighed on a Microbalance (Mettler MT5) and dissolved in sterile water to a final concentration of 1 mM or dissolved in DMSO to a final concentration of 10 mM. Stock solutions were kept at +4° C., light protected. In case of DMSO stock solutions the biological assays were carried out under assay conditions having less than 1% DMSO.

2.2. Cell Culture

Mouse pre-B cells were cultured in RPMI1640 plus 5% FBS, antibiotic/antimycotic, non essential amino acid, 50 µM β-mercaptoethanol and 1 mM natrium pyruvate. HELA cells were maintained in RPMI1640 plus 10% FBS, pen/strept and 2 mM L-glutamine. Cos-7 cells were grown in DMEM medium with 4500 mg/mL glucose supplemented with 10% FCS, pen/strept and 2 mM L-glutamine. All cell lines were grown at 37° C. at 5% $CO_2$. Cell media, media supplements, PBS-buffer, HEPES, antibiotic/antimycotic, pen/strept, non essential amino acid, L-glutamine, β-mercaptoethanol and sera were purchased from Gibco (Pailsey, UK). All fine chemicals were supplied by Merck (Darmstadt, Germany).

2.3. $Ca^{2+}$-Assay: CXCR4-Antagonizing Activity of the Peptides

Increases in intracellular calcium were monitored using a Flexstation 384 (Molecular Devices, Sunnyvale, Calif.) to assay the depsipeptides for CXCR4 antagonism in a mouse pre-B cell line 300-19 stably transfected with human CXCR4 (E. Oberlin, A. Amara, F. Bachelerie, C. Bessia, J.-L. Virelizier, F. Arenzana-Seisdedos, O. Schwartz, J.-M. Heard, I. Clark-Lewis, D. F. Legler, M. Loetscher, M. Baggiolini, B. Moser, Nature 1996, 382, 833-835; M. Loetscher, T. Geiser, T. O'Reilly, R. Zwalen, M. Baggiolini, B. Moser, J. Biol. Chem. 1994, 269, 232-237; M. D'Apuuo, A. Rolink, M. Loetscher, J. A. Hoxie, I. Clark-Lewis, F. Melchors, M. Baggiolini, B. Moser, Eur. J. Immunol. 1997, 27, 1788-1793). The cells were batch loaded with the Calcium 4 Assay kit (Molecular Devices) in assay buffer (Hanks Balanced salt solution [HBSS], 20 mM HEPES, pH 7.4, 0.1% BSA) for 1 h at room temperature and labeled cells were dispensed into black 96 well assays plates (Costar No. 3603). Calcium mobilization induced by stromal-derived factor-1 (SDF-1) was measured in the Flexstation 384 (excitation: 485 nm; emission: 525 nm) for 90 seconds. Antagonist activity of peptides was determined by spiking the cells with compounds prior to SDF-1 addition. Dose response curves (compound concentration versus % maximum response for SDF-1) were determined for each antagonist and $IC_{50}$ values were calculated by fitting the data to a four parameter logistic equation using SoftmaxPro 4.8 (Molecular Devices).

2.4. Cytotoxicity Assay

The cytotoxicity of the depsipeptides to HELA cells (Acc57) and COS-7 cells (CRL-1651) was determined using the MTT reduction assay (T. Mossman, J. Immunol. Meth. 1983, 65, 55-63; M. V. Berridge, A. S. Tan, Arch. Biochem. Biophys. 1993, 303, 474-482). Briefly, the method was as follows: 7000 HELA cells/well and 4500 COS-7 cells/well were seeded and grown in 96-well microtiter plates for 24 h at 37° C. at 5% $CO_2$. Thereafter, time zero (Tz) was determined by MTT reduction (see below). The supernatant of the remaining wells was discarded, and fresh medium and compounds in serial dilutions (12.5, 25 and 50 µM, triplicates) were pipetted into the wells. After incubation of the cells for 48 h at 37° C. at 5% $CO_2$ the supernatant was discarded again and 100 µL MTT reagent (0.5 mg/mL in RPMI1640 and DMEM, respectively)/well was added. Following incubation at 37° C. for 2 h the media were aspirated and the cells were spiked (100 µL isopropanol/well). The absorbance of the solubilized formazan was measured at 595 nm ($OD_{595}$peptide). For each concentration averages were calculated from triplicates. The percentage of growth was calculated as follows: ($OD_{595}$peptide-$OD_{595}$Tz-$OD_{595}$Empty well)/($OD_{595}$Tz-$OD_{595}$Empty well)×100%. The $GI_{50}$ (Growth Inhibition) concentrations were calculated for each depsipeptide by using a trend line function for the concentrations (50, 25, 12.5 and 0 µM), the corresponding percentages and the value 50, (=TREND ($C_{50}$:$C_0$, %$_{50}$:%$_0$, 50).

2.5. Hemolysis

The peptides were tested for their hemolytic activity against human red blood cells (hRBC). Fresh hRBC were washed three times with phosphate buffered saline (PBS) and centrifuged for 10 min at 2000×g. Compounds (100 µM) were incubated with 20% hRBC (v/v) for 1 h at 37° C. The final erythrocyte concentration was approximately $0.9 \times 10^9$ cells/mL. A value of 0% and 100% cell lyses, respectively, was determined by incubation of hRBC in the presence of PBS alone and 0.1% Triton X-100 in $H_2O$, respectively. The samples were centrifuged, the supernatants were 20-fold diluted in PBS buffer and the optical densities (OD) were measured at 540 nm. The 100% lyses value ($OD_{540}H_2O$) gave an $OD_{540}$ of approximately 1.3-1.8.

Percent hemolysis was calculated as follows: ($OD_{540}$peptide/$OD_{540}H_2O$)×100%.

2.6. Plasma Stability

The stability of the peptides in human and mouse plasma was determined by applying the following method: 315 µL/deep well of freshly thawed human plasma (Basler Blutspende-dienst) and mouse plasma (Harlan Sera-Lab, UK), respectively, were spiked with 35 µL/well of compound in PBS (100 µM, triplicate) and incubated at 37° C. At t=0, 15, 30, 60, 120 and 240 min aliquots of 50 µL were transferred to filtration plate wells containing 150 µL/well of acetonitrile. Following shaking for 2 min the occurred suspensions were filtrated by vacuum and finally, 100 µL of each filtrate were transferred to a propylene microtiter plate, and analyzed by LC/MS as follows: Column: Waters, XBridge C18, mobile phases: (A) water+0.1% formic acid and (B) acetonitrile/water, 95/5 (v/v)+0.1% formic acid, gradient: 5%-100% (B) in 2 minutes, electrospray ionization, MRM detection (triple quadrupole). The peak areas were determined and triplicate values are averaged. The stability is expressed in percent of the initial value at t=0. ($t_x/t_o \times 100$). By using the TREND function of EXCEL (Microsoft Office 2003) $T_{1/2}$ were determined.

TABLE 3

| Ex. | IC50% [nM] ± SD, CXCR4 receptor |
|---|---|
| 1 | 1.30 ± 0.4 |
| 2 | 1.22 ± 1.0 |
| 3 | 1.94 ± 0.5 |
| 4 | 0.52 ± 0.3 |
| 5 | 0.92 ± 0.2 |
| 6 | 0.17 ± 0.1 |
| 7 | 0.33 ± 0.1 |
| 8 | 0.31 ± 0.2 |
| 9 | 0.09 ± 0.05 |
| 10 | 1.18 ± 0.4 |
| 11 | 0.17 ± 0.02 |
| 12 | 0.10 ± 0.02 |
| 13 | 0.82 ± 0.2 |
| 14 | 0.14 ± 0.01 |
| 15 | 0.29 ± 0.16 |
| 16 | 1.46 ± 1.6 |
| 17 | 2.45 ± 1.0 |
| 18 | 0.39 ± 0.5 |
| 19 | 1.1 ± 0.6 |
| 20 | 2.66 ± 2.2 |

TABLE 4

| | Cytotoxicity | | | Plasmastability | |
|---|---|---|---|---|---|
| Ex. | Hela Cells GI$_{50}$ [µM] | Cos-7 Cells GI$_{50}$ [µM] | Hemolysis at 100 µM [%] | human pl. T$_{1/2}$ [min] | mouse pl. T$_{1/2}$ [min] |
| 1 | >50 | >50 | 0 | 240 | 240 |
| 2 | >50 | >50 | 0.6 | 240 | 240 |
| 3 | >50 | >50 | 0.1 | 240 | 240 |
| 4 | >50 | >50 | 1.9 | 240 | 240 |
| 5 | >50 | >50 | 1 | 240 | 240 |
| 6 | >50 | >50 | 2.4 | 240 | 240 |
| 7 | >50 | >50 | 0.6 | 240 | 240 |
| 8 | >50 | >50 | 0.3 | 240 | 240 |
| 9 | >50 | >50 | 2.1 | 240 | 240 |
| 10 | >50 | >50 | 0 | 240 | 240 |
| 11 | >50 | >50 | 1.7 | 240 | 240 |
| 12 | >50 | >50 | 0.9 | 240 | 240 |
| 13 | >50 | >50 | 0.7 | 240 | 240 |
| 14 | >50 | >50 | 1 | 240 | 240 |
| 15 | >50 | >50 | 0.6 | 240 | 240 |
| 16 | >50 | >50 | 0.5 | 240 | 240 |
| 17 | >50 | >50 | 1 | 240 | 240 |
| 18 | >50 | >50 | 1.4 | 240 | 240 |
| 19 | >50 | >50 | 1.8 | 240 | 240 |
| 20 | >50 | >50 | 0.6 | 240 | 240 |

The invention claimed is:

1. Compounds of the general formula Cyclo(-Xaa$^1$-Xaa$^2$-Xaa$^3$-Cys$^4$-Xaa$^5$-Xaa$^6$-Xaa$^7$-Xaa$^8$-Arg$^9$-Tyr$^{10}$-Cys$^{11}$-Xaa$^{12}$-Xaa$^{13}$-Xaa$^{14}$-Xaa$^{15}$-Xaa$^{16}$-), disulfide bond between Cys$^4$ and Cys$^{11}$, wherein the amino acid residues are:
   Xaa$^1$: Tyr, H-γ$^4$-DiHTyr-OH;
   Xaa$^2$: His;
   Xaa$^3$: Ala;
   Xaa$^5$: $^D$, alloT, Ahb, or H-β$^3$-HSer-OH;
   Xaa$^6$: Ala;
   Xaa$^7$: $^D$Pro, $^D$Tyr, or $^D$Trp;
   Xaa$^8$: Dab;
   Xaa$^{12}$: Tyr;
   Xaa$^{13}$: Gln;
   Xaa$^{14}$: Lys;
   Xaa$^{15}$: $^D$Cha, NMe$^D$Ile, $^D$His, $^D$His(Bzl), $^D$4Pal, NMe$^D$-Tyr, NMe$^D$Lys, (ABu)G, $^D$Ile, NMe$^D$Ala, $^D$Tyr, $^D$Lys, $^D$Dab or $^D$Pro;
   Xaa$^{16}$: Pro, or Oic.

2. Compounds according to claim 1, wherein the amino acid residues are exclusively α-amino acid residues, and wherein the α-amino acid residues are:
   Xaa$^1$: Tyr;
   Xaa$^2$: His;
   Xaa$^3$: Ala;
   Xaa$^5$: $^D$alloT;
   Xaa$^6$: Ala;
   Xaa$^7$: $^D$Pro, $^D$Tyr or $^D$Trp;
   Xaa$^8$: Dab;
   Xaa$^{12}$: Tyr;
   Xaa$^{13}$: Gln;
   Xaa$^{14}$: Lys;
   Xaa$^{15}$: $^D$Cha, NMe$^D$Ile, $^D$His, $^D$His(Bzl), $^D$4Pal, NMe$^D$-Tyr, NMe$^D$Lys, (ABu)G, $^D$Ile, NMe$^D$Ala, $^D$Tyr, $^D$Lys, $^D$Dab or $^D$Pro
   Xaa$^{16}$: Pro or Oic.

3. Enantiomers of the compounds as defined in claim 1.

4. A pharmaceutical composition containing a compound according to claim 1 and a pharmaceutically inert carrier.

5. Compositions according to claim 4 in a form suitable for oral, topical, transdermal, injection, buccal, transmucosal, pulmonary or inhalation administration.

6. Compositions according to claim 4 or 5 in form of tablets, dragees, capsules, solutions, liquids, gels, plaster, creams, ointments, syrup, slurries, suspensions, spray, nebuliser or suppositories.

7. A CXCR4 antagonizing medicament, comprising the compounds according to claim 1.

8. A process for the manufacture of compounds according to claim 1, which process comprises:
   (a) coupling an appropriately functionalized solid support with an appropriately N-protected derivative of that amino acid which in the desired end-product corresponds to Xaa$^n$, wherein n is 16, 8, 7, 6, or 3, any functional group which may be present in said N-protected amino acid derivative being likewise appropriately protected;
   (b) removing the N-protecting group from the product thus obtained;
   (c) coupling the product thus obtained with an appropriately N-protected derivative of that amino acid which in the desired end-product corresponds to Xaa$^{n-1}$, any functional group which may be present in said N-protected amino acid derivative being likewise appropriately protected;
   (d) removing the N-protecting group from the product obtained in step (c);
   (e) effecting steps substantially corresponding to steps (c) and (d) using appropriately N-protected derivatives of amino acids which in the desired end-product are in positions n-2 to 1, any functional group(s) which may be present in said N-protected amino acid derivatives being likewise appropriately protected;
   (f) if n is not 16, further effecting steps substantially corresponding to steps (c) and (d) using appropriately N-protected derivatives of amino acids which in the desired end-product are in positions 16 to n+1, any functional group(s) which may be present in said N-protected amino acid derivatives being likewise appropriately protected;
   (g) forming an interstrand linkage between side-chains of Cys at positions P4 and P11; or alternatively, forming the aforesaid linkage subsequent to step (j), as described herein below;
   (h) detaching the product thus obtained from the solid support;
   (i) cyclizing the product cleaved from the solid support;
   (j) removing any protecting groups present on functional groups of any members of the chain of amino acid residues and, if desired, any protecting group(s) which may in addition be present in the molecule; and
   (k) if desired, converting the product thus obtained into a pharmaceutically acceptable salt or converting a pharmaceutically acceptable, or unacceptable, salt thus obtained into the corresponding free compound or into a different, pharmaceutically acceptable, salt.

9. A modification of the processes claim 8 for the manufacture of compounds according to claim 3 in which enantiomers of all chiral starting materials are used.

10. Compounds according to claim 1, wherein the amino acid residues are:
   Xaa$^1$ is H-γ4-DiHTyr-OH; and/or
   Xaa$^5$ is $^D$alloT, Ahb, or H-β$^3$-HSer-OH; and/or
   Xaa$^{15}$ is $^D$Cha, NMe$^D$Ile, $^D$His, $^D$His(Bzl), $^D$4Pal, NMe$^D$-Tyr, NMe$^D$Lys, (ABu)G, $^D$Ile, NMe$^D$Ala, $^D$Tyr, $^D$Lys, or $^D$Dab; and/or
   Xaa$^{16}$ is Oic.

11. Compounds according to claim 2, wherein the amino acid residues are:
   Xaa$^5$ is $^D$alloT; and/or
   Xaa$^{15}$ is $^D$Cha, NMe$^D$Ile, $^D$His, $^D$His(Bzl), $^D$4Pal NMe$^D$-Tyr, NMe$^D$Lys, (ABu)G, $^D$Ile, NMe$^D$Ala, $^D$Tyr, $^D$Lys, or $^D$Dab; and/or
   Xaa$^{16}$ is Oic.

* * * * *